(12) United States Patent
Boger

(10) Patent No.: US 8,940,754 B2
(45) Date of Patent: Jan. 27, 2015

(54) 10'-FLUORINATED VINCA ALKALOIDS PROVIDE ENHANCED BIOLOGICAL ACTIVITY AGAINST MDR CANCER CELLS

(75) Inventor: Dale L. Boger, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 13/580,340

(22) PCT Filed: Feb. 9, 2011

(86) PCT No.: PCT/US2011/024230
§ 371 (c)(1),
(2), (4) Date: Aug. 21, 2012

(87) PCT Pub. No.: WO2011/103007
PCT Pub. Date: Aug. 25, 2011

(65) Prior Publication Data
US 2012/0329822 A1    Dec. 27, 2012

Related U.S. Application Data

(60) Provisional application No. 61/306,786, filed on Feb. 22, 2010.

(51) Int. Cl.
*A01N 43/42* (2006.01)
*A61K 31/44* (2006.01)
*C07D 487/00* (2006.01)
*C07D 491/00* (2006.01)
*C07D 513/00* (2006.01)
*C07D 519/04* (2006.01)

(52) U.S. Cl.
CPC .................................. *C07D 519/04* (2013.01)
USPC .......................................... 514/283; 540/478

(58) Field of Classification Search
USPC .......................... 514/286, 283; 540/461, 478
See application file for complete search history.

(56) References Cited

U.S. PATENT DOCUMENTS

| 6,127,377 A | 10/2000 | Duflos et al. |
| 6,723,338 B1 | 4/2004 | Sarris et al. |
| 2010/0093997 A1 | 4/2010 | Moisan et al. |

FOREIGN PATENT DOCUMENTS

WO    WO 2005055939 A2 *  6/2005

OTHER PUBLICATIONS

Runguphan et. al., Proceedings of the National Academy of Sciences, 2009, National Academy of Sciences, vol. 106, No. 33, pp. 13673-13678.*
Beger et. al., World Journal of Surgery, 2003, Societe Internationale de Chirurgie, vol. 27, pp. 1075-1084.*
Chabner et. al., Nature Reviews Cancer, 2005, Nature Publishing Group, vol. 5, pp. 65-72.*
Leaf, Fortune, Mar. 9, 2004, Time Inc., pp. 1-13.*
Schwartzbaum et. al., Nature Clinical Practice Neurology, 2006, Nature Publishing Group, vol. 2, No. 9, pp. 494-503.*
http://www.cancer.gov/cancertopics/types/alphalist/y.*
WO 2011/103007 First page and International Search Report, Aug. 25, 2011.
Smith et al., *Cancer* 51(3):417-422 (Feb. 1983)—Abstract.
*Goodman & Gilman's The Pharmaceutical Basis of Therapeutics*, Brunton et al. Eds., 11th ed., McGraw-Hill, 1350-1352 (2006).

* cited by examiner

*Primary Examiner* — Sarah Pihonak
(74) *Attorney, Agent, or Firm* — Husch Blackwell, LLP

(57) ABSTRACT

A 10'-fluoro-vinca alkaloid compound or its pharmaceutically acceptable salt is disclosed, as are methods of its preparation and use. A disclosed 10'-fluoro-vinca alkaloid compound has better cytotoxic potency against leukemia and cancer cell lines, and is about 8-times more cytotoxic to a multiple drug resistant cancer cell line than is a parental 10'-unsubstituted vinca alkaloid.

30 Claims, No Drawings

10'-FLUORINATED *VINCA* ALKALOIDS PROVIDE ENHANCED BIOLOGICAL ACTIVITY AGAINST MDR CANCER CELLS

CROSS-REFERENCE TO RELATED APPLICATION

This application claims priority from provisional application No. 61/306,786, filed Feb. 22, 2010, whose disclosures are incorporated herein by reference.

GOVERNMENTAL SUPPORT

The present invention was made with governmental support pursuant to grants CA115526, CA042056 and GM087948 from the National Institutes of Health. The government has certain rights in the invention.

BACKGROUND ART

Vinca alkaloids, originally isolated from the periwinkle plant [*Vinca rosea* Linn., now *Cantharanthus roseus* (L.) G. Don] are a family of indole-indoline dimeric compounds that contain a four-ring system containing an indole linked to a five-ring system containing an indoline. Two of those natural alkaloids, vinblastine and vincristine, are important clinical agents in the treatment of leukemias, lymphomas and testicular cancer.

The semi-synthetic vinca alkaloid, vinorelbine, has activity against lung cancer and breast cancer, and vindesine is used to treat lung cancer and acute leukemia and less often for melanoma, and breast cancer. [*Goodman & Gilman's The Pharmaceutical Basis of Therapeutics*, Hardman et al. Eds., 9th ed., McGraw-Hill, 1257-1260, 1996] The 19',20'-anhydrovinca alkaloids (anhydrovinca alkaloids) are also active in treating the above diseases, albeit, they are usually somewhat less potently cytotoxic. Thus, the semi-synthetic anhydrovinca alkaloid, vinorelbine, has activity against lung cancer and breast cancer, and anhydrovinblastine is active as is shown hereinafter. Anhydrovincristine and anhydrovindesine are also cytotoxic.

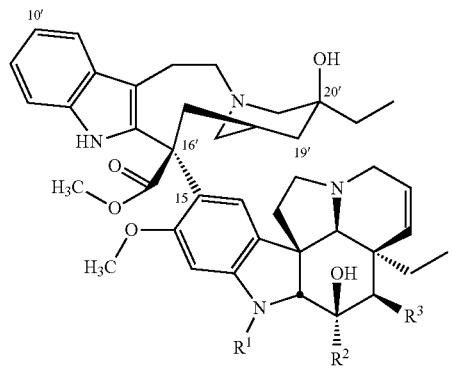

| | $R^1$ | $R^2$ | $R^3$ |
|---|---|---|---|
| Vinblastine (1) | —CH$_3$ | —C(O)—OCH$_3$ | —O—C(O)—CH$_3$ |
| Vincristine (2) | —CHO | —C(O)—OCH$_3$ | —O—C(O)—CH$_3$ |
| Vindesine | —CH$_3$ | —C(O)—NH$_2$ | —OH |

| | n | $R^1$ | $R^2$ | $R^3$ |
|---|---|---|---|---|
| Vinorelbine | 1 | —CH$_3$ | —C(O)—OCH$_3$ | —O—C(O)—CH$_3$ |
| Anhydro-vinblastine (4) | 2 | —CH$_3$ | —C(O)—OCH$_3$ | —O—C(O)—CH$_3$ |
| Anhydro-vincristine | 2 | —CHO | —C(O)—OCH$_3$ | —O—C(O)—CH$_3$ |
| Anhydro-vindesine | 2 | —CH$_3$ | —C(O)—NH$_2$ | —OH |

Vinblastine (1) and vincristine (2) represent the most widely recognized members of the vinca alkaloids as a result of their clinical use as antitumor drugs. [Noble et al., *Ann. N.Y. Acad. Sci.* 1958, 76:882; Noble, *Lloydia* 1964, 27:280; Svoboda et al., *J. Am. Pharm. Assoc. Sci. Ed.* 1959, 48:659; Moncrief et al., *J. Am. Chem. Soc.* 1965, 84:4963; Review:: Neuss et al., In *The Alkaloids*; Brossi et al Eds.; Academic: San Diego, 1990; Vol. 37:229] Originally isolated in trace quantities from *Cantharanthus roseus* (L.) G. Don, [Noble et al., *Ann. N.Y. Acad. Sci.* 1958, 76:882; Noble, *Lloydia* 1964, 27:280; Svoboda et al., *J. Am. Pharm. Assoc. Sci. Ed.* 1959, 48:659] their biological properties were among the first to be shown to arise from inhibition of microtubule formation and mitosis that today is still regarded as one of the more successful drug targets for the treatment of cancer. [Reviews: Neuss et al., In *The Alkaloids*; Brossi et al Eds.; Academic: San Diego, 1990; Vol. 37:229; Pearce, H. L. In The Alkaloids; Brossi et al. Eds.; Academic: San Diego, 1990; Vol. 37:145; Borman et al., In *The Alkaloids*; Brossi et al. Eds.; Academic: San Diego, 1990; Vol. 37:133; Fahy *Curr. Pharm. Design* 2001, 7:1181; Kuehne et al., In *The Alkaloids*; Brossi et al. Eds.; Academic: San Diego, 1990; Vol. 37:77; Potier, *J. Nat. Prod.* 1980, 43:72; Kutney, *Nat. Prod. Rep.* 1990, 7:85; Kutney, *Synlett* 1991, 11; (e) Kutney, *Acc. Chem. Res.* 1993, 26:559; For recent studies, see: Kuehne et al., *Org. Biomol. Chem.* 2003, 1:2120; Miyazaki et al., *Org. Lett.* 2007, 9:4737].

The vinca alkaloids, alone or combined with other antineoplastic compounds such as cisplatin, bleomycin and the like, are particularly effective in treating a variety of cancerous conditions and are the medications of choice for those treatments. However, multiple drug resistance (MDR) of the treated cells can lead to a loss of efficacy of the drugs in treatment. Extensive research is being carried out to overcome the problem of MDR so that the once effective treatments can be continued as needed.

The inventor and his research group recently utilized a one-pot, two-step biomimetic Fe(III)-promoted coupling of vindoline (3) with catharanthine (4) in the total synthesis of

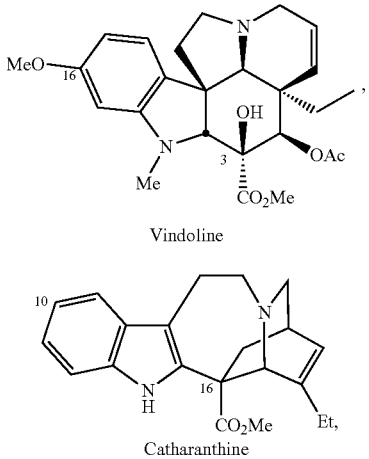

vinblastine and reported its extension to the preparation of a series of related natural products and key analogues. [Ishikawa et al., *J. Am. Chem. Soc.* 2008, 130:420; Ishikawa et al., *J. Am. Chem. Soc.* 2009, 131:4904] Although key mechanistic insights into this coupling [Ishikawa et al., *J. Am. Chem. Soc.* 2008, 130:420; Ishikawa et al., *J. Am. Chem. Soc.* 2009, 131:4904; Vukovic et al., *Tetrahedron* 1988, 44:325; for an analogous electrochemical coupling (0.6 V in buffer; NaBH$_4$) to provide anhydrovinblastine, see: Gunic et al., *J. Chem. Soc., Chem. Commun.* 1993, 1496; For an enzymatic coupling, see: Sagui et al., *Tetrahedron* 2009, 65, 312; For additional seminal studies on the Fe(III)-coupling to provide anhydrovinblastine, see Szantay et al., *Tetrahedron* 1991, 47:1265; Sundberg et al., *Tetrahedron* 1998, 54:6259] and subsequent olefin oxidation [Ishikawa et al., *J. Am. Chem. Soc.* 2009, 131:4904; Sakamoto et al, JP 04164087 (*Chem. Abstr.* 1992, 117:192139); Tan et al., U.S. Pat. No. 5,037,977 (*Chem. Abstr.* 1990, 113, 6663)] have been disclosed in the studies to date, the unusual differences in the diastereoselectivity of the Fe(III)-promoted coupling (single natural C16' diastereomer at 25° C. in aqueous buffer) and the more traditional Polonovski fragmentation [Potier et al., *J. Chem. Soc.*, Chem. Commun. 1975, 670; Langlois et al., *J. Am. Chem. Soc.* 1976, 98:7017; Sundberg et al., *Tetrahedron* 1992, 48:277; Kutney et al., *Heterocycles* 1975, 3:639; Kutney et al., *Helv. Chim. Acta* 1976, 59:2858] (5:1 at −78° C. or 1:1 at 0° C. in CH$_2$Cl$_2$) or 3-chloroindolenine-based couplings suggests that there are mechanistic features of the former reaction that are not yet well understood and that affect the resulting C16' stereochemistry. [For additional approaches to effecting analogous couplings, see: Magnus et al., *J. Am. Chem. Soc.* 1990, 112:8210; Magnus et al., *J. Am. Chem. Soc.* 1992, 114:10232; Kuehne et al., *J. Org. Chem.* 1991, 56:513; Bornmann et al., *J. Org. Chem.* 1992, 57:1752; Kuehne et al., *J. Org. Chem.* 1987, 52:4340; Schill et al., *Tetrahedron* 1987, 43:3765; Yokoshima et al;., *J. Am. Chem. Soc.* 2002, 124:2137; Kuboyama et al., *Proc. Natl. Acad. Sci. USA* 2004, 101:11966]

N-methyl catharanthine fails to couple with vindoline under either set of conditions, indicating that both approaches require the free indole NH and suggesting that they both may potentially proceed through a common azabenzfulvene intermediate (equation 1, below). Yet, the two approaches proceed with the distinct stereochemical outcomes.

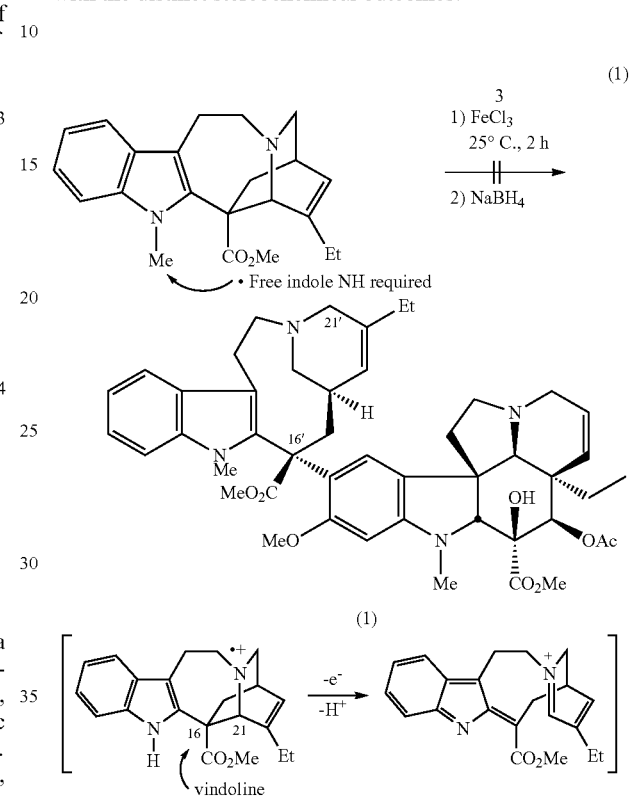

In the case of the Fe(III)-promoted coupling, the attack by vindoline formally occurs with clean inversion of the stereochemistry at the reacting C16 center of the C16-C21 bond undergoing cleavage and it has been suggested that initial radical cation formation occurs at the basic tertiary amine. [Vukovic et al., *Tetrahedron* 1988, 44:325; For an analogous electrochemical coupling (0.6 V in buffer; NaBH$_4$) to provide anhydrovinblastine, see: Gunic et al., *J. Chem. Soc.*, Chem. Commun. 1993, 1496; For an enzymatic coupling, see: Sagui et al., *Tetrahedron* 2009, 65, 312; For additional seminal studies on the Fe(III)-coupling to provide anhydrovinblastine, see Szantay et al., *Tetrahedron* 1991, 47:1265; Sundberg et al., *Tetrahedron* 1998, 54:6259]

Disclosed hereinafter is the first report of the examination of catharanthine substituent effects on the coupling reaction, establishing the importance of its C16 methyl ester and the electronic impact of a catharanthine C10 indole substituent on biologic activity. An unexpected finding was the enhanced activity of the 10'-fluorinated vinca alkaloids compared to their unsubstituted parental vinca alkaloid compounds (10'-hydrido vinca alkaloid compounds), and particularly the enhanced activity against multiple drug resistant cells. The mechanistic implications are also noted and discussed.

BRIEF SUMMARY OF THE INVENTION

The present invention contemplates an improved vinca alkaloid molecule (compound) that is a 10'-fluoro-vinca alkaloid or a pharmaceutically acceptable salt thereof, its method of preparation and use. A contemplated compound exhibits enhanced activity over the parental unfluorinated (10'-hydrido; H) parent compound in in vitro assays against at least one of three cell lines that are L1210 (a mouse leukemia cell line) HCT116 (a human colorectal carcinoma line), and HCT116/VM46 (a multidrug resistant human colorectal carcinoma line).

A contemplated compound is typically and preferably used dissolved or dispersed in a physiologically (pharmaceutically) acceptable carrier to provide a pharmaceutical composition. Such a composition is preferably adapted for parenteral administration, as intravenously. A contemplated compound is present in such a composition in an effective microtubule formation-inhibiting or mitosis-inhibiting amount. Such an amount is typically similar to that amount used for the parental vinca alkaloid in the same composition for treating the same disease state.

A method of treating cancer, leukemia or lymphoma is also contemplated. In accordance with that method, an above-described pharmaceutical composition is administered to a mammal in need thereof. The administration is continued a plurality of times, as is usual for such treatments.

Further contemplated is 10-fluoro-catharanthine, an intermediate in the synthesis of several contemplated 10'-fluoro-vinca alkaloid compounds.

The present invention has several benefits and advantages.

One benefit of the invention is that a contemplated 10'-fluorovinca alkaloid is about eight times more potent as a cytotoxic agent against a leukemia or a cancer cell line than is the parental, unsubstituted vinca alkaloid.

One advantage of the invention is that a contemplated compound is about eight times more potent against multiple drug resistant cancer cell lines than is the parental, unsubstituted vinca alkaloid compound.

Another benefit of the invention, is that a contemplated compound is relatively easy to synthesize.

DETAILED DESCRIPTION OF PREFERRED EMBODIMENTS

The present invention contemplates a 10'-fluoro-vinca alkaloid compound or its pharmaceutically acceptable salt. It has been unexpectedly found that a contemplated 10'-fluoro-vinca alkaloid exhibits anti-cancer biological activity (cytotoxicity) that has about eight times the potency as that exhibited by a parental, unsubstituted (10-hydrido) vinca alkaloid compound when assayed against normal (drug-sensitive) leukemia and cancer cell lines. Even more unexpectedly, a contemplated 10'-fluoro-substituted vinca alkaloid also exhibited about eight-fold enhanced cytotoxicity over the parental unsubstituted vinca alkaloid against a multiple drug resistant cancer cell line.

The phrase "parental, unsubstituted (10'-hydrido) vinca alkaloid" and similar phrases are used herein to refer to a vinca alkaloid such as vinblastine or vincristine, whose biological activity is compared herein to a contemplated compound such as 10'-fluorovinblastine or 10'-fluorovincristine, respectively. Thus, the activity of 10'-fluoro-vinblastine is compared to the activity of vinblastine when both are screened against the same call line or lines. Similarly, the activity of 10'-fluorovincristine is compared to vincristine. Similar comparisons are contemplated between other pairs of 10'-fluoro and 10'-hydrido vinca alkaloids, such as 10'-fluoroanhydrovinblastine and anhydrovinblastine.

Illustrative compounds of the invention are illustrated in the Tables A and B, below.

TABLE A

| | $R^1$ | $R^2$ | $R^3$ |
|---|---|---|---|
| 10'-Fluorovinblastine (19b) | —$CH_3$ | —C(O)—$OCH_3$ | —O—C(O)—$CH_3$ |
| 10'-Fluorovincristine (28) | —CHO | —C(O)—$OCH_3$ | —O—C(O)—$CH_3$ |
| 10'-Fluorovindesine | —$CH_3$ | —C(O)—$NH_2$ | —OH |
| 1-Desmethyl-10'-fluoro-vinblastine (27) | —H | —C(O)—$OCH_3$ | —O—C(O)—$CH_3$ |

TABLE B

| | n | $R^1$ | $R^2$ | $R^3$ |
|---|---|---|---|---|
| 10'-Fluoro-vinorelbine | 1 | —$CH_3$ | —C(O)—$OCH_3$ | —O—C(O)—$CH_3$ |
| 10'-Fluoro-anhydro-vinblastine (19a) | 2 | —$CH_3$ | —C(O)—$OCH_3$ | —O—C(O)—$CH_3$ |

TABLE B-continued

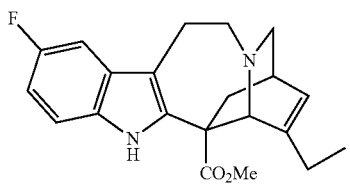

| | n | R¹ | R² | R³ |
|---|---|---|---|---|
| 10'-Fluoro-anhydro-vincristine | 2 | —CH=O | —C(=O)—OCH₃ | —O—C(=O)—CH₃ |
| 10'-Fluoro-anhydro-vindesine | 2 | —CH₃ | —C(=O)—NH₂ | —OH. |

Another way of describing a contemplated compound is as an improved vinca alkaloid molecule in which the improvement is fluoro-substitution at the 10'-position of the molecule. Particularly preferred of the improved vinca alkaloid molecules (compounds) are 10'-fluorovinblastine (19b) and 10'-fluoroanhydrovinblastine (19a).

10-Fluorocatharanthine, an intermediate in the synthesis of several contemplated 10'-fluoro-vinca alkaloid compounds is also contemplated herein. 10-Fluorocatharanthine corresponds in structure to compound 19, below.

19

Pharmaceutical Composition

A contemplated compound can also be used in the manufacture of a medicament (pharmaceutical composition) that is useful at least for treating cancer, lymphoma or leukemia in a subject in need thereof, as is the unflourinated (10'-hydrido) parent compound. When so used, pharmaceutically acceptable salts, buffers and the like are present that collectively are referred to as pharmaceutically acceptable diluents as compared to those that can be present in a composition that is not intended for pharmaceutical use, as in an in vitro assay.

A compound of the invention can be provided for use by itself, or as a pharmaceutically acceptable salt. The contemplated compounds and their parental 10' hydrido compounds are tetra-amines. Parental 10'-hydrido compound vinblastine has reported pKa values of 5.4 and 7.4, whereas vincristine has reported pKa values of 6.04 and 7.67. [*Merck Index*, 13$^{th}$ ed. Merck & Co., Whitehouse Station, N.J., 2001, pages 1778-1779.] Both compounds are sold commercially as their sulfate salts.

Exemplary salts useful for a contemplated compound include but are not limited to the following: sulfate, hydrochloride, hydro bromides, acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, palmoate, pectinate, persulfate, 3-phenyl-propionate, picrate, pivalate, propionate, succinate, tartrate, thiocyanate, tosylate, mesylate and undecanoate.

The reader is directed to Berge, 1977 *J. Pharm. Sci.* 68(1): 1-19 for lists of commonly used pharmaceutically acceptable acids and bases that form pharmaceutically acceptable salts with pharmaceutical compounds.

In some cases, the salts can also be used as an aid in the isolation, purification or resolution of the compounds of this invention. In such uses, the acid used and the salt prepared need not be pharmaceutically acceptable.

As is seen from the data that follow, a contemplated compound is active in in vitro assay studies at nanomolar to micromolar amounts. When used in an assay such as an in vitro assay, a contemplated compound is present in the composition in an amount that is sufficient to provide a concentration of about 0.5 nM to about 1000 nM, preferably about 1 nM to about 50 nM to a contact cells to be assayed.

A contemplated pharmaceutical composition contains a microtubule formation-inhibiting or mitosis-inhibiting amount of a compound of a contemplated 10'-fluoro-vinca alkaloid or a pharmaceutically acceptable salt thereof dissolved or dispersed in a physiologically (pharmaceutically) acceptable carrier. Such a composition can be administered to mammalian cells in vitro as in a cell culture, or in vivo as in a living, host mammal in need.

More usually, anti-neoplastic drugs are administered in vivo in a weight amount per square meter of the recipient's body surface area (bsa). For adults, this amount is typically about 1 to about 20 mg/m² bsa, and about one-half those amounts for children, with an amount being chosen so that the maximal amount does not cause leukopenia. Children weighing about 10 kg or less are typically dosed at about 0.05 mg/kg.

A contemplated composition is typically administered to a subject in need thereof a plurality of times within one month, such as weekly, and can be administered over a period of several months to several years. More usually, a contemplated composition is administered a plurality of times over a course of treatment.

In usual practice, a contemplated 10'-fluoro-vinca alkaloid is administered to treat the same disease state in the same amount and at the same intervals as is a parental, 10'-hydrido-vinca alkaloid. A contemplated 10'-fluoro-vinca alkaloid can be utilized as a first course of treatment, and is preferably administered if there is relapse after a first or later course of treatment, particularly where multiple drug resistance is shown or suspected (indicated).

A contemplated pharmaceutical composition can be administered orally (perorally) or parenterally, which is preferred, in a formulation containing conventional nontoxic pharmaceutically acceptable carriers, adjuvants, and vehicles as desired. The term parenteral as used herein includes subcutaneous injections, intravenous (which is most preferred), intramuscular, intrasternal injection, or infusion techniques. Formulation of drugs is discussed in, for example, Hoover, John E., *Remington's Pharmaceutical Sciences*, Mack Publishing Co., Easton, Pa.; 1975 and Liberman, H. A. and Lachman, L., Eds., *Pharmaceutical Dosage Forms*, Marcel Decker, New York, N.Y., 1980.

Solid dosage forms for oral administration can include capsules, tablets, pills, powders, and granules. The amount of a contemplated compound in a solid dosage form is as discussed previously, an amount sufficient to provide a concentration of about 0.5 nM to about 1000 nM, preferably about 1 nM to about 50 nM, in the serum or blood plasma. A solid dosage form can also be administered a plurality of times during a one week time period.

In such solid dosage forms, a compound of this invention is ordinarily combined with one or more adjuvants appropriate to the indicated route of administration. If administered per os, the compounds can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, magnesium or calcium carbonate or bicarbonate. Tablets and pills can additionally be prepared with enteric coatings.

A contemplated pharmaceutical composition is preferably adapted for parenteral administration. Thus, a pharmaceutical composition is preferably in liquid form when administered, and most preferably, the liquid is an aqueous liquid, although other liquids are contemplated as discussed below, and a presently most preferred composition is an injectable preparation.

Thus, injectable preparations, for example, sterile injectable aqueous or oleaginous solutions or suspensions can be formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be employed are water, Ringer's solution, and isotonic sodium chloride solution, phosphate-buffered saline.

Other liquid pharmaceutical compositions include, for example, solutions suitable for parenteral administration. Sterile water solutions of a 10'-fluoro-vinca alkaloid active component or sterile solution of the active component in solvents comprising water, ethanol, or propylene glycol are examples of liquid compositions suitable for parenteral administration. In some aspects, a contemplated 10'-fluoro-vinca alkaloid is provided as a dry powder that is to be dissolved in an appropriate liquid medium such as sodium chloride for injection prior to use.

In addition, sterile, fixed oils are conventionally employed as a solvent or suspending medium. For this purpose any bland fixed oil can be employed including synthetic mono- or diglycerides. In addition, fatty acids such as oleic acid find use in the preparation of an injectable composition. Dimethyl acetamide, surfactants including ionic and non-ionic detergents, polyethylene glycols can be used. Mixtures of solvents and wetting agents such as those discussed above are also useful.

Sterile solutions can be prepared by dissolving the active component in the desired solvent system, and then passing the resulting solution through a membrane filter to sterilize it or, alternatively, by dissolving the sterile compound in a previously sterilized solvent under sterile conditions.

A mammal in need of treatment (a subject) and to which a pharmaceutical composition containing a contemplated compound is administered can be a primate such as a human, an ape such as a chimpanzee or gorilla, a monkey such as a cynomolgus monkey or a macaque, a laboratory animal such as a rat, mouse or rabbit, a companion animal such as a dog, cat, horse, or a food animal such as a cow or steer, sheep, lamb, pig, goat, llama or the like.

Where an in vitro assay is contemplated, a sample to be assayed such as cells and tissue can be used. These in vitro compositions typically contain the water, sodium or potassium chloride, and one or more buffer salts such as and acetate and phosphate salts, Hepes or the like, a metal ion chelator such as EDTA that are buffered to a desired pH value such as pH 4.0-8.5, preferably about pH 7.2-7.4, depending on the assay to be performed, as is well known.

Preferably, the pharmaceutical composition is in unit dosage form. In such form, the composition is divided into unit doses containing appropriate quantities of the active compound. The unit dosage form can be a packaged preparation, the package containing discrete quantities of the preparation, for example, in vials or ampules.

In another preferred embodiment, a contemplated 10'-fluoro-vinca alkaloid is administered with one or more other anti-neoplastic compounds. Such joint therapy is well known in the art, with other drugs such as cisplatin, 5-fluorouracil and the like being co-administered. That co-administration is usually physically separate administrations of each compound that are timed so that the two or more active agents can, act in concert.

Chemical Studies

The electron-withdrawing properties of the C-16 methyl ester were anticipated to be key to the coupling of catharanthine with vindoline. Consequently, only a small series of alternative electron-withdrawing substituents were examined ($R=CO_2Et$, $CONH_2$, $CN$, $CHO$, $CO_2H$) along with derivatives where it was removed ($R=H$), or replaced with an alkyl ($R=CH_2OH$, $CH_3$) or alcohol ($R=OH$) substituent (Tables 1A and 1B, below). [Details of the substrate preparations are set out hereinafter.]

TABLE 1A

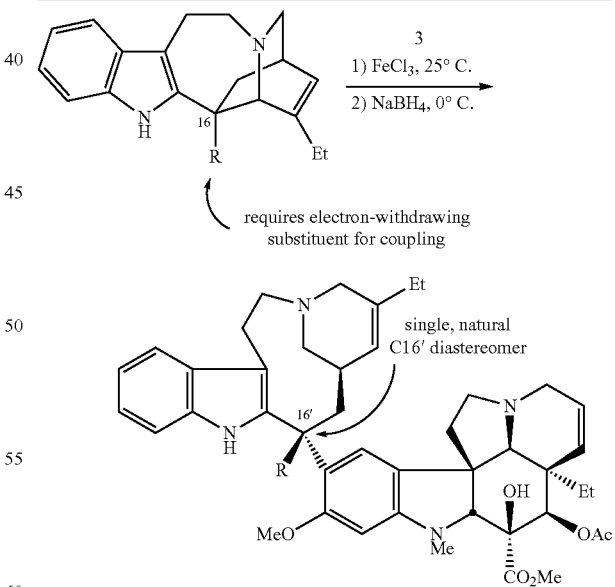

| Compd | Product (% yield) | IC$_{50}$ (nM) | | |
|---|---|---|---|---|
| | | L1210 | HCT116 | HCT116/VM46 |
| 4, R = CO$_2$Me | 4a (90%) | 65 | 75 | 600 |
| 5, R = CO$_2$Et | 5a (82%) | 620 | 640 | 4100 ← 10-fold |
| 6, R = CN | 6a (95%) | 6500 | 6100 | 6800 ← 100-fold |

TABLE 1A-continued

| | | | | |
|---|---|---|---|---|
| 7, R = CONH$_2$ | 7a (79%) | >10000 | >10000 | >10000 ← >100-fold |
| 8, R = CHO | 8a (49%) | 6300 | 7000 | >10000 ← 100-fold |
| 9, R = CO$_2$H | 9a (0%) | — | — | — |
| 10, R = H | 10a (0%) | — | — | — |
| 11, R = CH$_2$OH | 11a (0%) | — | — | — |
| 12, R = Me | 12a (0%) | — | — | — |
| 13, R = OH | 13a (0%) | — | — | — |

TABLE 1B

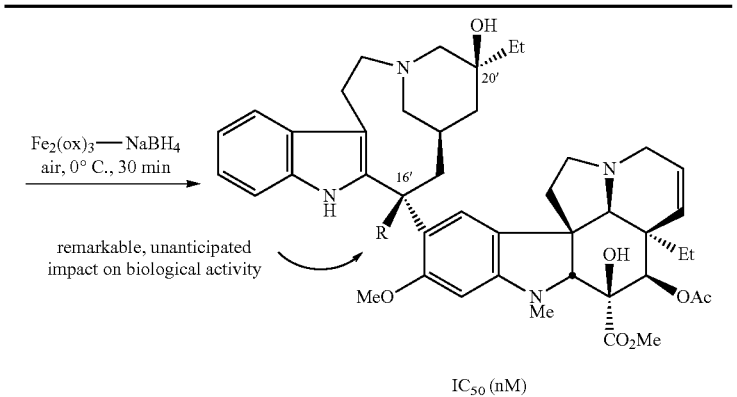

| | | IC$_{50}$ (nM) | | |
|---|---|---|---|---|
| Compd | Product | L1210 | HCT116 | HCT116/VM46 |
| R = CO$_2$Me | 1 | 6.0 | 6.8 | 600 |
| R = CO$_2$Et | 5b | 60 | 70 | 830 ← 10-fold |
| R = CN | 6b | 630 | 670 | 7400 ← 100-fold |
| R = CONH$_2$ | 7b | >10000 | >10000 | >10000 ← >1000-fold |
| R = CH$_2$OH | 11b[a] | 6500 | 5800 | >10000 ← 1000-fold |

[a]Obtained from the coupling and oxidation of 8.

As anticipated, the coupling (5 equiv FeCl$_3$, 0.05 N aq HCl—CF$_3$CH$_2$OH 10:1, 25° C., 2 hours) required the presence of a C16 electron-withdrawing substituent with Compounds 4-7 providing comparable conversions to the corresponding anhydrovinblastine analogue, and the aldehyde Compound 8 providing a perceptibly lower yield for the generation of product reflecting some aldehyde reduction upon iminium ion reduction with NaBH$_4$. Interestingly, the carboxylic acid derivative Compound 9 failed to couple with Compound 3, as did the catharanthine analogue Compounds 10-13 that lack a C16 electron-withdrawing substituent.

Because this vinblastine site has not been probed beyond reduction or methyl ester hydrolysis and subsequent decarboxylation, [Reviews:: Neuss et al., *In The Alkaloids; Brossi et al Eds.; Academic: San Diego*, 1990; Vol. 37:229; Potier et al., *Comp. Rend.* 1979, 173:414; Barnett et al., *J. Med. Chem.* 1978, 21:88] each derivative was also converted to the corresponding vinblastine analogue either by exposing the anhydrovinblastine analogue to the conditions developed for oxidation of the C15'-C20' double bond with installation of the 020' tertiary alcohol (Fe$_2$(ox)$_3$-NaBH$_4$, air, 0° C., 30 minutes), [Ishikawa et al., *J. Am. Chem. Soc.* 2009, 131:4904; Sakamoto et al., *JP* 04164087 (*Chem. Abstr.* 1992:117, 192139); Tan et al., U.S. Pat. No. 5,037,977 (*Chem. Abstr.* 1990, 113:6663)] or more directly using the one-pot, two-step procedure of coupling and in situ oxidation. [Ishikawa et al., *J. Am. Chem. Soc.* 2008, 130:420; Ishikawa et al., *J. Am. Chem. Soc.* 2009, 131:4904]

Whereas the important role of the C16 methyl ester in the coupling reaction could be anticipated, the remarkable sensitivity of the properties of the resulting anhydrovinblastine and vinblastine analogues to modifications at this site was unexpected. Both series exhibited a striking sensitivity to the presence and nature of the C-16' substituent. Simply replacing the C-16' methyl ester with the corresponding ethyl ester resulted in a 10-fold loss in activity, a nitrile or aldehyde substitution resulted in a 100-fold loss in activity, incorporation of a hydroxymethyl group led to a 1000-fold loss in activity, and the primary carboxamide replacement produced a >1000-fold loss in activity. Clearly, the role of the C-16' methyl ester extends well beyond facilitating the coupling reaction in the biosynthesis of the natural product; rather it plays an integral role in establishing the biological properties of the natural product presumably stabilizing the interaction of vinblastine with tubulin.

The second series of derivatives examined entailed C-10 indole substitution in catharanthine, para to the indole NH. A systematic series of electron-donating and electron-withdrawing substituents was examined that might provide further insight into the mechanistic details of the Fe(III)-promoted coupling (Tables 2A and 2B, below).

[Details of the Substrate Preparations are Set Out Hereinafter.]

TABLE 2A*

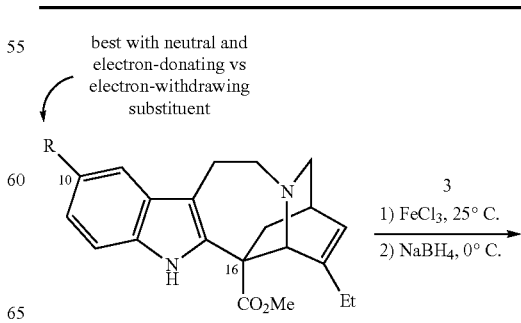

TABLE 2A*-continued

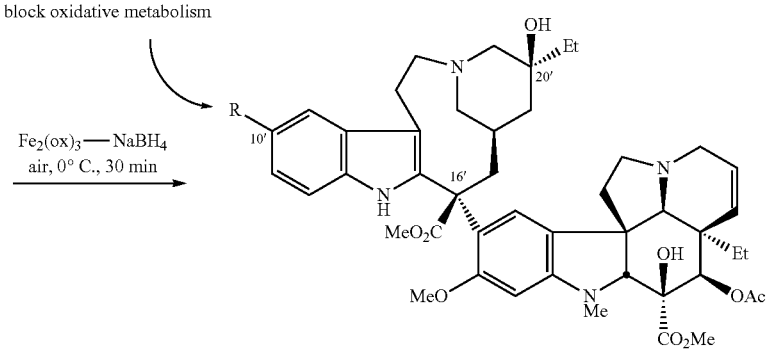

single, natural C16' diastereomer

| Compd | $\sigma_p$ | Product (% yield) | IC$_{50}$ (nM) | | |
|---|---|---|---|---|---|
| | | | L1210 | HCT116 | HCT116/VM46 |
| 14, R = NO$_2$ | 0.78 | 14a (0%) | — | — | — |
| 15, R = CN | 0.66 | 15a (<5%)[a] | 65 | 70 | 920 |
| 16, R = I | 0.28 | 16a (29%)[b,c] | 620 | 600 | 1800 |
| 17, R = Br | 0.26 | 17a (27%)[b] | 65 | 70 | 860 |
| 18, R = Cl | 0.24 | 18a (32%) | 60 | 70 | 800 |
| 19, R = F | 0.06 | 19a (65%) | 30 | 50 | 290 |
| 4, R = H | 0.00 | 4a (90%) | 65 | 75 | 600 |
| 20, R = SMe | 0.00 | 20a (70%) | 60 | 85 | 770 |
| 21, R = Me | −0.17 | 21a (95%) | 65 | 65 | 640 |
| 22, R = OMe | −0.27 | 22a (62%) | 550 | 640 | 5500 |
| 23, R = OH | −0.38 | 23a (0%) | — | — | — |
| 24, R = NHBoc | −0.17 | 24a (0%) | — | — | — |
| 25, R = NH$_2$ | −0.66 | 25a (0%) | — | — | — |
| 26, R = NMe$_2$ | −0.83 | 26a (0%) | — | — | — |

*See Table 2B for notes.

Direct side-by-side comparisons of 10'-fluorovinblastine (Compound 19b) and 10'-fluorovincristine (Compound 28) with vinblastine (Compound 1) and vincristine are provided below in Table 2C with values that represent multiple examinations with several independent samples, as compared to the single evaluations of Tables 2A and 2B. The results indicate that they are about 8-fold more potent than the natural products themselves.

TABLE 2C

| Compd | IC$_{50}$ (nM) | | |
|---|---|---|---|
| | L1210 | HCT116 | HCT116/VM46 |
| R' = Me (vinblastine) | | | |
| R = F | 0.7 | 0.9 | 80 |
| R = H | 6.0 | 6.8 | 600 |

TABLE 2B size & shape dependent impact on biological activity
(e.g., F > H > Cl > Me, Br >> I, SMe >> CN)
enhanced activity against resistant cell line (F > H)
block oxidative metabolism Fe$_2$(ox)$_3$—NaBH$_4$
air, 0° C., 30 min

| Compd | Product (% yield) | IC$_{50}$ (nM) | | |
|---|---|---|---|---|
| | | L1210 | HCT116 | HCT116/VM46 |
| R = CN | 15b (—)[d] | 700 | 670 | >10000 |
| R = I | 16b (27%) | 55 | 60 | 840 |
| R = Br | 17b (22%) | 8.0 | 8.6 | 270 |
| R = Cl | 18b (42%) | 6.2 | 7.6 | 720 |
| R = F | 19b (40%) | 0.7 | 0.9 | 80 |
| R = H | 1 (50%) | 6.0 | 6.8 | 600 |
| R = SMe | 20b (31%) | 45 | 35 | 740 |
| R = Me | 21b (40%) | 7.8 | 7.8 | 600 |
| R = OMe | 22b (48%) | 670 | 720 | >10000 |

[a]Compound 15a was obtained in 7% (20 vs 2 h).
[b]Run in 33% TFE-buffer.
[c]Also obtained in 40% (20 h) or 48% (60 h) vs 29% (2 h).
[d]Obtained by Pd-catalyzed cyanation of 16b.

TABLE 2C-continued

| R' = CHO (vincristine) | | | |
|---|---|---|---|
| R = F | 0.7 | 1.0 | 90 |
| R = H | 6.0 | 7.0 | 700 |

Moreover, C-10' is a site of oxidative metabolism of vinblastine, producing the metabolite 10'-hydroxyvinblastine (Compound 23b). [Neuss et al., *Helv. Chem. Acta* 1974, 57:1886]. Thus, substitution that blocks formation of this metabolite was viewed as an attribute to such derivatives. Additionally and as depicted in the X-ray structure of vinblastine bound to tubulin [Gigant et al., *Nature* 2005, 435:519], this site resides at one end of the upper portion of the T-shaped conformation of the tubulin-bound molecule, suggesting it makes critical contacts with the protein at a site sensitive to steric interactions.

With some notable exceptions, electron-withdrawing substituents were observed to slow or preclude coupling with vindoline, whereas catharanthine derivatives bearing neutral or electron-donating C-10 substituents participate effectively in the coupling reaction (5 equiv $FeCl_3$, 0.05 N aq HCl—$CF_3CH_2OH$ 10:1, 25° C., 2 hours). The exceptions to these generalizations were the C-10 amine derivatives Compounds 24-26 and the phenol Compound 23, which underwent competitive oxidation reactions (p-quinodiimine or p-quinoimine formation) and failed to support the coupling reaction.

A smooth trend of decreasing ease of coupling was observed with the electron-withdrawing substituents [H (90%)>F (65%)>Cl, Br, I (ca. 30%)>CN (about 5%)>$NO_2$ (0%)], the neutral and weakly electron-donating substituents coupled exceptionally well [e.g., H (90%), Me (95%), SMe (70%)], and the one derivative containing an even stronger electron-donating substituent (R=OMe, 62%) participated effectively in the reaction although the sampling was too small to assess a general trend. Nonetheless, the overall trends are clear, and indicate that the nucleophilic character of the indole nitrogen (its relative basicity vs acidity) or the oxidation potential of the indole play an important role in supporting the coupling and the oxidative fragmentation of the C16-C21 bond.

If one factors in the lack of coupling by N-methyl catharanthine (see equation 1) and based on close precedent for Fe(III)-mediated indole oxidation in the absence of the tertiary amine, [Bergman et al., *Tetrahedron Lett.* 1989, 30:5337], the results are consistent with both Fe(III)-mediated single electron oxidations occurring within the catharanthine indole where deprotonation of the initial radical cation would be required for the second oxidation and subsequent fragmentation to occur (equation 2, below).

(2)

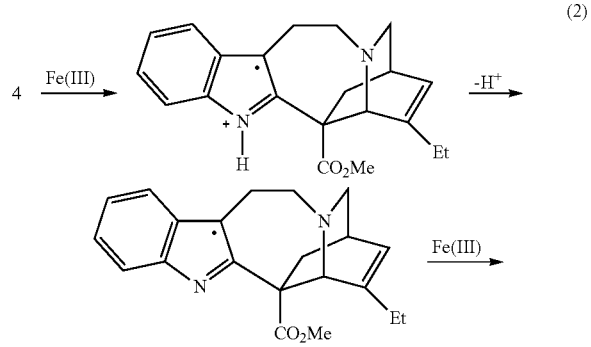

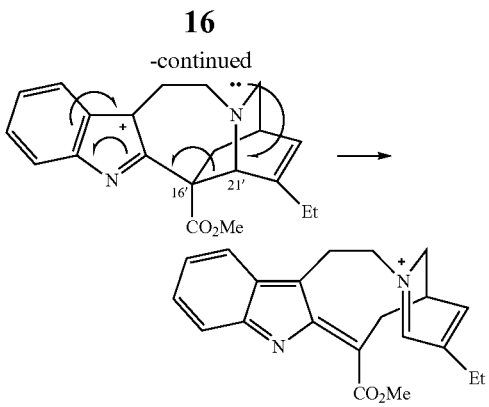

Each of the C-10' substituents was also incorporated into the corresponding vinblastine analogue using either the direct oxidation of the anhydrovinblastine derivative or the one-pot, two-step coupling and oxidation protocol. [Ishikawa at al., *J. Am. Chem. Soc.* 2009, 131:4904] Analogous to the clear delineation of the impact of cantharanthine C-10 substituents on the coupling reaction, the impact on the biological properties of the natural products was just as clear. [Voss et al., *Bioorg. Med. Chem. Lett.* 2009, 19:1245; Shao et al., *J. Nat. Prod.* 2009, 72:1170; Sheng et al., *Bioorg. Med. Chem. Lett.* 2008, 18:4602; Passarella et al., *Bioorg. Med. Chem.* 2008, 16:6269.]

The cytotoxic activity of a 10'-substituted vinca alkaloid analogue in the cell-based assays exhibited no apparent relationship to the electronic character of the substituents, but rather they exhibited activity that correlates with the size and shape of the C-10' substituent [R=F>H>Cl>Me, Br >>I, SMe (10-fold)>>CN (100-fold)]. Thus, small hydrophobic C-10' substituents are tolerated with several of the derivatives essentially matching the potency of the natural product (R=H vs Cl, Me, Br), but those bearing the larger (R=I, SMe, OMe) or more extended (R=CN) C-10' substituents proved to be 10-100 fold less potent.

Moreover, there proved to be a subtle distinction in the anhydrovinblastine and vinblastine series, reflecting not only the potential steric interactions at this site, but their interplay with the disposition of the 0-20' substituents. Thus, the anhydrovinblastine analogues bearing the small 0-10' substituents are also essentially equipotent with anhydrovinblastine itself (R=F>H, Cl, Br, Me), albeit 10-fold less active than vinblastine, but this series exhibited a greater tolerance for the larger substituents at this site (e.g., R=SMe and CN, but not I).

These two positions in the upper subunit of vinblastine (C-10' and C-20') represent the two ends of the upper portion of the T-shaped conformation of the tubulin-bound molecule that is deeply-imbedded in the protein. [Gigant et al., *Nature* 2005, 435:519] Presumably, altering the disposition of the C-20' ethyl substituent by converting C-20' to an $sp^2$ versus $sp^3$ center permits some, but not all of the derivatives with the larger C-10' substituents to bind tubulin effectively and exhibit comparable biological activity.

However it is believed, that the most striking observation to emerge from the studies was the behavior of 10'-fluorovinblastine (Compound 19b) and 10'-fluoroanhydrovinblastine (Compound 19a). Fluorine substitution at C-10', which minimally alters the characteristics of the natural products at this site, enhances the cytotoxic activity of the two analogues (about 8-fold), it represents a substituent that would be expected to block oxidative metabolism at this site and, most importantly, it significantly increased activity (ca. 8-fold for Compound 19b) against a vinblastine resistant cell line (HCT116/VM46). This latter feature, which is derived from overexpression of the cell surface drug efflux pump Pgp [Lampidis et al., *Biochemistry* 1997, 36:2679; Perego et al., *Cancer Res.* 2001, 61:6034], typically limits the effectiveness of vinblastine upon resistance relapse and the improved activity of Compound 19b suggests that it might represent an improved drug for both primary care or secondary treatment upon tumor reemergence.

Continued exploration of the deep-seated structural features of vinblastine contributing to its properties and their role is in progress and will be reported in due course. [Ishikawa et al., *J. Am. Chem. Soc.* 2006, 128:10596; Elliott et al., *J. Am. Chem. Soc.* 2006, 128:10589; Wilkie et al., *J. Am. Chem. Soc.* 2002, 124:11292.]

Chemical Syntheses

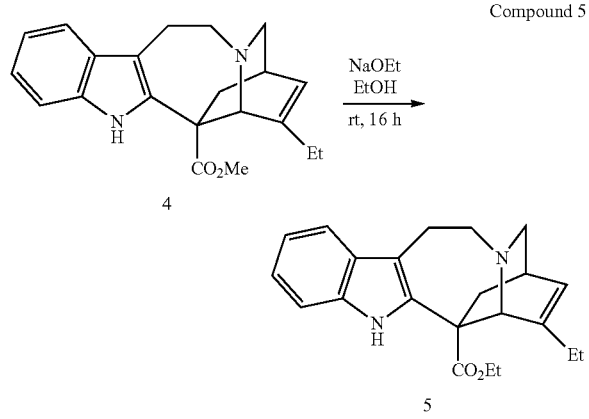

Catharanthine 4 (14.8 mg, 0.044 mmol) was dissolved in a solution of 1 M sodium ethoxide (NaOEt) (2 mL) and stirred for 16 hours at room temperature. Ethyl acetate (EtOAc) (5 mL) was added and the resulting mixture was washed with saturated aqueous NaCl (5 mL). The organic layer was dried over $Na_2SO_4$ and the solvent was removed under vacuum. Flash chromatography ($SiO_2$, 50% EtOAc—$CH_2Cl_2$) provided 5 (7.6 mg, 49% yield):

For 5: $^1$H NMR (400 MHz, $CDCl_3$) δ 7.69 (br s, NH, 1H), 7.49 (d, J=7.8 Hz, 1H), 7.24 (d, J=8.0 Hz, 1H), 7.15 (t, J=8.1 Hz, 1H), 7.11 (t, J=7.0 Hz, 1H), 5.94 (d, J=4.9 Hz, 1H), 4.23-4.16 (m, 2H), 3.60-3.56 (m, 1H), 3.41-3.38 (m, 1H), 3.33-3.27 (m, 1H), 2.94-2.92 (m, 1H), 2.87-2.85 (m, 3H), 2.74-2.71 (m, 2H), 2.37-2.32 (m, 1H), 2.19-2.14 (m, 1H), 1.78 (d, J=11.1 Hz, 1H), 1.27 (t, J=8.8 Hz, 3H), 1.07 (t, J=7.3 Hz, 3H); $^{13}$C NMR (100 MHz, $CDCl_3$) δ 176.6, 173.7, 136.5, 134.9, 129.0, 123.6, 121.8, 119.4, 118.2, 110.5, 110.4, 61.8, 55.2, 53.0, 49.1, 38.7, 30.7, 29.7, 26.5, 21.3, 14.1, 10.6; IR (film) $v_{max}$ 3232, 2969, 2360, 1736, 1459, 1235, 1085, 746 $cm^{-1}$; HRMS ESI-TOF m/z 351.2054 ($C_{22}H_{26}N_2O_2+H^+$, required 351.2067); $[α]^{23}_D$ +36 (c 0.14, $CHCl_3$).

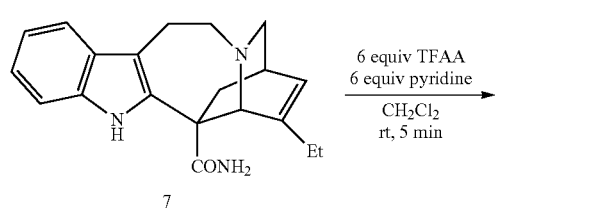

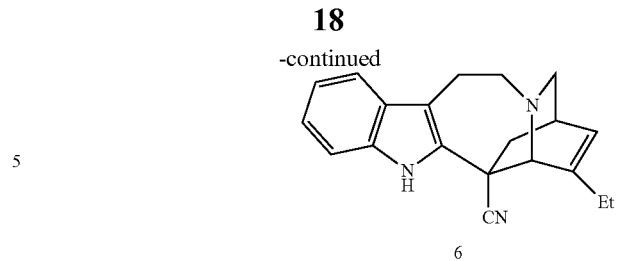

Compound 7 (62 mg, 0.19 mmol) was dissolved in anhydrous $CH_2Cl_2$ (2 mL) and pyridine (94 μL, 1.16 mmol) was added, followed by dropwise addition of trifluoroacetic anhydride (161 μL, 1.16 mmol). The reaction mixture was stirred for 5 minutes, then diluted with EtOAc (5 mL) and washed with saturated sodium bicarbonate (5 mL). The organic layer was dried over $Na_2SO_4$ and the solvent was removed under vacuum. Flash chromatography ($SiO_2$, 25% EtOAc-hexanes) provided 6 (27 mg, 46% yield).

For 6: $^1$H NMR (400 MHz, $CDCl_3$) δ 8.35 (br s, NH, 1H), 7.50 (d, J=7.8 Hz, 1H), 7.34 (d, J=8.0 Hz, 1H), 7.21 (t, J=7.4 Hz, 1H), 7.14 (d, J=7.2 Hz, 1H), 6.05 (d, J=5.3 Hz, 1H), 3.88 (s, 1H), 3.46-3.38 (m, 3H), 3.08 (d, J=8.2 Hz, 1H), 2.88-2.86 (m, 2H), 2.78-2.74 (m, 1H), 2.45-2.38 (m, 3H), 2.10 (d, J=13.4 Hz, 1H), 1.18 (t, J=7.3 Hz, 3H); $^{13}$C NMR (100 MHz, $CDCl_3$) δ 149.9, 134.2, 132.3, 129.3, 122.34, 122.30, 121.9, 119.9, 118.2, 110.8 (2C), 64.0, 52.6, 47.5, 44.2, 41.1, 29.6, 27.1, 20.4, 10.4; IR (film) $v_{max}$ 3347, 2849, 2231, 1457, 1123, 906, 727 $cm^{-1}$; HRMS ESI-TOF m/z 304.1819 ($C_{20}H_{21}N_3+H^+$, required 304.1808); $[α]^{23}_D$ −0.11 (c 0.46, $CHCl_3$).

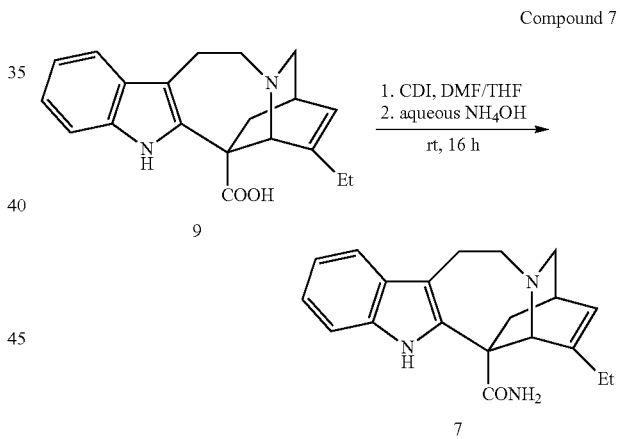

Compound 9 (81 mg, 0.25 mmol) was dissolved in anhydrous DMF (500 μL) and anhydrous THF (2.5 mL). 1,1'-Carbonyldiimidazole (203 mg, 1.25 mmol) was added and the resulting mixture was stirred for 45 min at room temperature. The solution was cooled to 0° C. before the addition of $NH_4OH$ (3 mL). The resulting mixture was warmed to room temperature and stirred for 16 hours. Water was added (5 mL) and the mixture was extracted with EtOAc (3×10 mL). The organic layer was dried over $Na_2SO_4$ and the solvent was removed under vacuum. Flash chromatography ($SiO_2$, 5:47:47 MeOH/EtOAc/$CH_2Cl_2$) provided 7 (52 mg, 65% yield).

For 7: $^1$H NMR (400 MHz, $CDCl_3$) δ 7.99 (br s, NH, 1H), 7.24 (d, J=8.1 Hz, 1H), 7.50 (d, J=7.4 Hz, 1H), 7.16 (t, J=6.9 Hz, 1H), 5.96 (d, J=5.5 Hz, 1H), 5.60 (br s, 2H), 3.95 (s, 1H), 3.62-3.56 (m, 1H), 3.40-3.35 (m, 1H), 3.32-3.28 (m, 1H), 3.02-2.96 (m, 1H), 2.85-2.81 (m, 2H), 2.76-2.74 (m, 1H), 2.38-2.24 (m, 1H), 2.24 (d, J=5.5 Hz, 1H), 2.04-1.99 (m, 2H), 1.62 (d, J=12.67 Hz, 1H), 1.08 (t, J=7.3 Hz, 3H); $^{13}$C NMR (100 MHz, CDCl$_3$) δ 174.9, 148.0, 137.1, 135.4, 128.5, 123.2, 122.1, 119.3, 118.2, 111.2, 110.4, 63.8, 55.5, 53.1, 49.4, 36.5, 30.39, 26.93, 21.5, 10.5; IR (film) v$_{max}$ 3291, 2962, 1676, 1460, 1363, 1105, 745 cm$^{-1}$; HRMS ESI-TOF m/z 322.1924 (C$_{20}$H$_{23}$N$_3$O+H$^+$, required 322.1914); [α]$^{23}$$_D$ +0.48 (c 0.17, CHCl$_3$).

Compound 8

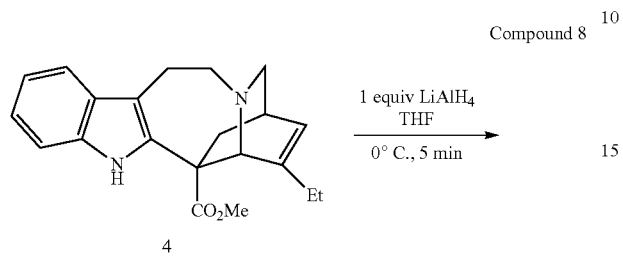

Catharanthine 4 (84 mg, 0.25 mmol) was dissolved in anhydrous THF (4 mL) and cooled to 0° C. LiAlH$_4$ (9.2 mg, 0.25 mmol) was added portion-wise to the solution and the resulting suspension was stirred for 5 minutes. The reaction was carefully quenched by addition of a solution of saturated aqueous NH$_4$Cl (5 mL) and extracted with EtOAc (10 mL). The organic layer was dried over Na$_2$SO$_4$ and the solvent was removed under vacuum. Flash chromatography (SiO$_2$, 10% MeOH-EtOAc) provided 8 (28 mg, 37% yield).

For 8: $^1$H NMR (400 MHz, CDCl$_3$) δ 9.51 (s, 1H), 7.83 (br s, 1H), 7.52 (d, J=7.8 Hz, 1H), 7.25 (d, J=8.0 Hz, 1H), 7.16 (t, J=6.9 Hz, 1H), 7.12 (t, J=7.9 Hz, 1H), 5.99 (d, J=7.8 Hz, 1H), 3.95 (s, 1H), 3.57-3.52 (m, 1H), 3.45-3.35 (m, 2H), 3.00 (d, J=8.6 Hz, 1H), 2.94-2.88 (m, 2H), 2.80-2.79 (m, 1H), 2.56 (dt, J=13.0, 3.0 Hz, 1H), 2.37-2.32 (m, 1H), 2.11-2.05 (m, 1H), 1.77 (dd, J=13.0, 2.1 Hz, 1H), 1.08 (t, J=7.3 Hz, 3H); $^{13}$C NMR (100 MHz, CDCl$_3$) δ 201.4, 148.2, 135.2, 134.0, 129.0, 124.3, 123.0, 119.5, 118.1, 112.7, 110.6, 62.1, 59.4, 53.2, 49.4, 35.3, 30.5, 26.8, 21.1, 10.6; IR (film) v$_{max}$ 3383, 3051, 2843, 1708, 1458, 740 cm$^{-1}$; HRMS ESI-TOF m/z 307.1798 (C$_{20}$H$_{22}$N$_2$O+H$^+$, required 307.1805); [α]$^{23}$$_D$ +0.52 (c 0.48, CHCl$_3$).

Compound 9

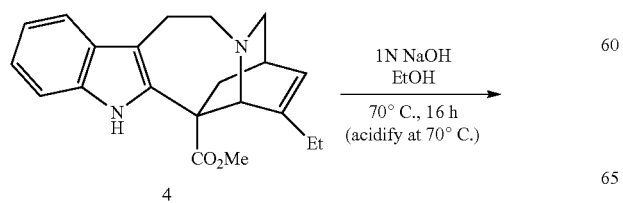

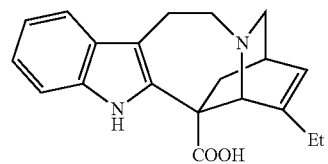

Catharanthine 4 (85 mg, 0.25 mmol) was dissolved in absolute EtOH (2 mL) and a solution of 1 N NaOH (3 mL) was added. The resulting mixture was warmed to 70° C. for 16 hours. The reaction mixture was cooled to 0° C. before it was acidified by dropwise addition of 2 N HCl. The mixture was extracted into EtOAc (3×15 mL). The organic layer was dried over Na$_2$SO$_4$ and the solvent was removed under vacuum. Flash chromatography (SiO$_2$, 1:2:2 MeOH/EtOAc/CH$_2$Cl$_2$) provided 9 (56 mg, 70% yield). Spectral data was as previously reported. [Kutney et al., *Helv. Chim. Acta* 1978, 61:690.]

Compound 10

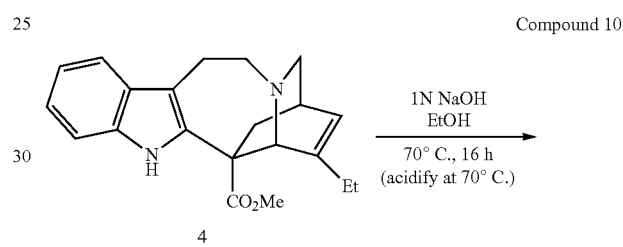

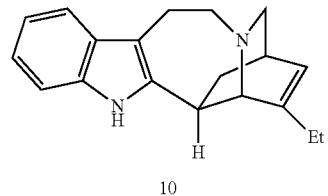

Catharanthine 4 (85 mg, 0.25 mmol) was dissolved in absolute EtOH (2 mL) and a solution of 1 N NaOH (3 mL) was added. The resulting mixture was warmed to 70° C. for 16 hours. The reaction mixture was acidified by dropwise addition of 2 N HCl. The mixture was extracted into EtOAc (3×15 mL). The organic layer was dried over Na$_2$SO$_4$ and the solvent was removed under vacuum. Flash chromatography (SiO$_2$, 1:2:2 MeOH/EtOAc/CH$_2$Cl$_2$) provided 10 (59 mg, 85% yield). Spectral data was as previously reported. [Kutney at al., *Helv. Chim. Acta* 1978, 61:690.]

Compound 11

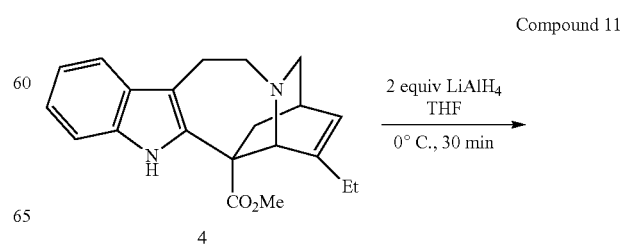

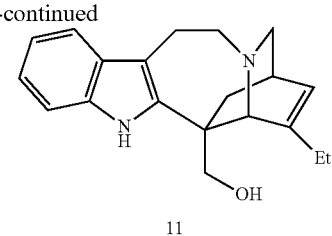

11

Catharanthine 4 (44.6 mg, 0.133 mmol) was added to a suspension of LiAlH$_4$ (9.9 mg, 0.27 mmol) in THF (2 mL) at 0° C. and the solution was stirred for 10 minutes. The reaction was carefully quenched by addition of a solution of saturated aqueous NH$_4$Cl (5 mL) and extracted with EtOAc (10 mL). The organic layer was dried over Na$_2$SO$_4$ and the solvent was removed under vacuum. Flash chromatography (SiO$_2$, 15% MeOH-EtOAc) provided 11 (32 mg, 77% yield).

For 11: $^1$H NMR (400 MHz, CDCl$_3$) δ 9.28 (br s, NH, 1H), 7.48-7.46 (m, 1H), 7.31-7.28 (m, 1H), 7.15-7.13 (m, 2H), 5.89 (d, J=7.1 Hz, 1H), 3.68 (d, J=11.1 Hz, 1H), 3.65 (s, 1H), 3.57 (d, J=11.1 Hz, 1H), 3.32-3.29 (m, 2H), 3.17-3.14 (m, 2H), 2.93-2.90 (m, 1H), 2.84-2.82 (m, 1H), 2.72-2.63 (m, 2H), 2.50-2.44 (m, 1H), 2.28-2.20 (m, 1H), 1.63 (d, J=12.3 Hz, 1H), 1.49 (d, J=12.8 Hz, 1H), 1.15 (t, J=7.3 Hz, 3H); $^{13}$C NMR (100 MHz, CDCl$_3$) δ 176.6, 150.1, 134.7, 128.4, 121.4, 120.9, 118.9, 118.1, 110.6, 109.7, 68.8, 62.4, 52.6, 50.7, 47.7, 36.3, 30.2, 26.7, 20.6, 10.3; IR (film) $v_{max}$ 3352, 2926, 1736, 1461, 1240, 1045, 741 cm$^{-1}$; HRMS ESI-TOF m/z 309.1971 (C$_{20}$H$_{24}$N$_2$O+H, required 309.1961); $[α]^{23}_D$ +0.07 (c 0.83, MeOH).

Compound 12

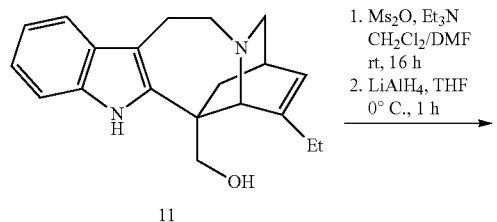

A solution of compound 11 (79 mg, 0.26 mmol) in anhydrous 1:1 CH$_2$Cl$_2$/DMF (2.5 mL) at 0° C. was treated with methanesulfonyl anhydride (54 mg, 0.31 mmol) and Et$_3$N (109 μL, 0.78 mmol). The resulting reaction mixture was allowed to warm to room temperature and stirred for 16 hours. The solvent was removed under reduced pressure and the residue was purified by flash chromatography (SiO$_2$, 10% MeOH-EtOAc). A solution of LiAlH$_4$ (3.3 mg, 0.088 mmol) in anhydrous THF (440 μL) was treated with the mesylate product (17 mg, 0.044 mmol) at 0° C. The reaction mixture was stirred for 1 hour before careful quench with a drop of an aqueous solution of NH$_4$Cl. EtOAc (2 mL) was added and the solution was washed with saturated aqueous NH$_4$Cl (1 mL). The organic layer was dried over Na$_2$SO$_4$ and the solvent was removed under vacuum. Flash chromatography (SiO$_2$, 10% MeOH-EtOAc) provided 12 (27 mg, 32% yield).

For 12: $^1$H NMR (400 MHz, CDCl$_3$) δ 7.97 (br s, NH, 1H), 7.48 (d, J=8.3 Hz, 1H), 7.30 (d, J=7.7 Hz, 1H), 7.17-7.09 (m, 2H), 5.89 (d, J=6.8 Hz, 1H), 3.49-3.43 (m, 2H), 3.37-3.29 (m, 1H), 2.96-2.87 (m, 2H), 2.73-2.71 (m, 1H), 2.54-2.45 (m, 1H), 2.20-2.11 (m, 1H), 1.86 (d, J=10.8 Hz, 2H), 1.53 (d, J=11.8 Hz, 2H), 1.29 (s, 3H), 1.13 (t, J=7.3 Hz, 3H); $^{13}$C NMR (100 MHz, CDCl$_3$) δ 142.7, 134.1, 130.1, 128.9, 121.4, 119.4, 118.1 (20), 110.2, 109.1, 65.6, 53.0, 47.7, 41.54, 41.52, 30.4, 27.8, 27.2, 23.5, 10.3; IR (film) $v_{max}$ 2928, 1461, 1261, 1100, 730 cm$^{-1}$; HRMS ESI-TOF m/z 293.2017 (C$_{20}$H$_{24}$N$_2$+H$^+$, required 293.2012); $[α]^{23}_D$ +17 (c 0.26, CHCl$_3$).

Compound 13

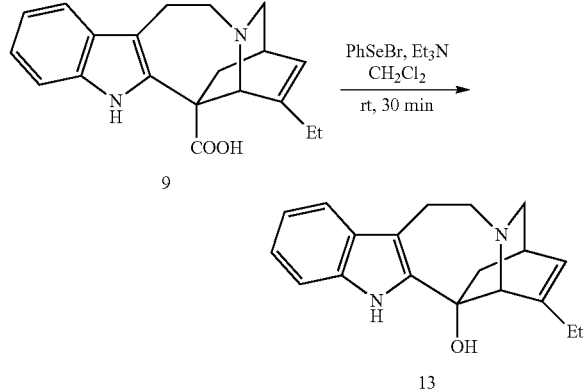

A solution of phenylselenyl bromide (22 mg, 0.09 mmol) in CH$_2$Cl$_2$ (0.5 mL) was added dropwise to a solution of 9 (20 mg, 0.06 mmol) and Et$_3$N (18 μL) in CH$_2$Cl$_2$ (1.5 mL) at room temperature under an atmosphere of Ar. After 30 minutes, the mixture was diluted with CH$_2$Cl$_2$ (5 mL) and washed with H$_2$O (2 mL). The organic layer was dried over Na$_2$SO$_4$ and the solvent was removed under vacuum. Flash chromatography (SiO$_2$, 10% MeOH-EtOAc) provided 13 (6 mg, 29% yield). Spectral data was as previously reported. [Kutney et al., *Helv. Chim. Acta* 1978, 61:690.]

Compound 5a

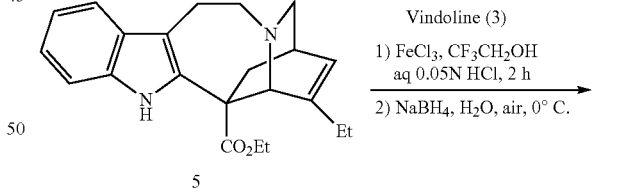

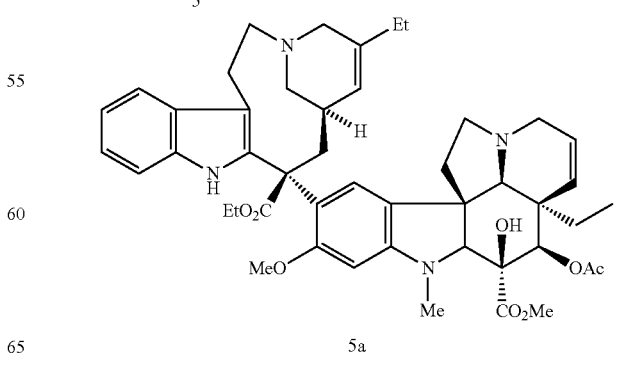

5a

Iron(III) chloride hexahydrate (42 mg, 0.16 mmol) was added to a solution of vindoline (3, 14 mg, 0.031 mmol) and 5 (11 mg, 0.031 mmol) in $CF_3CH_2OH$ (0.12 mL), aqueous 0.1 N HCl (0.59 mL) and $H_2O$ (0.59 mL) at 25° C. under Ar. The reaction mixture was stirred for 2 hours at 25° C. The solution was cooled to 0° C. and a solution of $NaBH_4$ (1.2 mg, 0.031 mmol) in $H_2O$ (0.1 mL) was added. The resulting mixture was stirred for 30 minutes before being quenched by the addition of 30% aqueous $NH_4OH$ (0.5 mL). The mixture was extracted with 10% MeOH in $CH_2Cl_2$. The combined organic layer was dried over anhydrous $Na_2SO_4$ and concentrated under reduced pressure. Purification by flash column chromatography ($SiO_2$, 0-10% MeOH/EtOAc) afforded 5a (22 mg, 82%).

For 5a: $^1$H NMR (500 MHz, $CDCl_3$) δ 9.81 (br s, 1H), 8.06 (s, 1H), 7.53-7.50 (m, 1H), 7.18-7.10 (m, 3H), 6.61-6.60 (m, 1H), 6.12 (s, 1H), 5.85 (dd, J=10.0, 3.5 Hz, 1H), 5.49-5.47 (m, 2H), 5.28 (d, J=9.0 Hz, 1H), 4.10-4.01 (m, 2H), 3.81 (s, 3H), 3.80 (s, 1H), 3.79 (s, 3H), 3.72 (s, 1H), 3.61 (s, 1H), 3.53-3.50 (m, 1H), 3.39-3.35 (m, 2H), 3.31-3.26 (m, 2H), 3.22-3.19 (m, 1H), 3.09-2.94 (m, 2H), 2.84-2.78 (m, 1H), 2.71 (s, 3H), 2.65 (s, 1H), 2.61-2.57 (m, 1H), 2.47-2.40 (m, 2H), 2.11 (s, 3H), 1.96-1.91 (m, 1H), 1.87-1.85 (m, 1H), 1.83-1.79 (m, 2H), 1.73-1.68 (m, 1H), 1.42-1.36 (m, 1H), 1.34-1.30 (m, 1H), 1.13 (t, J=7.2 Hz, 3H), 0.99 (t, J=7.4 Hz, 3H), 0.94 (t, J=7.4 Hz, 3H); IR (film) $v_{max}$ 3467, 2963, 1738, 1458, 1226, 1040, 748 cm$^1$; HRMS ESI-TOF m/z 807.4351 ($C_{47}H_{58}N_4O_8$+H$^+$, required 807.4255); [α]$^{23}$ +36 (c 0.38, $CHCl_3$).

10% MeOH in $CH_2Cl_2$. The combined organic layer was dried over anhydrous $Na_2SO_4$ and concentrated under reduced pressure. PTLC ($SiO_2$, $Et_3$N:MeOH:EtOAc=3:3:97) afforded 5b (4 mg, 26%).

For 5b: $^1$H NMR (500 MHz, $CDCl_3$) δ 8.07 (s, 1H), 7.52 (d, J=7.66 Hz, 1H), 7.17-7.08 (m, 3H), 6.62 (s, 1H), 6.11 (s, 1H), 5.86-5.83 (m, 1H), 5.48 (s, 1H), 5.28 (d, J=9.9 Hz, 1H), 4.07-4.01 (m, 2H), 3.94 (t, J=14.7 Hz, 1H), 3.80 (s, 3H), 3.79 (s, 1H), 3.78 (s, 3H), 3.73 (s, 2H), 3.67-3.61 (m, 2H), 3.41-3.36 (m, 2H), 3.30-3.28 (m, 2H), 3.15-3.13 (m, 2H), 2.83-2.80 (m, 3H), 2.71 (s, 3H), 2.65 (s, 1H), 2.46-2.42 (m, 2H), 2.32-2.30 (m, 2H), 2.20-2.15 (m, 1H), 2.10 (s, 3H), 1.88-1.77 (m, 2H), 1.50-1.40 (m, 2H), 1.33-1.30 (m, 2H), 1.11 (t, J=6.4 Hz, 3H), 0.88 (t, J=7.3 Hz, 3H), 0.80 (t, J=7.2 Hz, 3H); IR (film) $v_{max}$ 3467, 2927, 1737, 1226, 1039, 735 cm$^{-1}$; HRMS ESI-TOF m/z 825.4422 ($C_{47}H_{60}N_4O_9$+H$^+$, required 825.4433); [α]$^{23}$$_D$ +37 (c 0.14, $CHCl_3$).

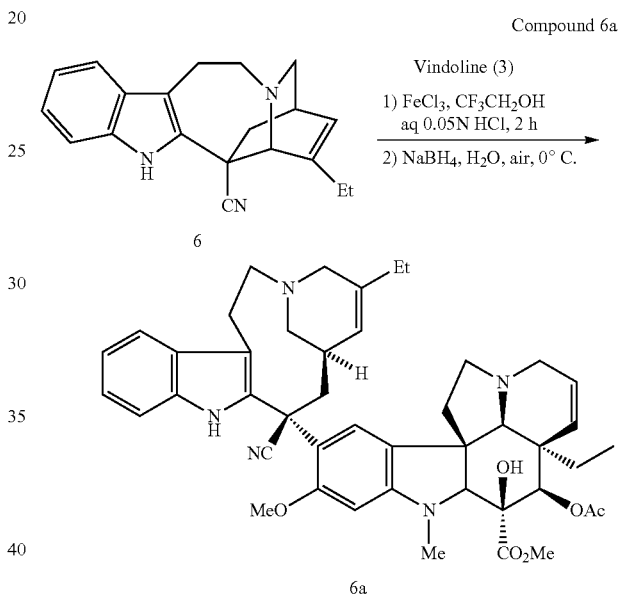

Compound 6a

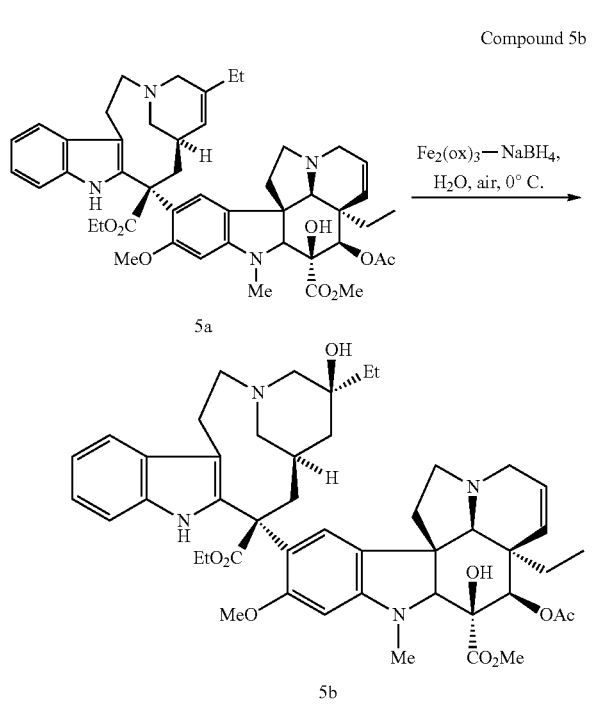

Compound 5b

Iron(III) chloride hexahydrate (53 mg, 0.20 mmol) was added to a solution of vindoline (3, 18 mg, 0.04 mmol) and 6 (12 mg, 0.04 mmol) in $CF_3CH_2OH$ (0.14 mL), aqueous 0.1 N HCl (0.74 mL) and $H_2O$ (0.74 mL) at 25° C. under Ar. The reaction mixture was stirred for 2 hours at 25° C. The solution was cooled to 0° C. and a solution of $NaBH_4$ (1.5 mg, 0.04 mmol) in $H_2O$ (0.1 mL) was added. The resulting mixture was stirred for 30 minutes before being quenched by the addition of 30% aqueous $NH_4OH$ (0.5 mL). The mixture was extracted with 10% MeOH in $CH_2Cl_2$. The combined organic layer was dried over anhydrous $Na_2SO_4$ and concentrated under reduced pressure. Purification by flash column chromatography ($SiO_2$, 0-10% MeOH/EtOAc) afforded 6a (57 mg, 95%).

A solution of iron(III) oxalate hexahydrate (90 mg, 0.19 mmol) in $H_2O$ (80 mL) was cooled to 0° C. and air was bubbled through the mixture for 10 minutes. A solution of compound 5a (15 mg, 0.019 mmol) dissolved in $CF_3CH_2OH$ (0.9 mL), aqueous 0.1 N HCl (0.45 mL) and $H_2O$ (0.45 mL) was transferred by pipette to this aqueous iron(III) oxalate solution and $NaBH_4$ (14 mg, 0.37 mmol) in $H_2O$ (1 mL) was added to the mixture at 0° C. The resulting mixture was stirred for 30 minutes before being quenched by the addition of 30% aqueous $NH_4OH$ (3 mL). The mixture was extracted with For 6a: $^1$H NMR (600 MHz, $CDCl_3$) δ 7.53 (br s, 1H), 7.16-6.99 (m, 3H), 6.89 (d, J=8.2 Hz, 1H), 6.29 (dd, J=8.2, 2.2 Hz, 1H), 6.07 (d, J=2.2 Hz, 1H), 5.94-5.89 (m, 1H), 5.85 (dd, J=10.2, 4.9 Hz, 1H), 5.45 (s, 2H), 5.27-5.23 (m, 2H), 3.79 (s, 1H), 3.787 (s, 3H), 3.782 (s, 3H), 3.75 (s, 1H), 3.66 (s, 1H), 3.61-3.56 (m, 2H), 3.51-3.47 (m, 1H), 3.44-3.40 (m, 1H), 3.32 (s, 1H), 3.13-3.10 (m, 1H), 2.68 (s, 1H), 2.67 (s, 3H), 2.66 (s, 2H), 2.55-2.49 (m, 1H), 2.41-2.26 (m, 2H), 2.17 (s, 2H), 2.09 (s, 1H), 2.07 (s, 3H), 1.66-1.62 (m, 2H), 1.27-1.25 (m, 2H), 0.88 (t, J=5.3 Hz, 3H), 0.49 (t, J=7.4 Hz, 3H); IR (film) $v_{max}$ 3454, 2961, 1737, 1230, 1039, 732 cm$^{-1}$; HRMS ESI-TOF m/z 760.4089 ($C_{45}H_{53}N_5O_6$+H$^+$, required 760.4068); $[\alpha]^{23}_D$ +9 (c 0.14, CHCl$_3$).

Compound 6b

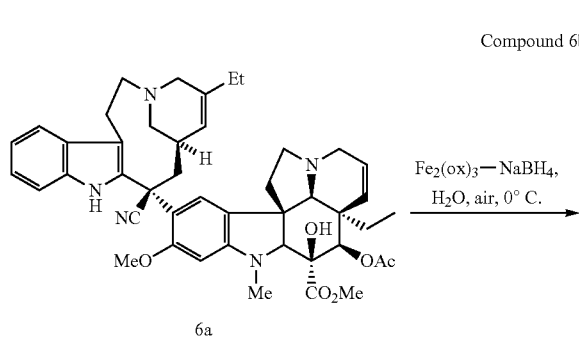

6a $\xrightarrow{\text{Fe}_2(\text{ox})_3-\text{NaBH}_4,\ \text{H}_2\text{O, air, 0}°\text{C.}}$

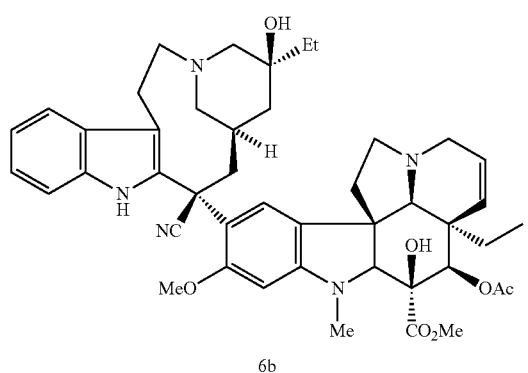

6b

A solution of iron(III) oxalate hexahydrate (122 mg, 0.25 mmol) in H$_2$O (100 mL) was cooled to 0° C. and air was bubbled through the mixture for 10 minutes. A solution of compound 6a (19 mg, 0.025 mmol) dissolved in CF$_3$CH$_2$OH (0.12 mL), aqueous 0.1 N HCl (0.6 mL) and H$_2$O (0.6 mL) was transferred by pipette to this aqueous iron(III) oxalate solution and NaBH$_4$ (19 mg, 0.5 mmol) in H$_2$O (1.2 mL) was added to the mixture at 0° C. The resulting mixture was stirred for 30 minutes before being quenched by the addition of 30% aqueous NH$_4$OH (3 mL). The mixture was extracted with 10% MeOH in CH$_2$Cl$_2$. The combined organic layer was dried over anhydrous Na$_2$SO$_4$ and concentrated under reduced pressure. PTLC (SiO$_2$, Et$_3$N:MeOH:EtOAc=3:3:97) afforded 6b (2.9 mg, 15%).

For 6b: $^1$H NMR (500 MHz, CDCl$_3$) δ 8.22 (br s, 1H), 7.55-7.51 (m, 1H), 7.23-7.21 (m, 3H), 7.08-7.07 (m, 1H), 6.98 (d, J=6.1 Hz, 1H), 6.14 (s, 1H), 6.05 (s, 1H), 5.96-5.91 (m, 1H), 5.82-5.81 (m, 1H), 5.51-5.39 (m, 2H), 5.29 (s, 1H), 5.24 (d, J=10.7 Hz, 1H), 5.18 (s, 1H), 4.06 (t, J=6.7 Hz, 1H), 3.83 (s, 1H), 3.81 (s, 3H), 3.80 (s, 3H), 3.68-3.63 (m, 1H), 3.58-3.56 (m, 2H), 3.41 (d, J=6.5 Hz, 1H), 3.38-3.33 (m, 2H), 3.15-3.05 (m, 1H), 2.85-2.81 (m, 1H), 2.74 (s, 3H), 2.68 (s, 1H), 2.65 (s, 1H), 2.53-2.46 (m, 3H), 2.42-2.40 (m, 1H), 2.08 (s, 3H), 2.02-2.00 (m, 1H), 1.71-1.66 (m, 1H), 1.62-1.58 (m, 1H), 1.42-1.36 (m, 2H), 0.88 (t, J=7.3 Hz, 3H), 0.75 (t, J=7.3 Hz, 3H); IR (film) v$_{max}$ 3455, 2927, 1740, 1615, 1459, 1241, 1040, 740 cm$^{-1}$; HRMS ESI-TOF m/z 778.4182 ($C_{45}H_{55}N_5O_7$+H$^+$, required 778.7174); $[\alpha]^{23}_D$ −18 (c 0.17, CHCl$_3$).

Compound 7a

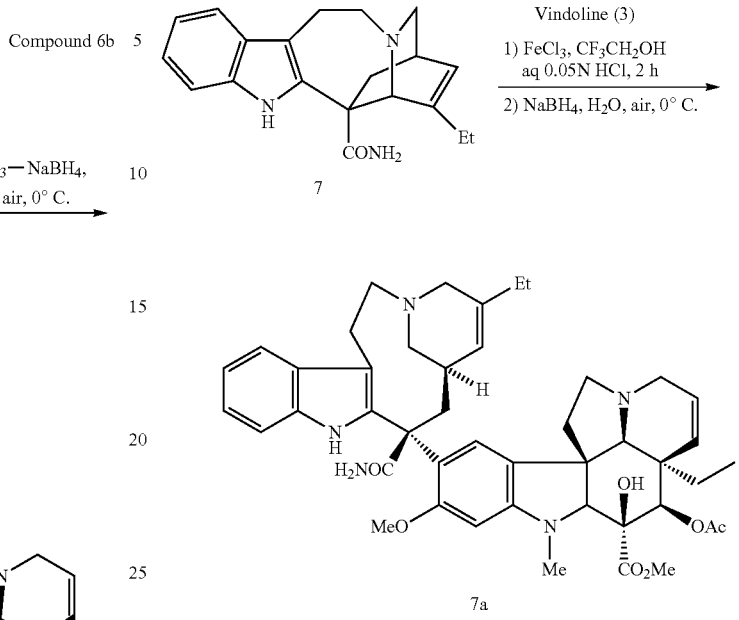

Iron(III) chloride hexahydrate (61 mg, 0.22 mmol) was added to a solution of vindoline (3, 20 mg, 0.045 mmol) and 7 (14 mg, 0.045 mmol) in CF$_3$CH$_2$OH (0.17 mL), aqueous 0.1 N HCl (0.84 mL) and H$_2$O (0.84 mL) at 25° C. under Ar. The reaction mixture was stirred for 2 hours at 25° C. The solution was cooled to 0° C. and a solution of NaBH$_4$ (1.7 mg, 0.045 mmol) in H$_2$O (0.1 mL) was added. The resulting mixture was stirred for 30 minutes before being quenched by the addition of 30% aqueous NH$_4$OH (0.5 mL). The mixture was extracted with 10% MeOH in CH$_2$Cl$_2$. The combined organic layer was dried over anhydrous Na$_2$SO$_4$ and concentrated under reduced pressure. Purification by flash column chromatography (SiO$_2$, 0-10% MeOH/EtOAc) afforded 7a (29 mg, 79%).

For 7a: $^1$H NMR (500 MHz, CDCl$_3$) δ 9.84 (br s, 1H), 8.37 (s, 1H), 7.52 (d, J=7.7 Hz, 1H), 7.21-7.09 (m, 3H), 6.73 (br s, 1H), 6.14 (s, 1H). 5.83 (dd, J=9.3, 4.4 Hz, 1H), 5.47 (br s, 2H), 5.45 (s, 2H), 5.26 (d, J=9.7 Hz, 1H), 5.22 (s, 1H), 3.82 (s, 3H), 3.79 (s, 3H), 3.49-3.29 (m, 6H), 3.19-3.11 (m, 2H), 2.99-2.97 (m, 1H), 2.96-2.80 (m, 2H), 2.79 (s, 1H), 2.71 (s, 3H), 2.63 (s, 1H), 2.46-2.42 (m, 2H), 2.22-2.15 (m, 1H), 2.10 (s, 3H), 1.96-1.89 (m, 2H), 1.77-1.68 (m, 2H), 1.67-1.58 (m, 1H), 1.42-1.34 (m, 1H), 0.98 (t, J=7.5 Hz, 3H), 0.93 (t, J=7.4 Hz, 3H); IR (film) v$_{max}$ 3366, 2963, 1742, 1674, 1241, 1040, 748 cm$^{-1}$; HRMS ESI-TOF m/z 778.4165 ($C_{45}H_{55}N_5O_7$+H$^+$, required 778.4174); $[\alpha]^{23}_D$ +23 (c 0.82, CHCl$_3$).

Compound 7b

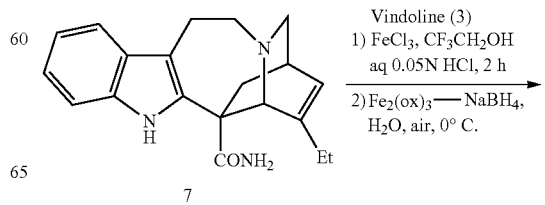

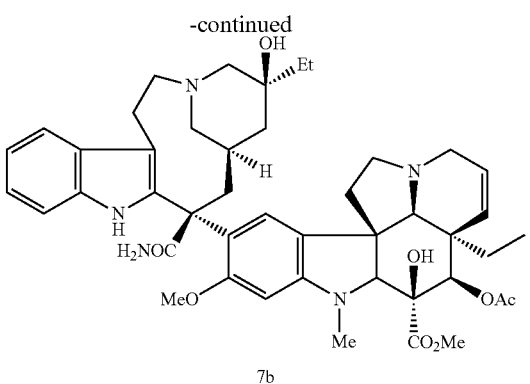

7b

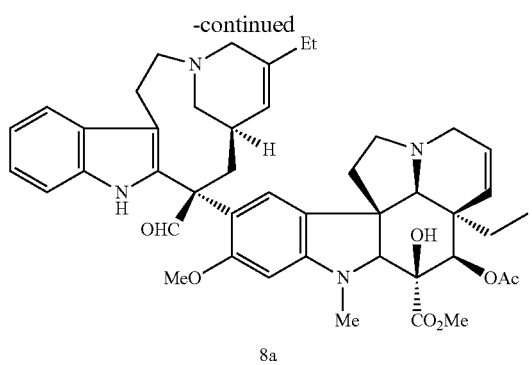

8a

Iron(III) chloride hexahydrate (64 mg, 0.24 mmol) was added to a solution of vindoline (3, 22 mg, 0.0483 mmol) and 7 (15.3 mg, 0.048 mmol) in $CF_3CH_2OH$ (0.18 mL), aqueous 0.1 N HCl (0.89 mL) and $H_2O$ (0.89 mL) at 25° C. under Ar. The reaction mixture was stirred for 2 hours at 25° C. Meanwhile, in a separate flask, a solution of iron(III) oxalate hexahydrate (230 mg, 0.48 mmol) in $H_2O$ (190 mL) was cooled to 0° C. and air was bubbled through the mixture for 10 minutes. The coupling solution was transferred by pipette to this aqueous iron (III) oxalate solution and $NaBH_4$ (36 mg, 0.94 mmol) in $H_2O$ (2.0 mL) was added to the mixture at 0° C. The resulting mixture was stirred for 30 minutes before being quenched by the addition of 30% aqueous $NH_4OH$ (3 mL). The mixture was extracted with 10% MeOH in $CH_2Cl_2$. The combined organic layer was dried over anhydrous $Na_2SO_4$ and concentrated under reduced pressure. PTLC ($SiO_2$, $Et_3N$: MeOH:EtOAc=3:3:97) afforded 7b (4.2 mg, 11%).

For 7b: $^1H$ NMR (500 MHz, $CDCl_3$) δ 8.64 (br s, 1H), 7.48 (d, J=7.8 Hz, 1H), 7.28-7.13 (m, 3H), 7.08 (t, J=7.5 Hz, 1H), 6.87-6.85 (br s, 1H), 6.13 (s, 1H), 5.82 (dd, J=10.3, 4.2 Hz, 1H), 5.45 (s, 1H), 5.23 (d, J=10.4 Hz, 1H), 4.25-4.17 (m, 2H), 4.06 (dd, J=6.77 Hz, 1H), 3.79 (s, 6H), 3.76 (s, 1H), 3.67-3.62 (m, 2H), 3.55-3.50 (m, 2H), 3.37 (dd, J=16.1, 5.4 Hz, 1H), 3.31-3.20 (m, 2H), 3.08-3.05 (m, 2H), 2.95-2.91 (m, 2H), 2.81 (d, J=16.3 Hz, 1H), 2.72 (s, 3H), 2.61 (s, 1H), 2.46-2.42 (m, 2H), 2.25-2.19 (m, 2H), 2.09 (s, 3H), 2.07-2.00 (m, 2H), 1.77-1.69 (m, 1H), 1.56-1.53 (m, 1H), 1.38-1.35 (m, 1H), 1.31-1.30 (m, 2H), 0.92 (t, J=8.7 Hz, $^3H$), 0.86 (t, J=7.3 Hz, 3H); IR (film) $v_{max}$ 3415, 2962, 1740, 1668, 1612, 1228, 1035, 732 $cm^{-1}$; HRMS ESI-TOF m/z 796.4275 ($C_{45}H_{57}N_5O_8$+$H^+$, required 796.4280); $[α]^{23}D$ +25 (c 0.15, $CHCl_3$).

Iron(III) chloride hexahydrate (41 mg, 0.15 mmol) was added to a solution of vindoline (3, 14 mg, 0.03 mmol) and 8 (9.2 mg, 0.03 mmol) in $CF_3CH_2OH$ (0.11 mL), aqueous 0.1 N HCl (0.57 mL) and $H_2O$ (0.57 mL) at 25° C. under Ar. The reaction mixture was stirred for 2 hours at 25° C. The solution was cooled to 0° C. and a solution of $NaBH_4$ (1.1 mg, 0.03 mmol) in $H_2O$ (0.1 mL) was added. The resulting mixture was stirred for 30 minutes before being quenched by the addition of 30% aqueous $NH_4OH$ (0.5 mL). The mixture was extracted with 10% MeOH in $CH_2Cl_2$. The combined organic layer was dried over anhydrous $Na_2SO_4$ and concentrated under reduced pressure. Purification by flash column chromatography ($SiO_2$, 0-10% MeOH/EtOAc) afforded 8a (30 mg, 49%).

For 8a: $^1H$ NMR (600 MHz, $C_6D_6$) δ 9.59 (s, 1H), 8.99 (s, 1H), 7.51 (d, J=8.0 Hz, 1H), 7.13-7.03 (m, 3H), 6.61 (s, 1H), 6.17 (s, 1H), 5.90 (dd, J=9.9, 3.9 Hz, 1H), 5.47 (s, 1H), 5.27 (d, J=10.2 Hz, 1H), 4.06 (d, J=6.7 Hz, 1H), 4.03 (s, 1H), 3.84 (s, 1H), 3.80 (s, 3H), 3.76 (s, 3H), 3.67-3.62 (m, 2H), 3.50-3.48 (m, 1H), 3.41-3.39 (m, 2H), 3.28-3.26 (m, 2H), 3.10-3.04 (m, 2H), 2.90-2.87 (m, 1H), 2.73 (s, 1H), 2.67 (s, 3H), 2.58-2.53 (m, 2H), 2.30-2.25 (m, 3H), 2.10 (s, 3H), 1.96 (s, 1H), 1.95-1.93 (m, 2H), 1.85-1.82 (m, 1H), 1.61-1.58 (m, 1H), 1.39-1.35 (m, 1H), 1.04 (t, J=7.3 Hz, 3H), 0.78 (t, J=7.2 Hz, 3H); IR (film) $v_{max}$ 3456, 2930, 1738, 1240, 1041, 737 $cm^{-1}$; HRMS ESI-TOF m/z 763.4066 ($C_{45}H_{54}N_4O_7$+$H^+$, required 763.4065); $[α]^{23}_D$ +19 (c 0.32, $CHCl_3$).

Compound 8a

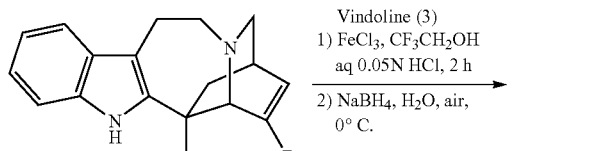

8

Vindoline (3)
1) $FeCl_3$, $CF_3CH_2OH$
aq 0.05N HCl, 2 h
2) $NaBH_4$, $H_2O$, air, 0° C.

Compound 11b

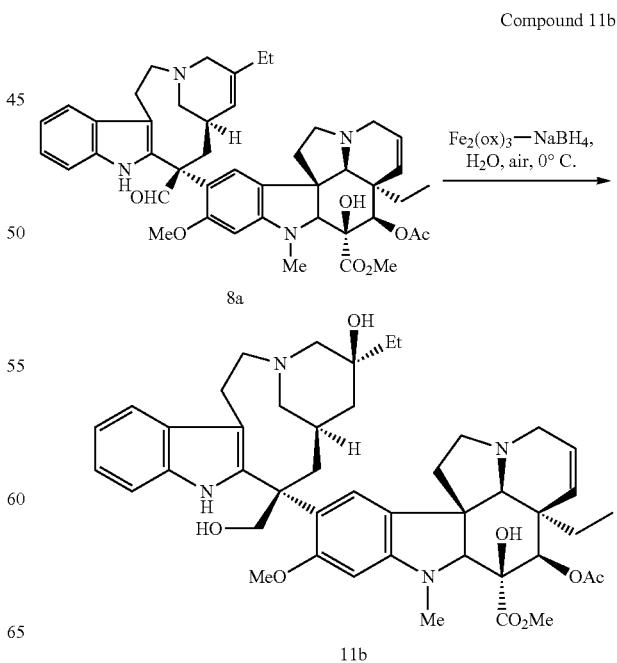

11b

A solution of iron(III) oxalate hexahydrate (38 mg, 0.08 mmol) in $H_2O$ (33 mL) was cooled to 0° C. and air was bubbled through the mixture for 10 minutes. A solution of compound 8a (6 mg, 7.7 μmol) dissolved in $CF_3CH_2OH$ (38 μL), aqueous 0.1 N HCl (0.19 mL) and $H_2O$ (0.19 mL) was transferred by pipette to this aqueous iron(III) oxalate solution and $NaBH_4$ (6 mg, 0.16 mmol) in $H_2O$ (0.1 mL) was added to the mixture at 0° C. The resulting mixture was stirred for 30 minutes before being quenched by the addition of 30% aqueous $NH_4OH$ (1 mL). The mixture was extracted with 10% MeOH in $CH_2Cl_2$. The combined organic layer was dried over anhydrous $Na_2SO_4$ and concentrated under reduced pressure. PTLC ($SiO_2$, $Et_3N$:MeOH:EtOAc=3:3:97) afforded 11b (1.5 mg, 24%).

For 11b: $^1H$ NMR (500 MHz, $CDCl_3$) δ 9.10 (s, 1H), 8.47 (s, 1H), 7.63 (d, J=8.2 Hz, 1H), 7.39 (d, J=4.0 Hz, 1H), 7.19-7.08 (m, 3H), 6.10 (d, J=14.6 Hz, 1H), 5.81-5.76 (m, 1H), 5.47-5.39 (m, 1H), 5.28-5.21 (m, 1H), 5.11 (d, J=9.2 Hz, 1H), 4.80 (d, J=11.1 Hz, 1H), 4.06 (t, J=6.6 Hz, 1H), 4.03 (s, 1H), 3.93 (s, 1H), 3.81 (s, 3H), 3.78 (s, 3H), 3.67-3.64 (m, 1H), 3.62 (s, 1H), 3.60-3.54 (m, 2H), 3.46 (s, 1H), 3.41 (dd, J=10.3, 3.6 Hz, 1H), 3.01 (d, J=13.8 Hz, 1H), 2.90 (s, 1H), 2.81 (s, 1H), 2.72 (s, 3H), 2.67-2.62 (m, 2H), 2.45-2.40 (m, 2H), 2.32 (s, 1H), 2.25-2.21 (m, 1H), 2.09 (s, 3H), 1.66-1.57 (m, 3H), 1.42-1.29 (m, 6H), 1.00 (t, J=7.4 Hz, 3H), 0.91 (t, J=6.6 Hz, 3H); IR (film) $v_{max}$ 3367, 2925, 1735, 1615, 1238, 1039, 733 $cm^{-1}$; HRMS ESI-TOF m/z 783.4333 ($C_{45}H_{58}N_4O_8+H^+$, required 783.4327); $[\alpha]_D^{23}$ +32 (c 0.12, $CHCl_3$).

1.08 (t, J=7.0 Hz, 3H); $^{13}C$ NMR (125 MHz, $CDCl_3$) δ 173.5, 149.1, 143.0, 142.9, 133.7, 133.2, 123.7, 118.0, 115.2, 112.3, 107.4, 61.8, 56.0, 52.6, 49.3, 38.4, 30.6, 29.7, 26.2, 21.3, 10.7; IR (film) $v_{max}$ 3349, 2960, 1737, 1509, 1331 $cm^{-1}$; HRESI-TOFMS m/z 382.1748 ($C_{21}H_{23}N_3O_4+H^+$, required 382.1761); $[\alpha]_D^{23}$ +9.5 (c 0.2, acetone).

Compound 25

A solution of 10-nitrocatharanthine (14, 271 mg, 0.71 mmol, 1 equiv) in acetone (3.5 mL), MeOH (3.5 mL) and $H_2O$ (3.5 mL) was treated with Fe (1.98 g, 35.5 mmol, 50 equiv) and $NH_4Cl$ (2.03 g, 37.9 mmol, 70 equiv). After stirring at room temperature for 1 hour, the resulting mixture was quenched with the addition of 28-30% aqueous $NH_4OH$. The suspension was filtered through a plug of Celite (EtOAc rinse). The organic materials were extracted with EtOAc and dried over anhydrous $Na_2SO_4$, then concentrated under reduced pressure. Flash chromatography ($SiO_2$, EtOAc) afforded 10-aminocatharanthine (25, 154 mg, 0.063 mmol, 62%).

For 25: $^1H$ NMR (500 MHz, $CDCl_3$) δ7.50 (br s, 1H), 7.24 (d, J=8.5 Hz, 1H), 6.55 (dd, J=8.5, 2.0 Hz, 1H), 6.51 (d, J=2.0 Hz, 1H), 5.95-5.90 (m, 1H), 4.17 (d, J=1.5 Hz, 1H), 3.71 (s, 3H), 3.55 (ddd, J=14.0, 10.5, 4.0 Hz, 1H), 3.34 (dt, J=13.5, 4.5 Hz, 1H), 3.21 (ddd, J=16.5, 10.5, 4.5 Hz, 1H), 2.90-2.80 (m, 3H), 2.74-2.67 (m, 2H), 2.38-2.26 (m, 1H), 2.16-2.05 (m, 1H), 1.76 (d, J=10.5 Hz, 1H), 1.07 (t, J=7.5 Hz, 3H); $^{13}C$ NMR (125 MHz, $CDCl_3$) δ 174.2, 149.3, 142.1, 136.3, 134.0, 123.6, 122.4, 118.8, 110.4, 110.0, 96.1, 61.8, 55.0, 53.1, 52.2, 49.3, 38.6, 30.7, 26.1, 21.3, 10.6; IR (film) $v_{max}$ 3367, 2843, 1714, 1630, 1459, 906, 724 $cm^{-1}$; HRESI-TOFMS m/z 352.2018 ($C_{21}H_{25}N_3O_2+H^+$, required 352.2019); $[\alpha]_D^{23}$ +18 (c 0.7, $CHCl_3$).

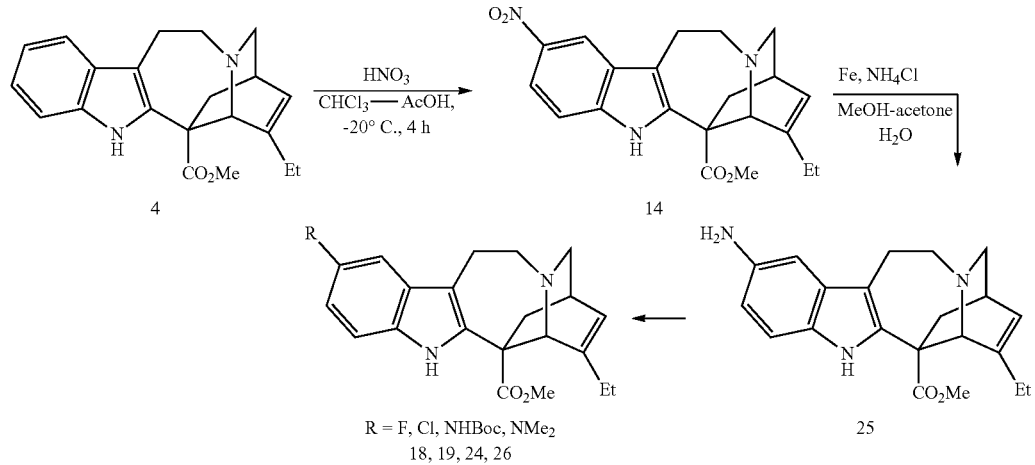

Scheme S1

Compound 14

A solution of catharanthine (4, 46.9 mg, 0.14 mmol, 1 equiv) in $CHCl_3$ (1.0 mL) and AcOH (1.0 mL) was treated with $HNO_3$ (29 μL, 0.28 mmol, 2 equiv) at −20° C. After stirring at −20° C. for 2 hours, the reaction mixture was quenched with the addition of saturated aqueous $NaHCO_3$. The organic materials were extracted with EtOAc and dried over anhydrous $Na_2SO_4$, then concentrated under reduced pressure. PTLC ($SiO_2$, EtOAc) afforded 10-nitrocatharanthine (14, 24.1 mg, 0.063 mmol, 45%) as a yellow solid.

For 14: $^1H$ NMR (500 MHz, $CDCl_3$) δ 8.34 (br s, 1H), 8.20 (d, J=2.0 Hz, 1H), 7.99 (dd, J=9.0, 2.0 Hz, 1H), 7.49 (d, J=9.0 Hz, 1H), 5.97-5.93 (m, 1H), 4.18 (s, 1H), 3.78 (s, 3H), 3.51-3.50 (m, 1H), 3.49-3.48 (m, 2H), 2.94-2.82 (m, 3H), 2.36-2.24 (m, 1H), 2.16-2.06 (m, 1H), 1.78 (d, J=11.5 Hz, 1H),

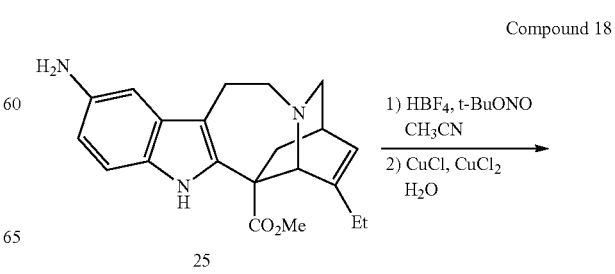

Compound 18

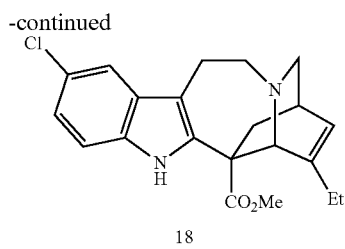

18

10-Aminocatharanthine (25, 27.3 mg, 0.078 mmol, 1 equiv) in anhydrous CH$_3$CN (1.3 mL) was cooled to 0° C. and HBF$_4$ (19 µL, 0.10 mmol, 90% purity, 1.3 equiv) was added dropwise. The reaction mixture was stirred for 15 minutes at 0° C., then warmed to room temperature and stirred for 30 minutes. The reaction mixture was re-cooled to 0° C. and t-butyl nitrite (12 µL, 0.10 mmol, 48% aqueous, 1.3 equiv) was added dropwise. The reaction mixture was stirred for 1 hour at 0° C. and then added dropwise via cannula (CH$_3$CN rinse) to a suspension of CuCl (385 mg, 3.9 mmol, 50 equiv) and CuCl$_2$ (621 mg, 4.7 mmol, 60 equiv) in H$_2$O (13 mL) at 0° C. The suspension was immediately allowed to warm to room temperature and stirred for 45 minutes. The reaction mixture was quenched with the addition of saturated aqueous NaHCO$_3$. The organic materials were extracted with EtOAc and dried over Na$_2$SO$_4$, and concentrated in vacuo. Flash chromatography (SiO$_2$, 50-100% EtOAc-hexane, gradient) afforded 10-chlorocatharanthine (18, 16.3 mg, 0.044 mmol, 57%).

For 18: $^1$H NMR (500 MHz, CDCl$_2$) δ 7.66 (br s, 1H), 7.36 (d, J=8.5 Hz, 1H), 7.22 (d, J=2.0 Hz, 1H), 7.06 (dd, J=8.5, 2.0 Hz, 1H), 5.93 (d, J=4.5 Hz, 1H), 4.16 (s, 1H), 3.73 (s, 3H), 3.55 (ddd, J=14.5, 10.5, 4.0 Hz, 1H), 3.36 (dt, J=14.0, 4.5 Hz, 1H), 3.26 (ddd, J=16.5, 10.5, 4.5 Hz, 1H), 2.90-2.80 (m, 3H), 2.75-2.67 (m, 2H), 2.35-2.25 (m, 1H), 2.15-2.05 (m, 1H), 1.76 (dd, J=12.5, 2.0 Hz, 1H), 1.07 (t, J=7.0 Hz, 3H); $^{13}$C NMR (125 MHz, CDCl$_3$) δ 174.0, 149.3, 137.1, 135.3, 127.7, 127.6, 123.6, 120.1, 119.1, 110.9, 110.4, 61.8, 55.4, 52.9, 52.4, 49.2, 38.7, 30.7, 26.2, 21.3, 10.7; IR (film) v$_{max}$ 3366, 2963, 1712, 1461, 1266, 1078, 909, 731 cm$^{-1}$; HRESI-TOFMS m/z 371.1524 (C$_{21}$H$_{23}$ClN$_2$O$_2$+H$^+$, required 371.1521); [α]$_D^{23}$ +11 (c 1.2, CHCl$_3$).

Compound 19

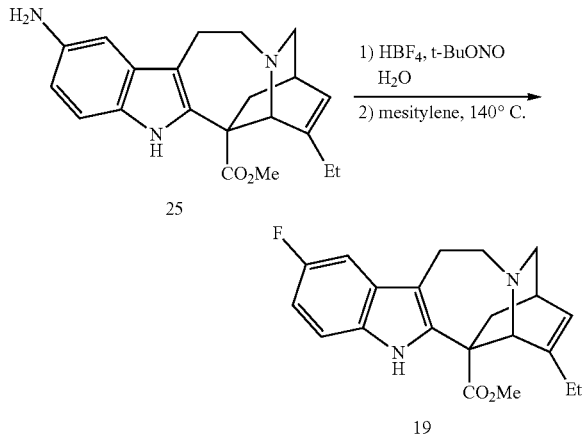

10-Aminocatharanthine (25, 29.6 mg, 0.084 mmol, 1 equiv) in anhydrous CH$_3$CN (0.84 mL) was cooled to 0° C. and HBF$_4$ (20 µL, 0.09 mmol, 90% purity, 1.1 equiv) was added dropwise. The reaction mixture was stirred for 15 minutes at 0° C., then warmed to room temperature and stirred for 30 minutes. The reaction mixture was re-cooled to 0° C. and t-butyl nitrite (9 µL, 0.09 mmol, 48% aqueous, 1.1 equiv) was added dropwise. The reaction mixture was stirred for 1 hour at 0° C. The reaction mixture was evaporated and the residue was suspended in mesitylene (0.84 mL). The suspension was warmed to 140° C. and stirred for 1 hour. The reaction mixture was quenched with the addition of saturated aqueous NaHCO$_3$ after cooling to 0° C. The organic materials were extracted with EtOAc and dried over Na$_2$SO$_4$, and concentrated in vacuo. Flash chromatography (SiO$_2$, 33-100% EtOAc-hexane, gradient) afforded 10-fluorocatharanthine (19, 7.7 mg, 0.022 mmol, 26%).

For 19: $^1$H NMR (600 MHz, CDCl$_3$) δ 7.62 (br s, 1H), 7.37 (t, J=6.0 Hz, 1H), 6.91 (d, J=9.6 Hz, 1H), 6.85 (t, J=9.0 Hz, 1H), 5.92 (d, J=6.0 Hz, 1H), 4.15 (s, 1H), 3.74 (s, 3H), 3.58-3.50 (m, 1H), 3.37 (dt, J=13.8, 4.2 Hz, 1H), 3.27 (ddd, J=15.6, 10.8, 4.2 Hz, 1H), 2.90-2.80 (m, 3H), 2.75-2.67 (m, 2H), 2.35-2.25 (m, 1H), 2.15-2.05 (m, 1H), 1.77 (d, J=12.6 Hz, 1H), 1.06 (t, J=7.2 Hz, 3H); $^{13}$C NMR (150 MHz, CDCl$_3$) δ 174.1, 159.8 (d, J=236 Hz), 149.4, 136.6, 134.8 (d, J=12.3 Hz), 125.6, 123.5, 118.9 (d, J=9.9 Hz), 110.7, 108.0 (d, J=24.2 Hz), 96.9 (d, J=24.1 Hz), 61.9, 55.4, 52.9, 52.4, 49.1, 38.8, 30.7, 26.2, 21.4, 10.6; IR (film) v$_{max}$ 3364, 2924, 1729, 1461, 1264, 750 cm$^{-1}$; HRESI-TOFMS m/z 355.1818 (C$_{21}$H$_{23}$FN$_2$O$_2$+H$^+$, required 355.1816); [α]$_D^{23}$ +12.5 (c 0.84, CHCl$_3$).

Compound 17

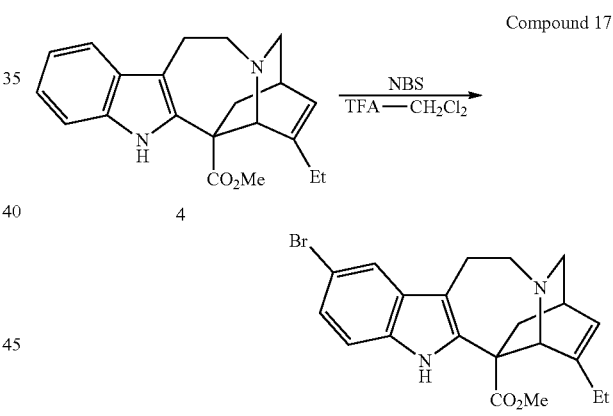

A solution of catharanthine (4, 33.9 mg, 0.10 mmol, 1 equiv) in CH$_2$Cl$_2$ (0.2 mL) was treated with TFA (0.2 mL) and NBS (N-bromosuccinimide, 17.9 mg, 0.10 mmol, 1.0 equiv) at −40° C. After stirring the reaction mixture at −40° C. for 2 hours, the reaction mixture was quenched with the addition of saturated aqueous NaHCO$_2$. The organic materials were extracted with EtOAc and dried over anhydrous Na$_2$SO$_4$, then concentrated under reduced pressure. PTLC (SiO$_2$, EtOAc) afforded 10-bromocatharanthine (17, 7.4 mg, 0.018 mmol, 18%).

For 17: $^1$H NMR (600 MHz, CDCl$_3$) δ 7.72 (br s, 1H), 7.59 (s, 1H), 7.21 (dd, J=8.4, 1.8 Hz, 1H), 7.10 (d, J=8.4 Hz, 1H), 5.95-5.90 (m, 1H), 4.15 (s, 1H), 3.74 (s, 3H), 3.53 (ddd, J=13.8, 10.2, 3.6 Hz, 1H), 3.36 (dt, J=13.8, 4.2 Hz, 1H), 3.24 (ddd, J=16.2, 10.3, 4.3 Hz, 1H), 2.90-2.78 (m, 3H), 2.76-2.68 (m, 2H), 2.35-2.25 (m, 1H), 2.14-2.05 (m, 1H), 1.76 (d, J=10.8 Hz, 1H), 1.06 (t, J=7.2 Hz, 3H); $^{13}$C NMR (150 MHz, CDCl$_3$) δ 173.9, 149.3, 137.8, 133.5, 130.8, 124.6, 123.6, 120.9, 112.7, 111.9, 110.4, 61.8, 55.4, 52.8, 52.5, 49.2, 38.7, 30.6, 26.1, 21.2, 10.6; IR (film) v$_{max}$ 3363, 2960, 1725, 1464, 1265, 1079, 731 cm$^{-1}$; HRESI-TOFMS m/z 415.1017 (C$_{21}$H$_{23}$BrN$_2$O$_2$+H$^+$, required 415.1016); [α]$_D^{23}$ +20 (c 0.8, CHCl$_3$).

Scheme S2

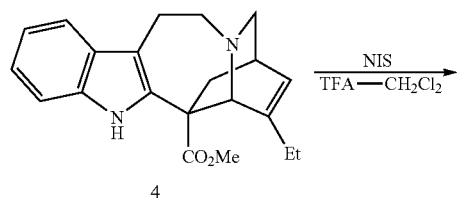

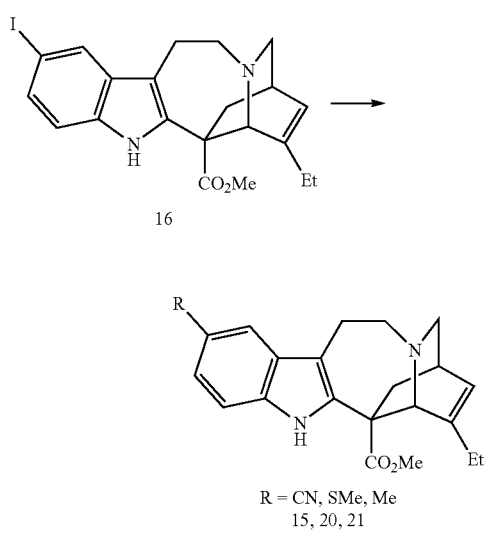

R = CN, SMe, Me
15, 20, 21

Compound 16

A solution of catharanthine (4, 916 mg, 2.7 mmol, 1 equiv) in CH$_3$NO$_2$ (5.4 mL) was treated with TFA (5.4 mL) and NIS (N-iodosuccinimide, 916 mg, 4.1 mmol, 1.5 equiv) at –40° C. After stirring the reaction mixture at –40° C. for 2 hours, the mixture was quenched with the addition of saturated aqueous NaHCO$_3$. The organic materials were extracted with EtOAc and dried over anhydrous Na$_2$SO$_4$, then concentrated under reduced pressure. Flash chromatography (SiO$_2$, 10-50% EtOAc-hexane, gradient) afforded 10-iodocatharanthine (16, 693 mg, 1.5 mmol, 55%).

For 16: $^1$H NMR (500 MHz, CDCl$_3$) δ 7.81 (br s, 1H), 7.80 (s, 1H), 7.38 (dd, J=8.5, 1.5 Hz, 1H), 7.00 (d, J=8.5 Hz, 1H), 5.95~5.90 (m, 1H), 4.15 (d, J=1.5 Hz, 1H), 3.74 (s, 3H), 3.53 (ddd, J=14.0, 10.5, 4.0 Hz, 1H), 3.34 (dt, J=14.0, 4.5 Hz, 1H), 3.23 (ddd, j=15.0, 10.5, 4.5 Hz, 1H), 2.86-2.79 (m, 3H), 2.74-2.67 (m, 2H), 2.35-2.26 (m, 1H), 2.15-2.05 (m, 1H), 1.74 (dd, J=14.0, 3.5 Hz, 1H), 1.07 (t, J=7.0 Hz, 3H); NMR (125 MHz, CDCl$_3$) δ 173.9, 149.3, 137.4, 133.9, 131.6, 130.0, 127.2, 123.6, 112.4, 110.2, 82.7, 61.8, 55.4, 52.8, 52.4, 49.2, 38.7, 30.6, 26.1, 21.2, 10.6; IR (film) v$_{max}$ 3366, 2960, 1712, 1462, 1267, 752 cm$^{-1}$; HRESI-TOFMS m/z 463.0879 (C$_{21}$H$_{23}$IN$_2$O$_2$+H$^+$, required 463.0877); [α]$_D^{23}$ +14 (c 1.0, CHCl$_3$).

Compound 15

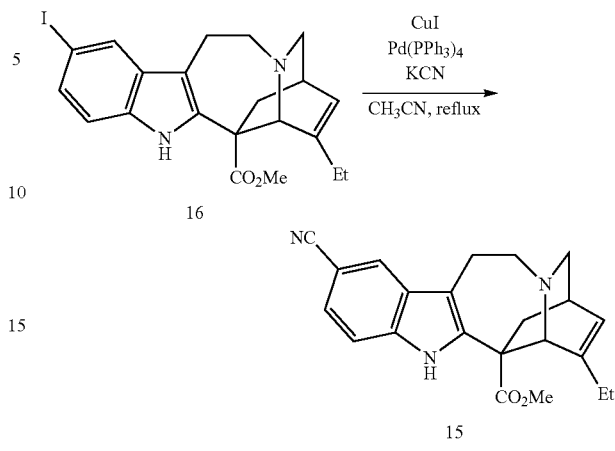

A solution of 10-iodocatharanthine (16, 20.9 mg, 0.045 mmol) in CH$_3$CN (0.45 mL) was treated with Pd(PPh$_3$)$_4$ (7.8 mg, 0.0068 mmol, 15 mol %), CuI (2.6 mg, 0.014 mmol, 30 mol %) and KCN (8.8 mg, 0.14 mmol, 3 equiv) at room temperature. After stirring the reaction mixture at 80° C. for 30 minutes, the resulting mixture was quenched with the addition of water. The organic materials were extracted with EtOAc and dried over anhydrous Na$_2$SO$_4$, then concentrated under reduced pressure. PTLC (SiO$_2$, 50% EtOAc-hexane) afforded 10-cyanocatharanthine (15, 15.5 mg, 0.043 mmol, 95%).

For 15: $^1$H NMR (600 MHz, CDCl$_3$) δ 8.09 (br s, 1H), 7.81 (s, 1H), 7.36 (dd, J=8.4, 1.2 Hz, 1H), 7.28 (d, J=8.4 Hz, 1H), 5.93 (d, J=4.8 Hz, 1H), 4.15 (s, 1H), 3.75 (s, 3H), 3.55 (ddd, J=14.4, 10.8, 4.2 Hz, 1H), 3.37 (dt, J=13.8, 4.2 Hz, 1H), 3.28 (ddd, J=15.0, 10.8, 4.2 Hz, 1H), 2.90-2.82 (m, 3H), 2.76-2.70 (m, 2H), 2.34-2.24 (m, 1H), 2.14-2.02 (m, 1H), 1.76 (d, J=11.4 Hz, 1H), 1.06 (t, J=7.2 Hz, 3H); $^{13}$C NMR (150 MHz, CDCl$_3$) δ 174.7, 150.1, 139.8, 137.5, 129.8, 125.7, 124.7, 124.5, 121.7, 112.4, 112.1, 103.3, 62.8, 56.4, 53.5, 53.4, 50.0, 39.6, 31.5, 27.1, 22.1, 11.6; IR (film) v$_{max}$ 3338, 2960, 2218, 1730, 1474, 1266, 732 cm$^{-1}$; HRESI-TOFMS m/z 362.1863 (C$_{22}$H$_{23}$N$_3$O$_2$+H$^+$, required 362.1863); [α]$_D^{23}$ +11 (c 0.2, CHCl$_3$).

Compound 20

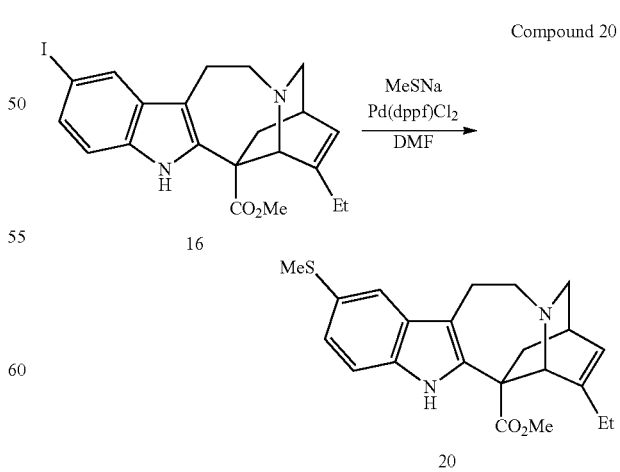

A solution of 10-iodocatharanthine (16, 30.4 mg, 0.066 mmol, 1 equiv) in DMF (0.66 mL) was treated with MeSNa (18.6 mg, 0.26 mmol, 4 equiv) and Pd(dppf)Cl$_2$ (14.4 mg, 0.020 mmol, 30 mol %) at room temperature. After stirring the reaction mixture at 80° C. for 6 hours, the resulting mixture was quenched with the addition of water. The organic materials were extracted with EtOAc and dried over anhydrous Na$_2$SO$_4$, then concentrated under reduced pressure. PTLC (SiO$_2$, 50% EtOAc-hexane) afforded 10-methylthiocatharanthine (20, 14.9 mg, 0.039 mmol, 59%).

For 20: $^1$H NMR (500 MHz, CDCl$_3$) δ7.67 (br s, 1H), 7.51 (s, 1H), 7.19 (dd, J=8.0, 1.5 Hz, 1H), 7.16 (d, J=8.5 Hz, 1H), 5.92 (d, J=4.5 Hz, 1H), 4.16 (s, 1H), 3.73 (s, 3H), 3.55 (ddd, J=14.5, 10.5, 4.0 Hz, 1H), 3.36 (dt, j=14.0, 5.0 Hz, 1H), 3.27 (ddd, J=15.0, 10.5, 4.5 Hz, 1H), 2.92-2.80 (m, 3H), 2.75-2.68 (m, 2H), 2.50 (s, 3H), 2.37-2.25 (m, 1H), 2.15-2.05 (m, 1H), 1.76 (d, J=11.0 Hz, 1H), 1.06 (t, J=7.5 Hz, 3H); $^{13}$C NMR (125 MHz, CDCl$_3$) δ 174.0, 149.3, 137.3, 133.7, 129.7, 127.5, 124.1, 123.6, 119.6, 111.0, 110.4, 61.8, 55.4, 52.9, 52.4, 49.2, 38.6, 30.7, 26.1, 21.3, 19.2, 10.6; IR (film) $v_{max}$ 3368, 2960, 1713, 1461, 1266, 1079, 731 cm$^{-1}$; HRESI-TOFMS m/z 383.1789 (C$_{22}$H$_{26}$N$_2$O$_2$S+H$^+$, required 383.1788); $[\alpha]_D^{23}$ +13 (c 0.7, CHCl$_3$).

Compound 21

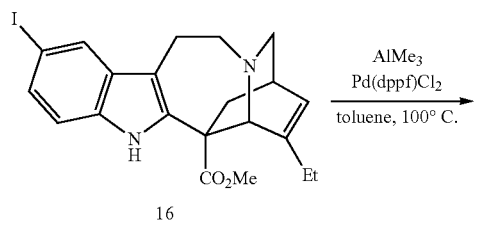

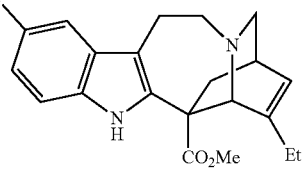

A solution of 10-iodocatharanthine (16, 105 mg, 0.23 mmol) in toluene (2.3 mL) was treated with Pd(dppf)Cl$_2$ (24.9 mg, 0.034 mmol, 15 mol %) and AlMe$_3$ (45 μL, 0.908 mmol, 4 equiv, 2.0 M solution in toluene) at room temperature. After stirring the reaction mixture at 100° C. for 2 hours, the resulting mixture was quenched with the addition of water at 0° C. The organic materials were extracted with EtOAc and dried over anhydrous Na$_2$SO$_4$, then concentrated under reduced pressure. PTLC (SiO$_2$, 50% EtOAc-hexane) afforded 10-methylcatharanthine (21, 50.2 mg, 0.14 mmol, 63%).

For 21: $^1$H NMR (500 MHz, CDCl$_3$) δ7.65 (br s, 1H), 7.29 (s, 1H), 7.14 (d, J=8.0 Hz, 1H), 6.99 (d, J=8.0 Hz, 1H), 5.94 (d, J=5.0 Hz, 1H), 4.19 (s, 1H), 3.74 (s, 3H), 3.57 (ddd, J=14.0, 10.5, 4.0 Hz, 1H), 3.37 (dt, J=13.5, 4.5 Hz, 1H), 2.28 (ddd, J=15.5, 10.5, 4.5 Hz, 1H), 2.94-2.80 (m, 3H), 2.75-2.68 (m, 2H), 2.46 (s, 3H), 2.40-2.28 (m, 1H), 2.20-2.08 (m, 1H), 1.78 (d, J=10.5 Hz, 1H), 1.09 (t, J=7.0 Hz, 3H); $^{13}$C NMR (125 MHz, CDCl$_3$) δ 174.1, 149.4, 136.5, 133.2, 129.1, 128.6, 123.5, 123.3, 117.9, 110.4, 110.2, 110.1, 61.8, 55.4, 53.1, 52.3, 49.3, 38.6, 30.7, 26.1, 21.5, 21.3, 10.6; IR (film) $v_{max}$ 3375, 2960, 1716, 1457, 1266, 752 cm$^{-1}$; HRESI-TOFMS m/z 351.2068 (C$_{22}$H$_{26}$N$_2$O$_2$+H$^+$, required 351.2067); $[\alpha]_D^{20}$ +16 (c 0.6, CHCl$_3$).

Scheme S3

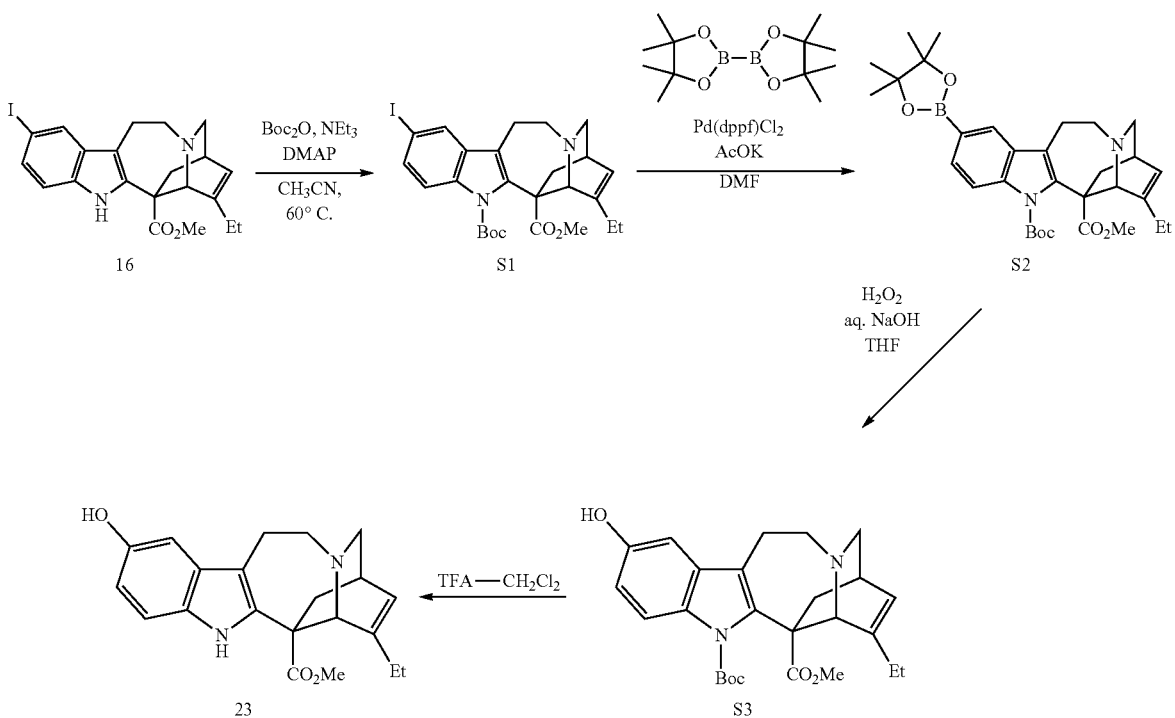

Compound S1

A solution of 10-iodocatharanthine (16, 307 mg, 0.66 mmol, 1 equiv) in $CH_3CN$ (1.3 mL) was treated with $Boc_2O$ (di-tert-butylpyrocarbonate, 290 mg, 1.3 mmol, 2 equiv), $Et_3N$ (280 μL, 2.0 mmol, 3 equiv) and DMAP (4-dimethylaminopyridine, 40.6 mg, 0.33 mmol, 50 mol%) at 0° C. After stirring the reaction mixture at 60° C. for 12 hours, the resulting mixture was quenched with the addition of water. The organic materials were extracted with EtOAc and dried over anhydrous $Na_2SO_4$, then concentrated under reduced pressure. Flash chromatography ($SiO_2$, 50% EtOAc-hexane) afforded N-tert-butyloxycarbonyl-10-iodocatharanthine (S1, 242 mg, 0.43 mmol, 65%).

For S1: $^1H$ NMR (500 MHz, $CDCl_3$) δ7.80 (d, J=1.5 Hz, 1H), 7.66 (d, J=8.5 Hz, 1H), 7.52 (dd, J=9.0, 2.0 Hz, 1H), 5.97 (d, J=6.5 Hz, 1H), 4.14 (s, 1H), 3.64 (dt, J=15.0, 4.2 Hz, 1H), 3.53 (s, 3H), 3.19 (ddd, J=17.0, 14.0, 6.0 Hz, 1H), 3.03 (dt, J=8.0, 3.0 Hz, 1H), 2.92-2.81 (m, 2H), 2.78 (dt, J=13.0, 2.5 Hz, 1H), 2.65-2.60 (m, 1H), 2.47 (d, J=8.5 Hz, 1H), 2.38-2.28 (m, 1H), 1.94-1.85 (m, 1H), 1.68 (dd, J=13.5, 2.5 Hz, 1H), 1.62 (s, 9H), 1.08 (t, J=7.5 Hz, 3H); $^{13}C$ NMR (125 MHz, $CDCl_3$) δ 172.5, 150.0, 147.2, 140.4, 134.5, 132.4, 131.9, 127.2, 123.3, 117.6, 117.3, 86.0, 84.4, 58.6, 55.9, 52.8, 52.0, 38.4, 31.5, 28.1, 26.7, 21.8, 10.3; IR (film) $v_{max}$ 2937, 1735, 1454, 1353, 1315, 1136, 730 $cm^{-1}$; HRESI-TOFMS m/z 563.1402 ($C_{26}H_{311}N_2O_4+H^+$, required 562.1401); $[α]_D^{23}$ +19 (c 0.6, $CHCl_3$).

Compound S2

A solution of S1 (61.1 mg, 0.11 mmol, 1 equiv) in DMF (3.0 mL) was treated with potassium acetate (106 mg, 1.1 mmol, 10 equiv) and bis(pinacolato)diboron (138 mg, 0.55 mmol, 5 equiv) at room temperature. Ar was bubbled through the mixture for 10 minutes. The reaction mixture was treated with $Pd(dppf)Cl_2$ (17.8 mg, 0.0218 mmol, 20 mol %) at room temperature. After stirring the reaction mixture at 80° C. for 16 hours, the resulting mixture was quenched with the addition of water at 0° C. The organic materials were extracted with EtOAc and dried over anhydrous $Na_2SO_4$, then concentrated under reduced pressure. PTLC ($SiO_2$, 50% EtOAc-hexane) afforded S2 (54.5 mg, 0.097 mmol, 89%).

For S2: $^1H$ NMR (500 MHz, $CDCl_3$) δ7.97 (s, 1H), 7.88 (d, J=8.0 Hz, 1H), 7.70 (d, J=8.5 Hz, 1H), 5.95 (d, J=6.5 Hz, 1H), 4.16 (s, 1H), 3.62 (ddd, J=11.5, 4.5, 3.0 Hz, 1H), 3.51 (s, 3H), 3.21 (ddd, J=16.0, 13.5, 5.0 Hz, 1H), 3.09 (dt, J=19.2, 3.5 Hz, 1H), 3.01 (dt, J=8.5, 3.0 Hz, 1H), 2.85 (dt, J=4.0, 12.5 Hz, 1H), 2.76 (dt, J=13.5, 3.0 Hz, 1H), 2.64-2.58 (m, 1H), 2.45 (d, J=8.0 Hz, 1H), 2.28-2.18 (m, 1H), 1.94-1.85 (m, 1H), 1.69 (dd, J=13.0, 3.0 Hz, 1H), 1.60 (s, 9H), 1.35 (s, 12H), 1.06 (t, J=7.5 Hz, 3H); $^{13}C$ NMR (125 MHz, $CDCl_3$) δ 172.7, 150.2, 147.3, 139.4, 137.2, 130.3, 129.0, 125.3, 123.1, 118.7, 114.6, 83.9, 83.5, 58.6, 55.8, 52.8, 51.8, 38.4, 31.5, 28.0, 26.6, 24.8, 22.5, 21.7, 10.2; IR (film) $v_{max}$ 2976, 1735, 1322, 1137, 730 $cm^{-1}$; HRESI-TOFMS m/z 563.3288 ($C_{32}H_{43}N_2O_6+H^+$, required 563.3288); $[α]_D^{23}$ +22 (c 0.5, $CHCl_2$).

Compound S3

A THF (0.57 mL) and aqueous NaOH (0.57 mL, 2% solution) solution of S2 (32.3 mg, 0.057 mmol) was treated with $H_2O_2$ (56 μL, 0.57 mmol, 35% solution, 10 equiv) at room temperature. After stirring the reaction mixture at room temperature for 12 hours, the resulting mixture was quenched with the addition of saturated $NH_4Cl/NH_4OH$ buffer solution. The organic materials were extracted with EtOAc and dried over anhydrous $Na_2SO_4$, then concentrated under reduced pressure. PTLC ($SiO_2$, 50% EtOAc-hexane) afforded N-tert-butyloxycarbonyl-10-hydroxycatharanthine (S3, 19.2 mg, 0.042 mmol, 74%).

For S3: $^1H$ NMR (600 MHz, $CDCl_3$) δ7.67 (d, J=8.4 Hz, 1H), 6.82 (d, J=1.8 Hz, 1H), 6.73 (d, J=8.4 Hz, 1H), 5.99 (d, J=6.0 Hz, 1H), 4.19 (s, 1H), 3.69-3.60 (m, 1H), 3.56 (s, 3H), 3.20-3.12 (m, 1H), 3.10-3.04 (m, 1H), 2.90-2.77 (m, 3H), 2.66 (s, 1H), 2.48 (d, J=8.4 Hz, 1H), 2.30-2.20 (m, 1H), 1.95-1.84 (m, 1H), 1.70 (d, J=11.4 Hz, 1H), 1.61 (s, 9H), 1.06 (t, J=7.2 Hz, 3H); $^{13}C$ NMR (150 MHz, $CDCl_3$) δ 173.4, 152.0, 150.3, 147.1, 139.8, 130.5, 129.4, 123.5, 118.5, 116.2, 113.0, 103.6, 83.6, 58.7, 53.3, 52.0, 38.2, 31.5, 28.1, 26.7, 21.9, 10.3; IR (film) $v_{max}$ 3372, 2939, 1725, 1458, 1347, 1126, 729 $cm^{-1}$; HRESI-TOFMS m/z 453.2379 ($C_{26}H_{32}N_2O_5+H^+$, required 453.2384); $[α]_D^{23}$ +27 (c 0.9, $CHCl_3$).

Compound 23

A solution of Compound S3 (54.9 mg, 0.12 mmol) in $CH_2Cl_2$ (1.2 mL) was treated with TFA (1.2 mL) at 0° C. After stirring the reaction mixture at room temperature for 2 hours, the resulting mixture was quenched with the addition of saturated aqueous $NaHCO_2$. The organic materials were extracted with $CH_2Cl_2$ and dried over anhydrous $Na_2SO_4$, then concentrated under reduced pressure. PTLC ($SiO_2$, EtOAc) afforded 10-hydroxycatharanthine (23, 17.9 mg, 0.051 mmol, 42%).

For 23: $^1H$ NMR (500 MHz, $CDCl_2$) δ7.52 (br s, 1H), 7.07 (d, J=8.5 Hz, 1H), 6.87 (d, J=2.0 Hz, 1H), 6.70 (dd, J=9.0, 2.5 Hz, 1H), 5.93 (d, J=4.5 Hz, 1H), 4.17 (s, 1H), 3.73 (s, 3H), 3.58-3.50 (m, 1H), 3.36 (dt, J=14.0, 4.5 Hz, 1H), 3.22 (ddd, J=16.0, 10.5, 4.0 Hz, 1H), 2.90-2.78 (m, 3H), 2.77-2.68 (m, 2H), 2.36-2.27 (m, 1H), 2.15-2.05 (m, 1H), 1.77 (d, J=11.0 Hz, 1H), 1.05 (t, J=7.5 Hz, 3H); $^{13}C$ NMR (125 MHz, $CDCl_3$) δ174.0, 149.8, 149.3, 137.4, 130.0, 129.8, 123.7, 111.5, 111.1, 110.2, 103.0, 62.0, 55.3, 53.1, 52.4, 49.6, 38.5, 30.6, 26.1, 21.3, 10.6; IR (film) $v_{max}$ 3380, 2962, 1726, 1455, 1220, 732 $cm^{-1}$; HRESI-TOFMS m/z 353.1871 ($C_{21}H_{24}N_2O_3+H^+$, required 353.1860); $[α]_D^{23}$ +16 (c 1.0, $CHCl_3$).

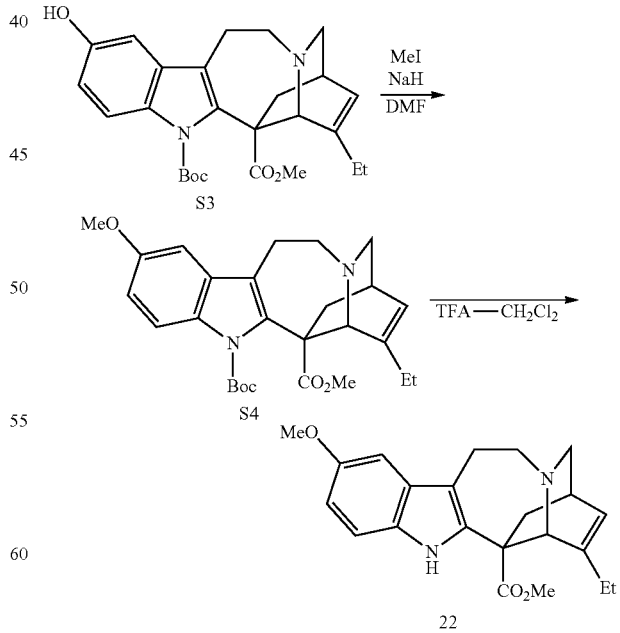

Scheme S4

Compound 22

A solution of Compound S3 (60.7 mg, 0.13 mmol, 1 equiv) in DMF (0.26 mL) was treated with NaH (4.6 mg, 2.0 mmol, 1.5 equiv) at 0° C. After stirring the reaction mixture at 0° C. for 10 minutes, MeI (17 μL, 0.27 mmol, 2 equiv) was added to the resulting mixture. After stirring the reaction mixture at 0° C. for 10 minutes, the resulting mixture was quenched with the addition of saturated aqueous NH$_4$Cl/NH$_4$OH buffer solution. The organic materials were extracted with EtOAc and dried over anhydrous Na$_2$SO$_4$, then concentrated under reduced pressure to provide compound S4.

A CH$_2$Cl$_2$ (1.2 mL) solution of S4 was treated with TFA (1.2 mL) at 0° C. After stirring the reaction mixture at room temperature for 2 hours, the resulting mixture was quenched with the addition of saturated aqueous NaHCO$_3$. The organic materials were extracted with CH$_2$Cl$_2$ and dried over anhydrous Na$_2$SO$_4$, then concentrated under reduced pressure. PTLC (SiO$_2$, EtOAc) afforded 10-methoxycatharanthine (22, 14.2 mg, 0.039 mmol, 29% for 2 steps).

For 22: $^1$H NMR (500 MHz, CHCl$_3$) δ7.52 (s, 1H), 7.12 (d, J=8.5 Hz, 1H), 6.93 (d, J=2.5 Hz, 1H), 6.80 (dd, J=9.0, 2.5 Hz, 1H), 5.92 (d, J=5.0 Hz, 1H), 4.16 (s, 1H), 3.85 (s, 3H), 3.73 (s, 3H), 3.55 (ddd, J=14.0, 10.5, 3.5 Hz, 1H), 3.38 (dt, J=14.0, 5.0 Hz, 1H), 3.27 (ddd, J=16.5, 11.0, 4.5 Hz, 1H), 2.89-2.80 (m, 3H), 2.75-2.67 (m, 2H), 2.35-2.26 (m, 1H), 2.16-2.06 (m, 1H), 1.81-1.74 (m, 1H), 1.06 (t, J=7.5 Hz, 3H); $^{13}$C NMR (125 MHz, CDCl$_3$) δ174.1, 154.1, 149.4, 137.3, 130.0, 129.4, 123.5, 111.8, 111.2, 110.6, 100.5, 62.0, 56.0, 55.5, 53.0, 52.3, 49.2, 38.6, 30.7, 26.2, 21.4, 10.6; IR (film) v$_{max}$ 3378, 2947, 1716, 1486, 1218, 1137, 753 cm$^{-1}$; HRESI-TOFMS m/z 367.2018 (C$_{22}$H$_{26}$N$_2$O$_3$+H$^+$, required 367.2016); [α]$_D^{23}$ +15 (c 0.7, CHCl$_3$).

mg, 0.028 mmol, 1 equiv) in CF$_3$CH$_2$OH (0.12 mL), aqueous 0.1 N HCl (0.6 mL) and H$_2$O (0.6 mL) at room temperature. The reaction mixture was stirred for 20 hours at room temperature followed by cooling to 0° C. and addition of NaBH$_4$ (1.1 mg, 0.028 mmol, 1 equiv) in H$_2$O (0.5 mL). The resulting mixture was stirred for 30 minutes at 0° C. before being quenched with the addition of 28-30% NH$_4$OH (10 mL). The mixture was extracted with CH$_2$Cl$_2$ and the organic layer was dried over Na$_2$SO$_4$ and concentrated under reduced pressure. Flash chromatography (SiO$_2$, EtOAc) provided 10'-cyanoanhydrovinblastine (15a, 1.7 mg, 0.0021 mmol, 7%) as a white solid.

For 15a: $^1$H NMR (500 MHz, CDCl$_3$) δ9.72 (br s, 1H), 8.32 (s, 1H), 7.85 (s, 1H), 7.38 (dd, J=8.5, 1.5 Hz, 1H), 7.13 (d, J=8.0 Hz, 1H), 6.44 (s, 1H), 6.12 (s, 1H), 5.87 (dd, J=10.0, 5.0 Hz, 1H), 5.46 (br s, 1H), 5.44 (s, 1H), 5.30 (d, J=10.5 Hz, 1H), 3.82 (s, 3H), 3.80 (s, 3H), 3.73 (s, 1H), 3.65 (s, 3H), 3.53 (br d, J=16.5 Hz, 1H), 3.45-3.15 (m, 6H), 3.05-2.95 (m, 2H), 2.78 (d, J=16.5 Hz, 2H), 2.71 (s, 3H), 2.58 (s, 1H), 2.68-2.58 (m, 2H), 2.48-2.37 (m, 2H), 2.10 (s, 3H), 1.92 (dd, J=12.0, 7.0 Hz, 2H), 1.85-1.75 (m, 2H), 1.40-1.25 (m, 2H), 0.99 (t, J=7.5 Hz, 3H), 0.73 (t, J=7.0 Hz, 3H); IR (film) v$_{max}$ 3460, 2960, 2218, 1741, 1614, 1460, 1232, 1041, 750 cm$^{-1}$; HRESI-TOF m/z 818.4120 (C$_{47}$H$_{55}$N$_5$O$_8$+H$^+$, required 818.4123); [α]$_D^{23}$ +5 (c 0.8, CHCl$_3$). When this reaction was run for 2 hours at room temperature, only trace amounts of 15a (0-3%) were detected.

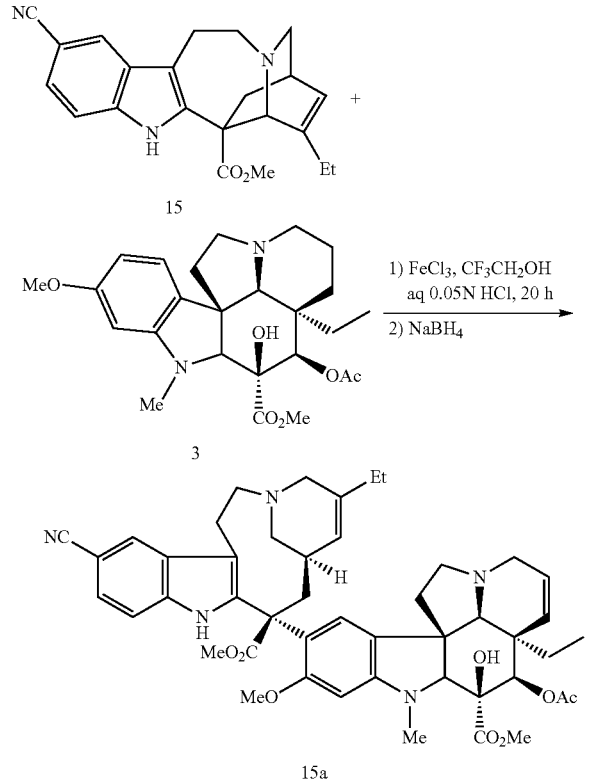

10'-Cyanoanhydrovinblastine (15a)

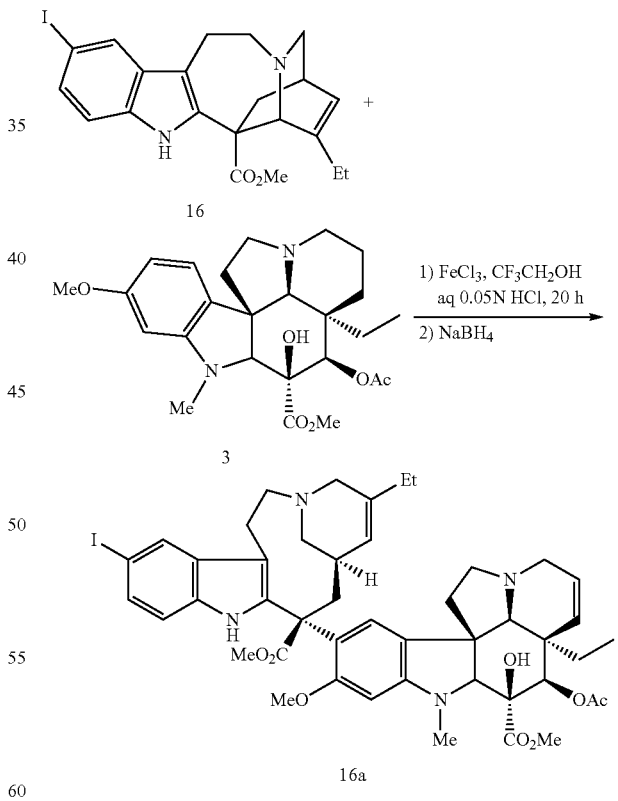

10'-Iodoanhydrovinblastine (16a)

Iron(III) chloride hexahydrate (38.1 mg, 0.14 mmol, 5 equiv) was added to a solution of (−)-vindoline (3, 12.9 mg, 0.028 mmol, 1 equiv) and 10-cyanocatharanthine (15, 10.2

Iron(III) chloride hexahydrate (80.1 mg, 0.30 mmol, 5 equiv) was added to a solution of (−)-vindoline (3, 27.1 mg, 0.059 mmol, 1 equiv) and 10-iodocatharanthine (16, 27.4 mg, 0.059 mmol, 1 equiv) in CF$_3$CH$_2$OH (1.2 mL), aqueous 0.1 N HCl (1.2 mL) and H$_2$O (1.2 mL) at room temperature under Ar. The reaction mixture was stirred for 2 hours at room temperature followed by cooling to 0° C. and addition of NaBH$_4$ (2.2 mg, 0.059 mmol, 1 equiv) in H$_2$O (0.5 mL). The resulting mixture was stirred for 30 minutes at 0° C. under Ar before being quenched with the addition of 28~30% NH$_4$OH (10 mL). The mixture was extracted with CH$_2$Cl$_2$ and the organic layer was dried over Na$_2$SO$_4$ and concentrated under reduced pressure. Flash chromatography (SiO$_2$, EtOAc) provided 10'-iodoanhydrovinblastine (16a, 15.8 mg, 0.017 mmol, 29%) as a white solid.

For 16a: $^1$H NMR (400 MHz, CDCl$_2$) δ 9.74 (br s, 1H), 8.07 (br s, 1H), 7.82 (d, J=1.2 Hz, 1H), 7.40 (dd, J=8.8, 1.6 Hz, 1H), 6.89 (d, J=8.4 Hz, 1H), 6.48 (s, 1H), 6.11 (s, 1H), 5.86 (dd, J=10.4, 3.6 Hz, 1H), 5.47 (br s, 1H), 5.44 (s, 1H), 5.29 (d, J=10.0 Hz, 1H), 3.81 (s, 3H), 3.79 (s, 3H), 3.72 (s, 1H), 3.63 (s, 3H), 3.54 (br d, J=17.2 Hz, 1H), 3.45-3.15 (m, 6H), 3.04-2.92 (m, 2H), 2.81 (d, J=16.0 Hz, 2H), 2.71 (s, 3H), 2.62 (s, 1H), 2.64-2.58 (m, 1H), 2.48-2.37 (m, 2H), 2.20-2.08 (m, 1H), 2.10 (s, 3H), 1.92 (dd, J=12.0, 7.0 Hz, 2H), 1.85-1.70 (m, 2H), 1.38-1.25 (m, 2H), 0.99 (t, J=7.6 Hz, 3H), 0.75 (t, J=7.2 Hz, 3H); IR (film) v$_{max}$ 3451, 2958, 1741, 1615, 1461, 1243, 1042, 750 cm$^{-1}$; HRESI-TOFMS m/z 919.3109 (C$_{46}$H$_{55}$IN$_4$O$_8$+H$^+$, required 919.3137); [α]$_D^{23}$ +0.1 (c 1.0, CHCl$_3$). When this reaction was run for 20 hours or 60 hours at room temperature, compound 16a was isolated in yields of 40% or 48%, respectively.

ture. The reaction mixture was stirred for 2 hours at room temperature followed by cooling to 0° C. and addition of NaBH$_4$ (1.8 mg, 0.049 mmol, 1 equiv) in H$_2$O (0.5 mL). The resulting mixture was stirred for 30 minutes at 0° C. before being quenched with the addition of 28-30% NH$_4$OH (10 mL). The mixture was extracted with CH$_2$Cl$_2$ and the organic layer was dried over Na$_2$SO$_4$ and concentrated under reduced pressure. Flash chromatography (SiO$_2$, EtOAc) provided 10'-bromoanhydrovinblastine (17a, 11.5 mg, 0.013 mmol, 27%) as a white solid.

For 17a: $^1$H NMR (500 MHz, CDCl$_3$) δ9.75 (br s, 1H), 8.07 (br s, 1H), 7.62 (d, J=1.5 Hz, 1H), 7.23 (s, 1H), 6.97 (d, J=8.5 Hz, 1H), 6.49 (s, 1H), 6.11 (s, 1H), 5.86 (dd, J=10.5, 4.0 Hz, 1H), 5.46 (br s, 1H), 5.45 (s, 1H), 5.29 (d, J=10.0 Hz, 1H), 3.81 (s, 3H), 3.79 (s, 3H), 3.73 (s, 1H), 3.63 (s, 3H), 3.53 (br d, J=16.5 Hz, 1H), 3.42-3.15 (m, 6H), 3.05-2.92 (m, 2H), 2.81 (d, J=16.0 Hz, 2H), 2.71 (s, 3H), 2.61 (s, 1H), 2.64-2.55 (m, 1H), 2.46-2.38 (m, 2H), 2.20-2.10 (m, 1H), 2.10 (s, 3H), 1.92 (dd, J=12.0, 7.0 Hz, 2H), 1.85-1.70 (m, 2H), 1.44-1.25 (m, 2H), 0.99 (t, J=7.5 Hz, 3H), 0.75 (t, J=7.0 Hz, 3H); IR (film) v$_{max}$ 2926, 1739, 1614, 1462, 1228, 1040 cm$^{-1}$; HRESI-TOFMS m/z 871.3235 (C$_{46}$H$_{55}$BrN$_4$O$_8$+H$^+$, required 871.3276); [α]$_D^{23}$ +9 (c 0.15, CHCl$_3$).

10'-Bromoanhydrovinblastine (17a)

10'-Chloroanhydrovinblastine (18a)

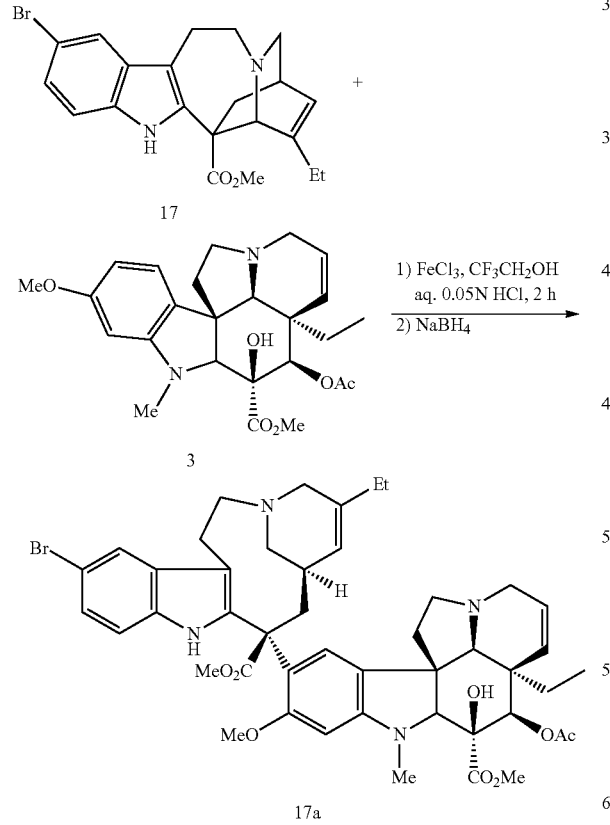

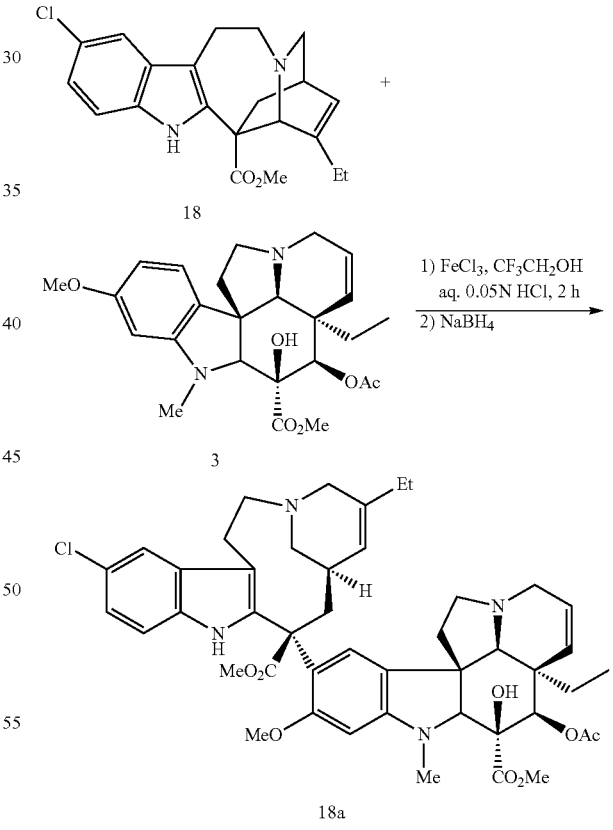

Iron(III) chloride hexahydrate (66.0 mg, 0.24 mmol, 5 equiv) was added to a solution of (−)-vindoline (3, 22.3 mg, 0.049 mmol, 1 equiv) and 10-bromocatharanthine (17, 20.2 mg, 0.049 mmol, 1 equiv) in CF$_3$CH$_2$OH (0.98 mL), aqueous 0.1 N HCl (0.98 mL) and H$_2$O (0.98 mL) at room tempera- Iron(III) chloride hexahydrate (20.3 mg, 0.075 mmol, 5 equiv) was added to a solution of (−)-vindoline (3, 6.9 mg, 0.015 mmol, 1 equiv) and 10-chlorocatharanthine (18, 5.6 mg, 0.015 mmol, 1 equiv) in CF$_3$CH$_2$OH (0.07 mL), aqueous 0.1 N HCl (0.35 mL) and H$_2$O (0.35 mL) at room temperature. The reaction mixture was stirred for 2 hours at room temperature followed by cooling to 0° C. and addition of NaBH$_4$ (0.6 mg, 0.015 mmol, 1 equiv) in H$_2$O (0.5 mL). The resulting mixture was stirred for 30 min at 0° C. before being quenched with the addition of 28-30% NH$_4$OH (10 mL). The mixture was extracted with CH$_2$Cl$_2$ and the organic layer was dried over Na$_2$SO$_4$ and concentrated under reduced pressure. Flash chromatography (SiO$_2$, EtOAc) provided 10'-chloroanhydrovinblastine (18a, 4.0 mg, 0.0048 mmol, 32%) as a white solid.

For 18a: $^1$H NMR (500 MHz, CDCl$_3$) δ 9.75 (br s, 1H), 8.02 (br s, 1H), 7.40 (d, J=8.5 Hz, 1H), 7.09 (s, 1H), 7.08 (d, J=9.0 Hz, 1H), 6.52 (s, 1H), 6.11 (s, 1H), 5.88 (dd, J=10.5, 4.5 Hz, 1H), 5.48 (br s, 1H), 5.46 (s, 1H), 5.30 (d, J=10.0 Hz, 1H), 3.81 (s, 3H), 3.80 (s, 3H), 3.73 (s, 1H), 3.63 (s, 3H), 3.58-3.50 (m, 1H), 3.45-3.16 (m, 6H), 3.08-2.95 (m, 2H), 2.84 (d, J=16.0 Hz, 2H), 2.72 (s, 3H), 2.65 (s, 1H), 2.48-2.38 (m, 2H), 2.20-2.10 (m, 1H), 2.11 (s, 3H), 2.00-1.90 (m, 2H), 1.88-1.75 (m, 2H), 1.40-1.25 (m, 2H), 1.00 (t, J=7.5 Hz, 3H), 0.77 (t, J=7.2 Hz, 3H); IR (film) v$_{max}$ 3464, 2925, 1739, 1615, 1503, 1460, 1231, 1040, 750 cm$^{-1}$; HRESI-TOFMS m/z 827.3764 (C$_{46}$H$_{55}$ClN$_4$O$_8$+H$^+$, required 827.3781); [α]$_D^{23}$ +24 (c 0.2, CHCl$_3$).

10'-Fluoroanhydrovinblastine (19a)

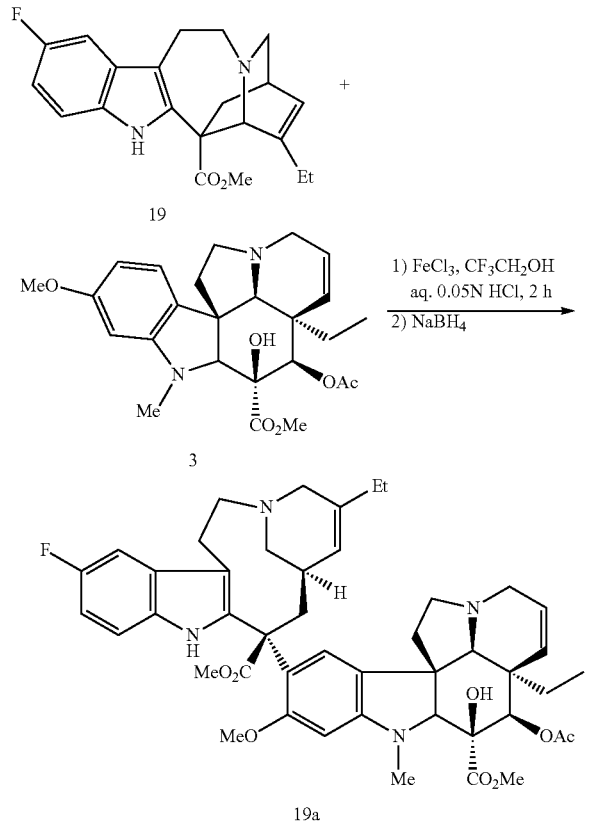

Iron(III) chloride (25.9 mg, 0.096 mmol, 5 equiv) was added to a solution of (−)-vindoline (3, 8.8 mg, 0.019 mmol, 1 equiv) and 10-fluoro-catharanthine (19, 6.8 mg, 0.019 mmol, 1 equiv) in CF$_3$CH$_2$OH (0.08 mL), aqueous 0.1 N HCl (0.38 mL) and H$_2$O (0.38 mL) at room temperature. The reaction mixture was stirred for 2 hours at room temperature followed by cooling to 0° C. and addition of NaBH$_4$ (0.7 mg, 0.019 mmol, 1 equiv) in H$_2$O (0.5 mL). The resulting mixture was stirred for 30 minutes at 0° C. before being quenched with the addition of 28-30% NH$_4$OH (10 mL). The mixture was extracted with CH$_2$Cl$_2$ and the organic layer was dried over Na$_2$SO$_4$ and concentrated under reduced pressure. Flash chromatography (SiO$_2$, EtOAc) provided 10'-fluoroanhydrovinblastine (19a, 10.1 mg, 0.012 mmol, 65%) as a white solid.

For 19a: $^1$H NMR (600 MHz, CDCl$_3$) δ 9.78 (br s, 1H), 8.01 (br s, 1H), 7.40 (dd, J=9.0, 5.4 Hz, 1H), 6.87 (dt, J=2.4, 9.6 Hz, 1H), 6.78 (dd, J=9.6, 2.4 Hz, 1H), 6.51 (br s, 1H), 6.11 (s, 1H), 5.88 (dd, J=10.2, 3.6 Hz, 1H), 5.50 (br s, 1H), 5.45 (s, 1H), 5.30 (d, J=10.2 Hz, 1H), 3.81 (s, 3H), 3.79 (s, 3H), 3.73 (s, 1H), 3.63 (s, 3H), 3.60-3.50 (m, 1H), 3.45-3.15 (m, 6H), 3.08-2.90 (m, 2H), 2.82 (d, J=15.6 Hz, 2H), 2.71 (s, 3H), 2.64 (s, 1H), 2.50-2.38 (m, 2H), 2.15-2.05 (m, 1H), 2.11 (s, 3H), 1.98-1.90 (m, 2H), 1.86-1.72 (m, 2H), 1.40-1.20 (m, 2H), 1.00 (t, J=7.2 Hz, 3H), 0.77 (t, J=7.2 Hz, 3H); IR (film) v$_{max}$ 3461, 2956, 1740, 1618, 1234 cm$^{-1}$; HRESI-TOFMS m/z 811.4063 (C$_{46}$H$_{55}$FN$_4$O$_8$+H$^+$, required 811.4076); [α]$_D^{23}$ +15 (c 1.0, CHCl$_3$).

10'-Thiomethylanhydrovinblastine (20a)

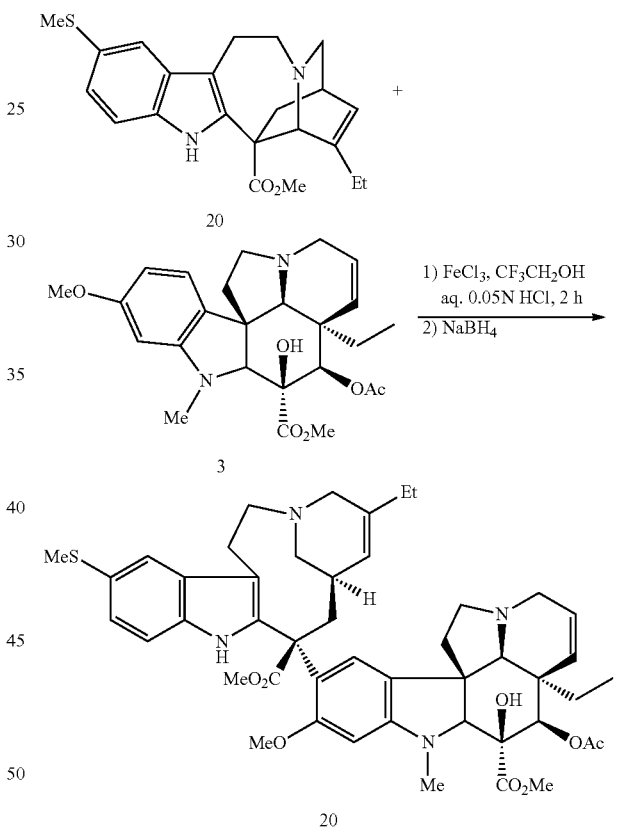

Iron(III) chloride hexahydrate (62.8 mg, 0.233 mmol, 5 equiv) was added to a solution of (−)-vindoline (3, 21.2 mg, 0.047 mmol, 1 equiv) and 10-thiomethylcatharanthine (20, 17.8 mg, 0.047 mmol, 1 equiv) in CF$_3$CH$_2$OH (0.19 mL), aqueous 0.1 N HCl (0.93 mL) and H$_2$O (0.93 mL) at room temperature. The reaction mixture was stirred for 2 hours at room temperature followed by cooling to 0° C. and addition of NaBH$_4$ (1.8 mg, 0.047 mmol, 1 equiv) in H$_2$O (0.5 mL). The resulting mixture was stirred for 30 minutes at 0° C. before being quenched with the addition of 28-30% NH$_4$OH (10 mL). The mixture was extracted with CH$_2$Cl$_2$ and the organic layer was dried over Na$_2$SO$_4$ and concentrated under reduced pressure. Flash chromatography (SiO$_2$, EtOAc) provided 10'-thiomethylanhydrovinblastine (20a, 27.3 mg, 0.033 mmol, 70%) as a white solid.

For 20a: $^1$H NMR (500 MHz, CDCl$_3$) δ 9.76 (br s, 1H), 8.03 (br s, 1H), 7.50 (s, 1H), 7.21 (dd, J=8.0, 1.5 Hz, 1H), 7.06 (d, J=9.0 Hz, 1H), 6.52 (br s, 1H), 6.11 (s, 1H), 5.87 (dd, J=10.5, 4.0 Hz, 1H), 5.51 (br s, 1H), 5.45 (s, 1H), 5.30 (d, J=10.5 Hz, 1H), 3.82 (s, 3H), 3.79 (s, 3H) 3.73 (s, 1H), 3.63 (s, 3H), 3.58 (br d, J=14.0 Hz, 1H), 3.45-3.10 (m, 6H), 3.10-2.94 (m, 2H), 2.80 (d, J=13.5 Hz, 2H), 2.71 (s, 3H), 2.64 (s, 1H), 2.68-2.58 (m, 2H), 2.52 (s, 3H), 2.50-2.38 (m, 2H), 2.10 (s, 3H), 2.00-1.90 (m, 2H), 1.85-1.72 (m, 2H), 1.40-1.25 (m, 2H), 1.00 (t, J=7.5 Hz, 3H), 0.77 (t, J=7.5 Hz, 3H); IR (film) $v_{max}$ 3566, 2961, 1739, 1614, 1461, 1228, 1041, 731 cm$^{-1}$; HRESI-TOFMS m/z 839.4022 (C$_{47}$H$_{58}$N$_4$O$_8$S+H$^+$, required 839.4048); $[\alpha]_D^{23}$ +13 (c 0.2, CHCl$_3$).

10'-methylanhydrovinblastine (21a)

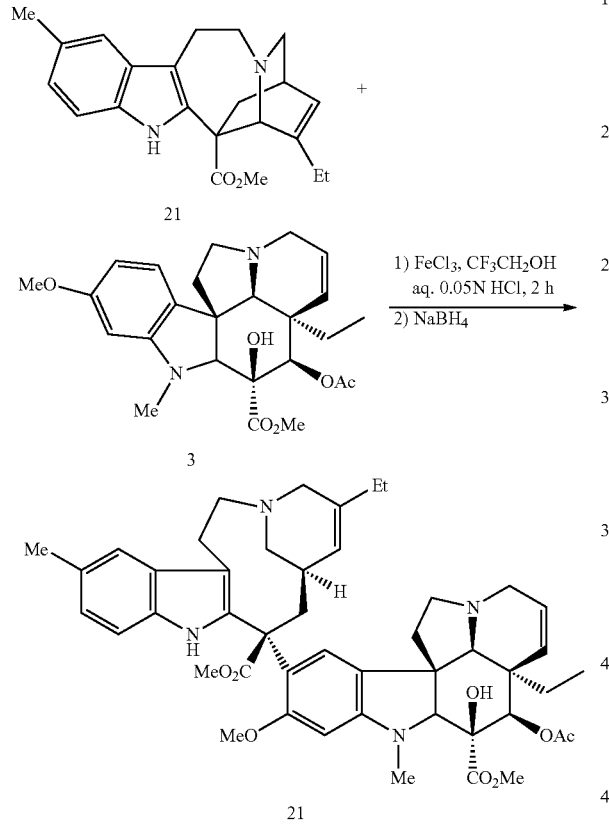

Iron(III) chloride hexahydrate (97.3 mg, 0.36 mmol, 5 equiv) was added to a solution of (−)-vindoline (3, 32.9 mg, 0.072 mmol) and 10-methylcatharanthine (21, 25.3 mg, 0.072 mmol, 1 equiv) in CF$_3$CH$_2$OH (0.29 mL), aqueous 0.1 N HCl (1.4 mL) and H$_2$O (1.4 mL) at room temperature. The reaction mixture was stirred for 2 hours at room temperature followed by cooling to 0° C. and addition of NaBH$_4$ (2.7 mg, 0.072 mmol, 1 equiv) in H$_2$O (0.5 mL). The resulting mixture was stirred for 30 minutes at 0° C. before being quenched with the addition of 28-30% NH$_4$OH (10 mL). The mixture was extracted with CH$_2$Cl$_2$ and the organic layer was dried over Na$_2$SO$_4$ and concentrated under reduced pressure. Flash chromatography (SiO$_2$, EtOAc) provided 10'-methylanhydrovinblastine (21a, 55.4 mg, 0.069 mmol, 95%) as a white solid.

For 21a: $^1$H NMR (600 MHz, CDCl$_3$) δ 9.84 (br s, 1H), 7.93 (br s, 1H), 7.28 (s, 1H), 7.02 (d, J=7.8 Hz, 1H), 6.98 (d, J=7.8 Hz, 1H), 6.69 (s, 1H), 6.11 (s, 1H), 5.85 (dd, j=9.6, 3.6 Hz, 1H), 5.46 (br s, 2H), 5.30 (d, J=9.6 Hz, 1H), 3.81 (s, 3H), 3.79 (s, 3H), 3.73 (s, 1H), 3.61 (s, 3H), 3.50 (d, J=15.0 Hz, 1H), 3.45-3.12 (m, 6H), 3.08-2.90 (m, 2H), 2.83 (d, J=14.4 Hz, 1H), 2.72 (s, 3H), 2.68 (s, 1H), 2.65-2.53 (m, 1H), 2.46 (s, 3H), 2.46-2.28 (m, 2H), 2.22-2.10 (m, 1H), 2.11 (s, 3H), 2.00-1.88 (m, 2H), 1.82-1.70 (m, 2H), 1.39-1.21 (m, 2H), 0.95 (t, J=7.8 Hz, 3H), 0.80 (t, J=6.6 Hz, 3H); IR (film) $v_{max}$ 3467, 2958, 1740, 1615, 1501, 1458, 1432, 1370, 1228, 1041, 744 cm$^{-1}$; HRESI-TOFMS m/z 807.4315 (C$_{47}$H$_{58}$N$_4$O$_8$+H$^+$, required 807.4327); $[\alpha]_D^{23}$ +14 (c 0.75, CHCl$_3$).

10'-Methoxyanhydrovinblastine (22a)

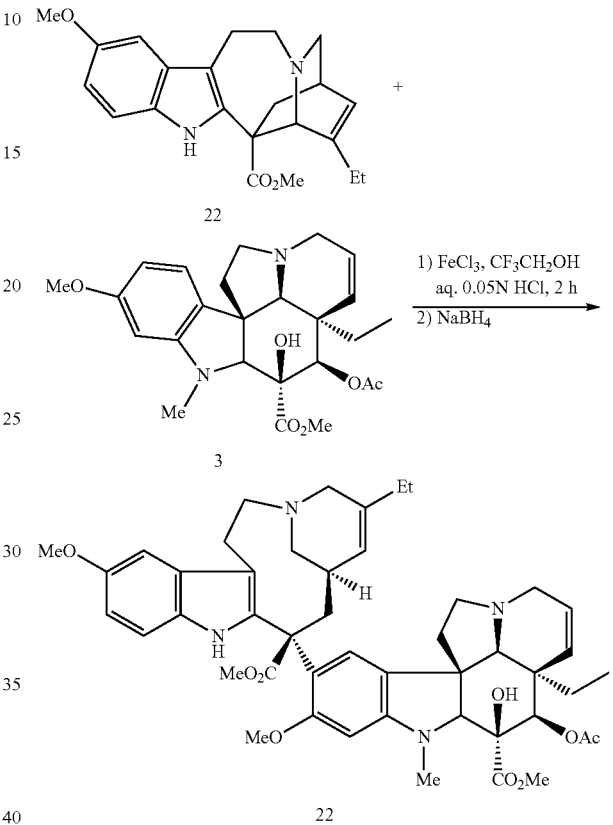

Iron(III) chloride hexahydrate (30.5 mg, 0.11 mmol, 5 equiv) was added to a solution of (−)-vindoline (3, 10.3 mg, 0.023 mmol, 1 equiv) and 10-methoxycatharanthine (22, 8.3 mg, 0.023 mmol, 1 equiv) in CF$_3$CH$_2$OH (0.09 mL), aqueous 0.1 N HCl (0.45 mL) and H$_2$O (0.45 mL) at room temperature under Ar. The reaction mixture was stirred for 2 hours at room temperature followed by cooling to 0° C. and addition of NaBH$_4$ (0.9 mg, 0.023 mmol, 1 equiv) in H$_2$O (0.5 mL). The resulting mixture was stirred for 30 minutes at 0° C. under Ar before being quenched with the addition of 28-30% NH$_4$OH (10 mL). The mixture was extracted with CH$_2$Cl$_2$ and the organic layer was dried over Na$_2$SO$_4$ and concentrated under reduced pressure. Flash chromatography (SiO$_2$, EtOAc) provided 10'-methoxyanhydrovinblastine (22a, 11.5 mg, 0.014, 62%) as a white solid.

For 22a: $^1$H NMR (600 MHz, CDCl$_3$) δ 9.81 (br s, 1H), 7.92 (s, 1H), 7.02 (d, J=9.0 Hz, 1H), 6.82 (s, 1H), 6.83 (dd, J=8.4, 1.8 Hz, 1H), 6.57 (br s, 1H), 6.11 (s, 1H), 5.86 (dd, J=10.2, 4.2 Hz, 1H), 5.51 (br s, 1H), 5.45 (s, 1H), 5.30 (d, J=10.8 Hz, 1H), 3.86 (s, 3H), 3.81 (s, 3H), 3.79 (s, 3H), 3.73 (s, 1H), 3.62 (s, 3H), 3.65-3.55 (m, 1H), 3.45-3.20 (m, 6H), 3.05-2.95 (m, 2H), 2.82 (d, J=16.2 Hz, 2H), 2.71 (s, 3H), 2.67 (s, 1H), 2.50-2.38 (m, 2H), 2.10 (s, 3H), 2.00-1.90 (m, 2H), 1.85-1.72 (m, 2H), 1.40-1.25 (m, 2H), 1.00 (t, J=7.2 Hz, 3H), 0.79 (t, J=7.2 Hz, 3H); IR (film) $v_{max}$ 3464, 2931, 1739, 1615, 1486, 1226, 1038, 732 cm$^{-1}$; HRESI-TOFMS m/z 823.4265 (C$_{47}$H$_{58}$N$_4$O$_9$+H$^+$, required 823.4276); $[\alpha]_D^{23}$ +15 (c 0.6, CHCl$_3$).

10′-Iodovinblastine (16b)

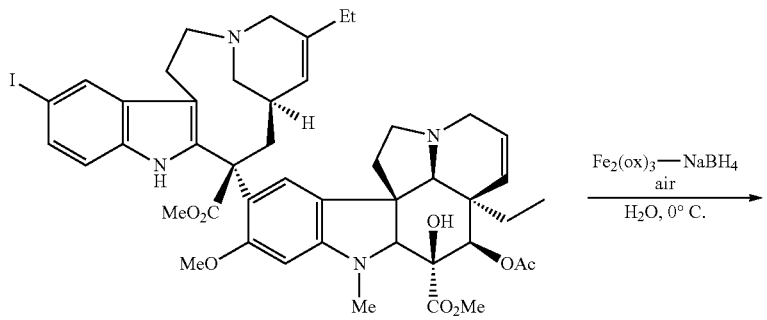

A mixture of iron(III) oxalate hexahydrate (112.4 mg, 0.23 mmol, 10 equiv) in H₂O (93 mL) was stirred for 2 hours, cooled to 0° C. and air was bubbled through the mixture for 10 minutes. A solution of 10′-iodoanhydrovinblastine (16a, 21.3 mg, 0.023 mmol, 1 equiv) in H₂O (0.5 mL), aqueous 0.1 N HCl (0.5 mL), and CF₃CH₂OH (0.1 mL) was transferred by pipette to the mixture and NaBH₄ (17.6 mg, 0.464 mmol, 20 equiv) in H₂O (1 mL) was added to the mixture at 0° C. The resulting mixture was stirred for 30 minutes before being quenched by addition of 28-30% aqueous NH₄OH (10 mL). The mixture was extracted with 10% MeOH in CH₂Cl₂ and the organic layer was dried over Na₂SO₄ and concentrated under reduced pressure. PTLC (SiO₂, Et₃N:MeOH:EtOAc=3:3:97) provided 10′-iodovinblastine (16b, 5.8 mg, 0.062 mmol, 27%) as a white solid and 10′-iodoleurosidine (2.3 mg, 0.0025 mmol, 11%). For 16b.

For 16b: $^1$H NMR (600 MHz, CDCl$_3$) δ 9.79 (br s, 1H), 8.07 (br s, 1H), 7.83 (s, 1H), 7.39 (d, J=8.4 Hz, 1H), 6.88 (d, J=9.0 Hz, 1H), 6.52 (s, 1H), 6.09 (s, 1H), 5.86 (dd, J=10.2, 4.8 Hz, 1H), 5.46 (s, 1H), 5.29 (d, J=9.6 Hz, 1H), 3.92 (t, J=13.8 Hz, 1H), 3.79 (s, 6H), 3.73 (s, 1H), 3.75-3.65 (m, 1H), 3.62 (s, 3H), 3.45-3.25 (m, 3H), 3.11 (dd, J=13.0, 4.8 Hz, 1H), 3.00 (dd, J=15.0, 5.4 Hz, 1H), 2.82 (s, 1H), 2.80 (s, 2H), 2.70 (s, 3H), 2.62 (s, 1H), 2.48-2.39 (m, 2H), 2.27 (br d, J=14.4 Hz, 1H), 2.20-2.12 (m, 1H), 2.11 (s, 3H), 1.85-1.75 (m, 3H), 1.55-1.20 (m, 6H), 0.89 (t, J=7.5 Hz, 3H), 0.76 (t, J=7.2 Hz, 3H); IR (film) $v_{max}$ 3465, 2925, 1739, 1614, 1501, 1460, 1432, 1370, 1228, 1040, 750 cm$^{-1}$; HRESI-TOFMS m/z 937.3228 (C$_{46}$H$_{57}$IN$_4$O$_9$+H$^+$, required 937.3243); $[α]_D^{23}$ −3.4 (c 0.3, CHCl$_3$).

10′-Bromovinblastine (17b)

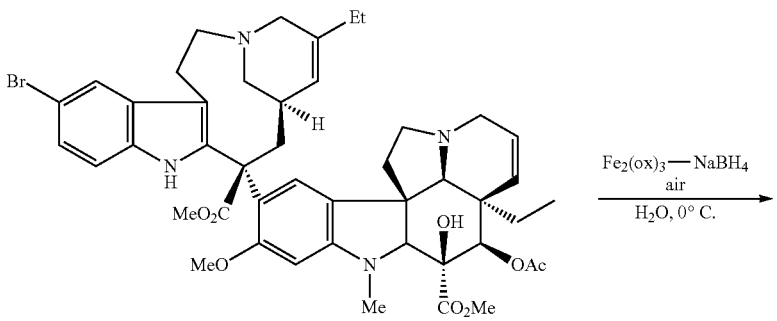

-continued

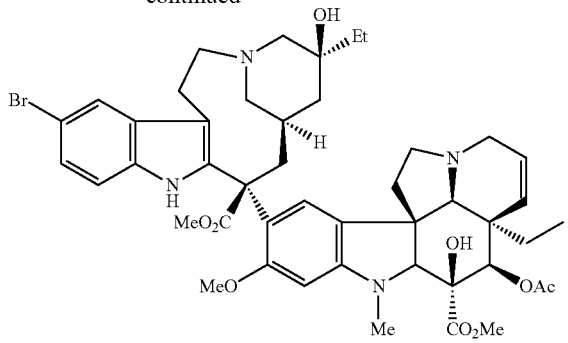

17b

A mixture of iron(III) oxalate hexahydrate (148.2 mg, 0.31 mmol, 30 equiv) in H$_2$O (41 mL) was cooled to 0° C. and air was bubbled through the mixture for 10 minutes. A solution of 10'-bromoanhydro-vinblastine (17a, 8.9 mg, 0.010 mmol, 1 equiv) in H$_2$O (0.5 mL), aqueous 0.1 N HCl (0.5 mL), and CF$_3$CH$_2$OH (0.1 mL) was transferred by pipette to the mixture and NaBH$_4$ (7.7 mg, 0.20 mmol, 20 equiv) in H$_2$O (1 mL) was added to the mixture at 0° C. The resulting mixture was stirred for 30 minutes before being quenched by addition of 28-30% aqueous NH$_4$OH (10 mL). The mixture was extracted with 10% MeOH in CH$_2$Cl$_2$ and the organic layer was dried over Na$_2$SO$_4$ and concentrated under reduced pressure. PTLC (SiO$_2$, Et$_3$N:MeOH:EtOAc=3:3:97) provided 10'-bromo-vinblastine (17b, 2.0 mg, 0.0022 mmol, 22%) and 10'-bromoleurosidine (1.3 mg, 0.0015 mmol, 14%).

For 17b: $^1$H NMR (600 MHz, CDCl$_3$) δ9.78 (br s, 1H), 8.07 (br s, 1H), 7.62 (s, 1H), 7.22 (d, J=8.4 Hz, 1H), 6.97 (d, J=8.4 Hz, 1H), 6.51 (s, 1H), 6.09 (s, 1H), 5.86 (dd, J=10.2, 4.8 Hz, 1H), 5.46 (s, 1H), 5.29 (d, J=10.2 Hz, 1H), 3.92 (t, J=13.2 Hz, 1H), 3.79 (s, 6H), 3.73 (s, 1H), 3.75-3.62 (m, 1H), 3.63 (s, 3H), 3.44-3.22 (m, 3H), 3.18-3.08 (m, 1H), 3.05-2.95 (m, 1H), 2.81 (s, 2H), 2.70 (s, 3H), 2.61 (s, 1H), 2.45-2.38 (m, 2H), 2.28 (br d, J=15.0 Hz, 1H), 2.22-2.12 (m, 1H), 2.11 (s, 3H), 1.88-1.70 (m, 3H), 1.50-1.20 (m, 6H), 0.88 (t, J=7.3 Hz, 3H), 0.76 (t, J=7.2 Hz, 3H); IR (film) v$_{max}$ 3451, 2924, 1739, 1613, 1502, 1463, 1433, 1371, 1230, 1040, 798 cm$^{-1}$; HRESI-TOFMS m/z 889.3351 (C$_{46}$H$_{57}$BrN$_4$O$_9$+H$^+$, required 889.3381); [α]$_D^{23}$ +6 (c 0.2, CHCl$_3$).

10'-Chlorovinblastine (18b)

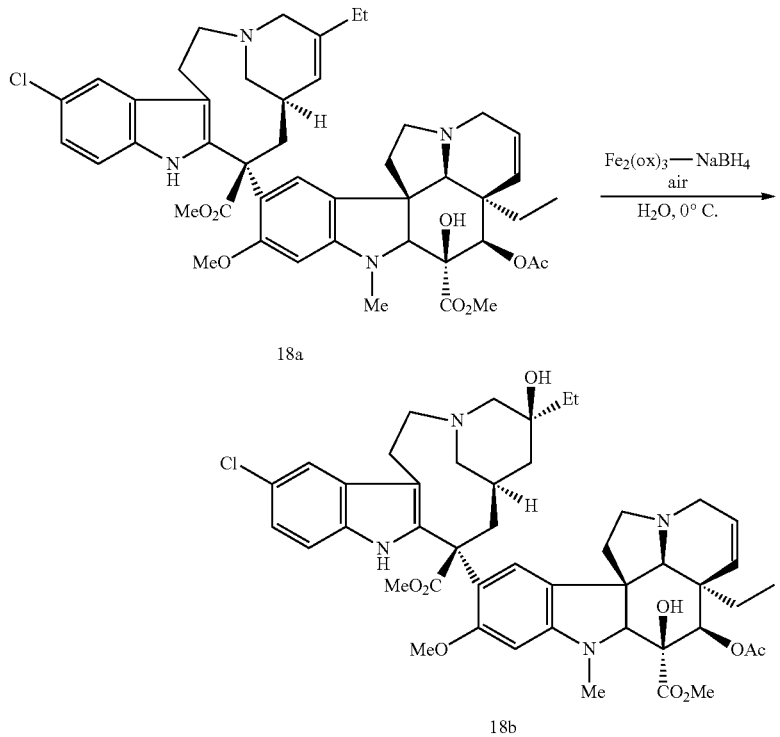

A mixture of iron(III) oxalate hexahydrate (52.6 mg, 0.109 mmol, 30 equiv) in H$_2$O was cooled to 0° C. and air was bubbled through the mixture for 10 minutes. A solution of 10'-chloroanhydrovinblastine (18a, 3.0 mg, 0.0036 mmol, 1 equiv) in H$_2$O (0.5 mL), aqueous 0.1 N HCl (0.5 mL), and CF$_3$CH$_2$OH (0.1 mL) was transferred by pipette to the mixture and NaBH$_4$ (2.7 mg, 0.073 mmol, 20 equiv) in H$_2$O (1 mL) was added to the mixture at 0° C. The resulting mixture was stirred for 30 minutes before being quenched by addition of 28-30% aqueous NH$_4$OH (10 mL). The mixture was extracted with 10% MeOH in CH$_2$Cl$_2$ and the organic layer was dried over Na$_2$SO$_4$ and concentrated under reduced pressure. PTLC (SiO$_2$, Et$_3$N:MeOH:EtOAc=3:3:97) provided 10'-chlorovinblastine (18b, 1.3 mg, 0.0015 mmol, 42%) as a white solid and 10'-chloroleurosidine (0.8 mg, 0.00095 mmol, 26%).

For 18b: $^1$H NMR (600 MHz, CDCl$_3$) δ 9.82 (br s, 1H), 8.02 (br s, 1H), 7.41 (d, J=8.4 Hz, 1H), 7.08 (s. 1H), 7.06 (d, J=8.4 Hz, 1H), 6.56 (s, 1H), 6.10 (s, 1H), 5.88 (dd, J=9.6, 3.6 Hz, 1H), 5.47 (s, 1H), 5.30 (d, J=10.2 Hz, 1H), 3.93 (t, J=13.8 Hz, 1H), 3.79 (s, 6H), 3.73 (s, 1H), 3.75-3.62 (m, 1H), 3.62 (s, 3H), 3.44-3.22 (m, 3H), 3.12 (d, J=13.2 Hz, 1H), 3.08-3.02 (m, 1H), 2.83 (s, 1H), 2.80 (s, 2H), 2.71 (s, 3H), 2.65 (s, 1H), 2.48-2.39 (m, 2H), 2.27 (br d, J=15.1 Hz, 1H), 2.22-2.15 (m, 1H), 2.11 (s, 3H), 1.85-1.75 (m, 3H), 1.50-1.20 (m, 6H), 0.89 (t, J=6.6 Hz, 3H), 0.81 (t, J=7.2 Hz, 3H); IR (film) v$_{max}$ 3463, 2926, 1740, 1614, 1460, 1231, 1040, 750 cm$^{-1}$; HRESI-TOFMS m/z 845.3879 (C$_{46}$H$_{57}$ClN$_4$O$_8$+H$^+$, required 845.3887); [α]$_D^{23}$ +20 (c 0.2, CHCl$_3$).

through the mixture for 10 minutes. A solution of 10'-fluoro-anhydrovinblastine (19a, 10.1 mg, 0.0125 mmol, 1 equiv) in H$_2$O (0.5 mL), aqueous 0.1 N HCl (0.5 mL), and CF$_3$CH$_2$OH (0.1 mL) was transferred by pipette to the mixture and NaBH$_4$ (9.5 mg, 0.25 mmol, 1 equiv) in H$_2$O (1 mL) was added to the mixture at 0° C. The resulting mixture was stirred for 30 minutes before being quenched by addition of 28-30% aqueous NH$_4$OH (10 mL). The mixture was extracted with 10% MeOH in CH$_2$Cl$_2$ and the organic layer was dried over Na$_2$SO$_4$ and concentrated under reduced pressure. PTLC (SiO$_2$, Et$_3$N:MeOH:EtOAc=3:3:97) provided 10'-fluorovinblastine 19b (4.0 mg, 0.0048 mmol, 39%) as a white solid and 10'-fluoroleurosidine (2.7 mg, 0.0033 mmol, 26%).

For 19b: $^1$H NMR (600 MHz, CDCl$_3$) δ 9.81 (br s, 1H), 8.00 (br s, 1H), 7.40 (dd, J=8.4, 5.4 Hz, 1H), 6.86 (t, J=9.0 Hz, 1H), 6.77 (dd, J=9.6, 1.8 Hz, 1H), 6.56 (s, 1H), 6.10 (s, 1H), 5.88 (dd, J=10.2, 4.2 Hz, 1H), 5.47 (s, 1H), 5.30 (d, J=10.2 Hz, 1H), 3.91 (t, J=14.4 Hz, 1H), 3.79 (s, 6H), 3.74 (s, 1H), 3.70-3.60 (m, 1H), 3.63 (s, 3H), 3.44-3.26 (m, 3H), 3.20-3.00 (m, 2H), 2.86-2.75 (m, $^3$H), 2.70 (s, 3H), 2.64 (s, 1H), 2.50-2.38 (m, 2H), 2.32-2.24 (m, 1H), 2.22-2.14 (m, 1H), 2.11 (s, 3H), 1.90-1.75 (m, 3H), 1.50-1.20 (m, 6H), 0.89 (t, J=7.2 Hz, 3H), 0.78 (t, J=7.2 Hz, 3H); IR (film) v$_{max}$ 2947, 1740, 1650, 10'-Fluorovinblastine (19b)

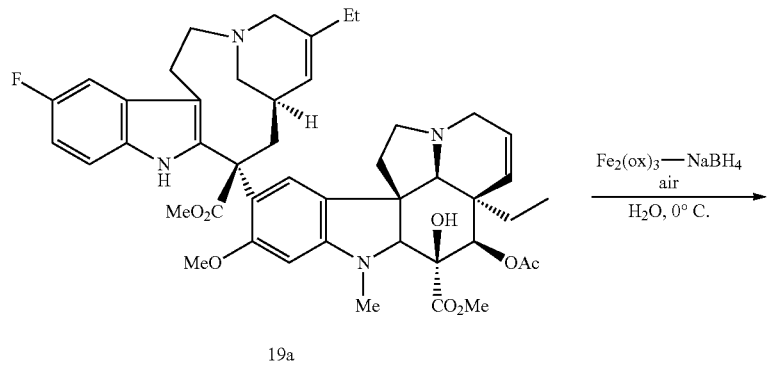

19a

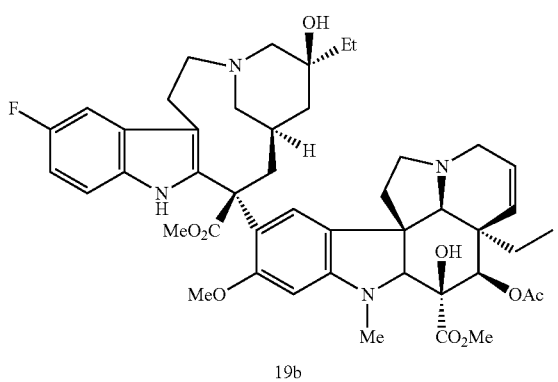

19b

A mixture of iron(III) oxalate hexahydrate (60.4 mg, 0.125 mmol, 10 equiv) in H$_2$O (50 mL) was stirred 2 hours. The reaction mixture was cooled to 0° C. and air was bubbled 1618, 1504, 1459, 1235, 1140, 1041 cm$^{-1}$; HRESI-TOFMS m/z 829.4179 (C$_{46}$H$_{57}$FN$_4$O$_9$+H$^+$, required 829.4182); [α]$_D^{23}$ +5 (c 0.44, CHCl$_3$).

10'-Thiomethylvinblastine (20b)

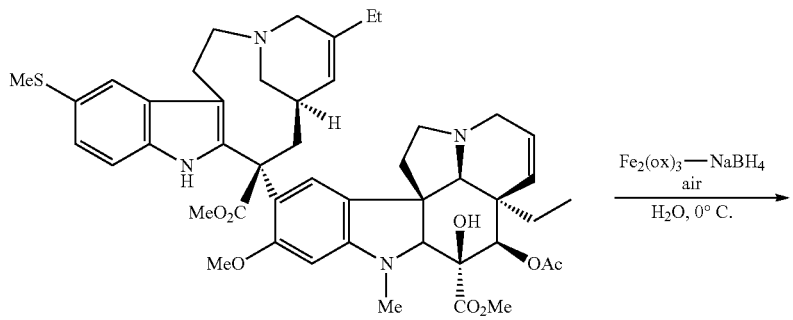

20a

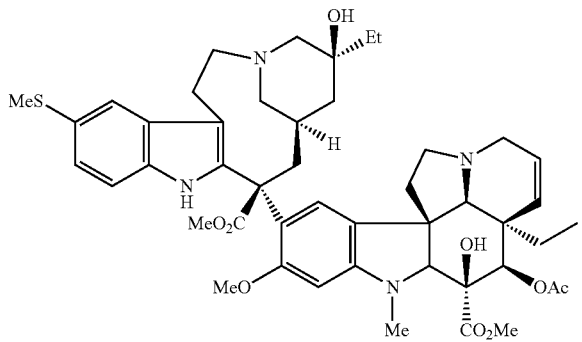

20b

A mixture of iron(III) oxalate hexahydrate (280.3 mg, 0.58 mmol, 30 equiv) in $H_2O$ (77 mL) was cooled to 0° C. and air was bubbled through the mixture for 10 minutes. A solution of 10'-thiomethylanhydro-vinblastine (20a, 16.2 mg, 0.019 mmol) in $H_2O$ (0.5 mL), aqueous 0.1 N HCl (0.5 mL), and $CF_3CH_2OH$ (0.1 mL) was transferred by pipette to the mixture and $NaBH_4$ (14.6 mg, 0.39 mmol, 1 equiv) in $H_2O$ (1 mL) was added to the mixture at 0° C. The resulting mixture was stirred for 30 minutes before being quenched by addition of 28-30% aqueous $NH_4OH$ (10 mL). The mixture was extracted with 10% MeOH in $CH_2Cl_2$ and the organic layer was dried over $Na_2SO_4$ and concentrated under reduced pressure. PTLC ($SiO_2$, $Et_3N$:MeOH:FtOAc=3:3:97) provided 10'-thiomethylvinblastine (20b, 5.1 mg, 0.0060 mmol, 31%) as a white solid and 10'-thiomethylleurosidine (2.5 mg, 0.0029 mmol, 15%).

For 20b: $^1H$ NMR (500 MHz, $CDCl_3$) δ 9.81 (br s, 1H), 8.03 (s, 1H), 7.53 (s, 1H), 7.19 (dd, J=8.5, 2.0 Hz, 1H), 7.05 (d, J=8.5 Hz, 1H), 6.58 (s, 1H), 6.10 (s, 1H), 5.86 (dd, J=10.5, 5.0 Hz, 1H), 5.46 (s, 1H), 5.29 (d, J=11.0 Hz, 1H), 3.94 (t, J=14.0 Hz, 1H), 3.79 (s, 6H), 3.73 (s, 1H), 3.70-3.60 (m, 1H), 3.61 (s, 3H), 3.42-3.25 (m, 3H), 3.15-3.05 (m, 2H), 2.83 (s, 1H), 2.81 (s, 1H), 2.71 (s, 3H), 2.64 (s, 1H), 2.52 (s, 3H), 2.48-2.38 (m, 2H), 2.30-2.24 (m, 1H), 2.20-2.12 (m, 1H), 2.10 (s, 3H), 1.85-1.74 (m, 3H), 1.50-1.20 (m, 6H), 0.89 (t, J=7.5 Hz, 3H), 0.79 (t, J=7.4 Hz, 3H); IR (film) $v_{max}$ 3467, 2961, 2823, 1739, 1614, 1503, 1461, 1434, 1371, 1231, 1040 $cm^{-1}$; HRESI-TOFMS m/z 857.4136 ($C_{47}H_{60}N_4O_9B+H^+$, required 857.4154); $[α]_D^{23}$ +8 (c 0.3, $CHCl_3$).

10'-Methylvinblastine (16b)

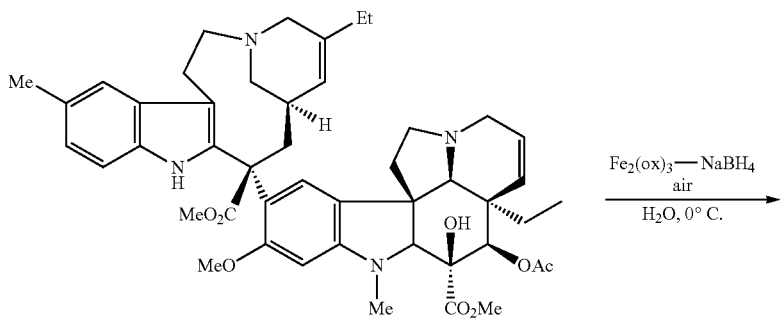

21a

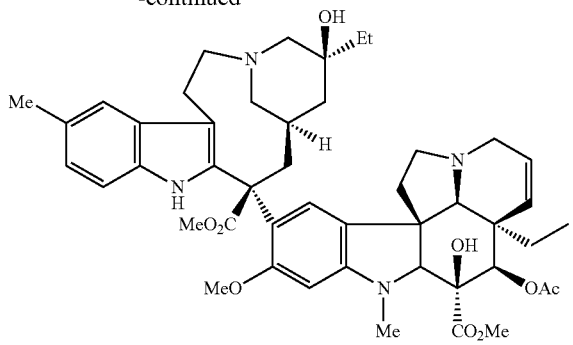

21b

A mixture of iron(III) oxalate hexahydrate (45.0 mg, 0.093 mmol) in H$_2$O (37 mL) was cooled to 0° C. and air was bubbled through the mixture for 10 minutes. A solution of 10'-methylanhydrovinblastine (21a, 7.5 mg, 0.0093 mmol, 1 equiv) in H$_2$O (0.5 mL), aqueous 0.1 N HCl (0.5 mL), and CF$_3$CH$_2$OH (0.1 mL) was transferred by pipette to the mixture and NaBH$_4$ (14.6 mg, 0.39 mmol, 1 equiv) in H$_2$O (1 mL) was added to the mixture at 0° C. The resulting mixture was stirred for 30 minutes before being quenched by addition of 28-30% aqueous NH$_4$OH (10 mL). The mixture was extracted with 10% MeOH in CH$_2$Cl$_2$ and the organic layer was dried over Na$_2$SO$_4$ and concentrated under reduced pressure. PTLC (SiO$_2$, Et$_3$N:MeOH:EtOAc=3:3:97) provided 10'-methylvinblastine (21b, 3.1 mg, 0.0038 mmol, 40%) as a white solid and 10'-methylleurosidine (1.5 mg, 0.0018 mmol, 19%).

For 21b: $^1$H NMR (500 MHz, CDCl$_3$) δ 9.86 (br s, 1H), 7.94 (br s, 1H), 7.30 (s, 1H), 7.01 (d, J=8.5 Hz, 1H), 6.97 (d, J=8.0 Hz, 1H), 6.65 (s, 1H), 6.10 (s, 1H), 5.84 (dd, J=9.5, 4.0 Hz, 1H), 5.46 (s, 1H), 5.29 (d, J=10.0 Hz, 1H), 3.96 (t, J=13.5 Hz, 1H), 3.79 (s, 6H), 3.72 (s, 1H), 3.70-3.60 (m, 1H), 3.60 (s, 3H), 3.45-3.25 (m, 3H), 3.15-3.07 (m, 2H), 2.85 (s, 1H), 2.81 (s, 2H), 2.70 (s, 3H), 2.67 (s, 1H), 2.48-2.35 (m, 2H), 2.45 (s, 3H), 2.32-2.23 (m, 1H), 2.20-2.12 (m, 1H), 2.10 (s, 3H), 1.85-1.74 (m, 3H), 1.50-1.20 (m, 6H), 0.89 (t, J=7.5 Hz, 3H), 0.81 (t, J=7.0 Hz, 3H); IR (film) v$_{max}$ 3465, 2959, 1740, 1615, 1502, 1231, 1040, 756 cm$^{-1}$; HRESI-TOFMS m/z 825.4400 (C$_{47}$H$_{60}$N$_4$O$_9$+H$^+$, required 835.4433); [α]$_D^{23}$ +10 (c 0.5, CHCl$_3$).

10'-Methoxyvinblastine (22b)

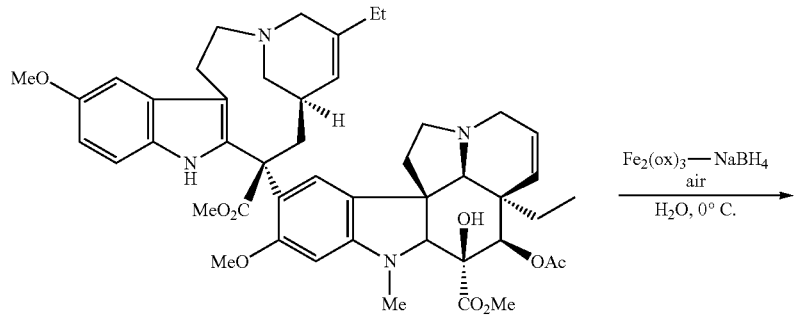

22a

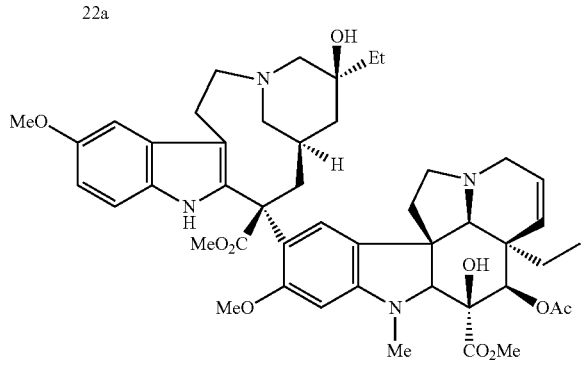

22b

A mixture of iron(III) oxalate hexahydrate (79.4 mg, 0.13 mmol, 30 equiv) in H$_2$O (22 mL) was cooled to 0° C. and air was bubbled through the mixture for 10 minutes. A solution of 10'-methoxyanhydro-vinblastine (22a, 4.5 mg, 0.0055 mmol, 1 equiv) in $H_2O$ (0.5 mL), aqueous 0.1 N HCl (0.5 mL), and $CF_3CH_2OH$ (0.1 mL) was transferred by pipette to the mixture and $NaBH_4$ (4.1 mg, 0.11 mmol, 20 equiv) in $H_2O$ (1 mL) was added to the mixture at 0° C. The resulting mixture was stirred for 30 min before being quenched by addition of 28-30% aqueous $NH_4OH$ (10 mL). The mixture was extracted with 10% MeOH in $CH_2Cl_2$ and the organic layer was dried over $Na_2SO_4$ and concentrated under reduced pressure. PTLC ($SiO_2$, $Et_3N$:MeOH:EtOAc=3:3:97) provided 10'-methoxyvinblastine (22b, 2.2 mg, 0.0026 mmol, 48%) as a white solid and 10'-methoxyleurosidine (1.3 mg, 0.0015 mmol, 28%).

For 22b: $^1H$ NMR (600 MHz, $CDCl_3$) δ 9.85 (hr s, 1H), 7.91 (br s, 1H), 7.01 (d, J=8.4 Hz, 1H), 6.95 (s, 1H), 6.82 (d, J=9.0 Hz, 1H), 6.64 (s, 1H), 6.10 (s, 1H), 5.86 (dd, J=9.0, 3.6 Hz, 1H), 5.47 (s, 1H), 5.30 (d, J=9.6 Hz, 1H), 3.95 (t, J=13.2 Hz, 1H), 3.86 (s, 3H), 3.79 (s, 6H), 3.73 (s, 1H), 3.70-3.60 (m, 1H), 3.61 (s, 3H), 3.45-3.25 (m, 3H), 3.20-3.00 (m, 2H), 2.84 (s, 1H), 2.81 (s, 2H), 2.71 (s, 3H), 2.67 (s, 1H), 2.48-2.35 (m, 2H), 2.30-2.12 (m, 2H), 2.11 (s, 3H), 1.90-1.75 (m, 3H), 1.50-1.20 (m, 6H), 0.89 (t, J=6.6 Hz, 3H), 0.80 (t, J=7.2 Hz, 3H); IR (film) $v_{max}$ 3463, 2923, 1738, 1662, 1615, 1452, 1224, 1038, 750 cm$^{-1}$; HRESI-TOFMS m/z 841.4351 ($C_{47}H_{60}N_4O_{10}+H^+$, required 841.4382); $[α]_D^{23}$ +3 (c 0.3, $CHCl_3$).

Iron(III) chloride hexahydrate (30.5 mg, 0.11 mmol, 5 equiv) was added to a solution of N-desmethylvindoline (10.0 mg, 0.023 mmol, 1 equiv) [Ishikawa et al., *J. Am. Chem. Soc.* 2009, 131, 4904-4916] and 10-fluorocatharanthine (8.0 mg, 0.023 mmol, 1 equiv) in $CF_3CH_2OH$ (0.09 mL), aqueous 0.1 N HCl (0.45 mL) and $H_2O$ (0.45 mL) at room temperature. The reaction mixture was stirred for 2 hours to form a coupling solution. Meanwhile, in a separate flask, a solution of iron(III) oxalate hexahydrate (110 mg, 0.23 mmol, 10 equiv) in $H_2O$ (90 mL) was cooled to 0° C. and air was bubbled through the mixture for 10 minutes. The coupling solution was transferred by pipette to this aqueous iron (III) oxalate solution and $NaBH_4$ (17 mg, 0.45 mmol, 20 equiv) in $H_2O$ (0.5 mL) was added to the mixture at 0° C. The resulting mixture was stirred for 30 minutes before being quenched by addition of 30% aqueous $NH_4OH$. The mixture was extracted with 10% MeOH in $CH_2Cl_2$ and the organic layer was dried over anhydrous $Na_2SO_4$ and concentrated under reduced pressure. PTLC ($SiO_2$, $Et_3N$:MeOH:EtOAc=3:3:97) afforded 1-demethyl-10'-fluorovinblastine, 27, (4.1 mg, 0.0049 mmol, 22%) as a white solid.

For 27: $^1H$ NMR (600 MHz, $CDCl_3$) 5.9.80 (br s, 1H), 7.99 (br s, 1H), 7.41 (dd, J=9.0, 5.4 Hz, 1H), 6.85 (dt, j=9.6, 1.8 Hz, 1H), 6.76 (dd, J=9.0, 1.8 Hz, 1H), 6.59 (br s, 1H), 6.21 (s, 1H), 5.86 (dd, J=10.2, 3.6 Hz, 1H), 5.51 (br s, 1H), 5.30 (d, J=9.0 Hz, 1H), 4.61 (d, J=3.0 Hz, 1H), 4.13 (d, J=3.0 Hz, 1H), 3.91 (t, J=13.8 Hz, 1H), 3.77 (s, 3H), 3.75 (s, 3H), 3.62 (s, 1H), 3.45-3.33 (m, 2H), 3.30-3.22 (m, 2H), 3.15-3.04 (m, 2H), 2.85-2.75 (m, 2H), 2.49 (s, 1H), 2.46-2.38 (m, 2H), 2.26 (d, J=12.6 Hz, 2H), 2.23-2.16 (m, 1H), 2.13 (s, 3H), 2.00-1.92 (m, 2H), 1.75-1.65 (m, 2H), 1.50-1.20 (m, 6H), 0.89 (t, J=7.2 Hz, 3H), 0.78 (t, J=7.2 Hz, 3H); IR (film) $v_{max}$ 3466, 2934, 1737, 1620, 1450, 1461, 1235, 1038, 753 cm$^1$; HRESI-TOFMS m/z 815.4019 ($C_{46}H_{55}FN_4O_8+H^+$, required 815.4026); $[α]_D^{23}$ +3 (c 0.4, $CHCl_3$).

1-Desmethyl-10'-fluorovinblastine (27)

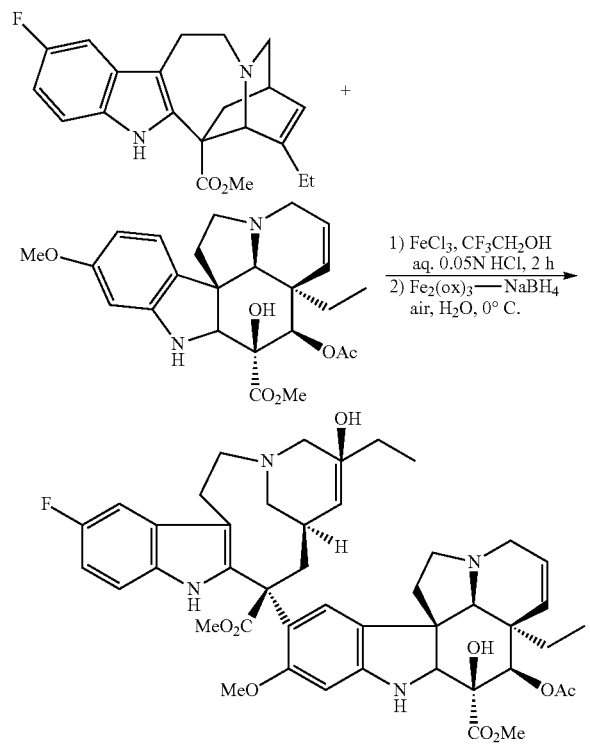

10'-Fluorovincristine (28)

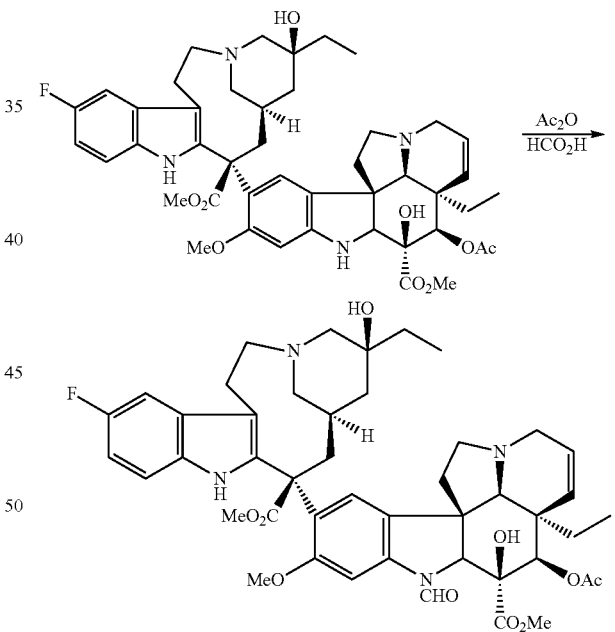

$Ac_2O$ (0.1 mL) was added to a solution of 1-desmethyl-10'-fluorovinblastine (3.1 mg, 0.0038 mmol) in formic acid (1 mL) under Ar. After 2 hours, $CH_2Cl_2$ (10 mL) was added, followed by dropwise addition of saturated aqueous $NaHCO_3$. The organic phase was separated, and aqueous phase was extracted twice with $CH_2Cl_2$. The organic solutions were combined, dried over anhydrous $Na_2SO_4$ and concentrated in vacuo. Flash chromatography ($SiO_2$, EtN: MeOH:EtOAc=3:3:97) afforded 10'-fluorovincristine (2.6 mg, 0.0031 mmol, 81%) as a white solid. 10'-Fluoro-vincristine, 28, was obtained as a mixture of two rotamers.

For 28: $^1$H NMR (500 MHz, CDCl$_3$) δ9.33 (br s, 1H), 8.76 (s, 0.6H), 8.17 (s, 0.4H), 8.03 (br s, 0.6H), 7.74 (br s, 0.4 H), 7.43 (dd, J=8.5, 5.5 Hz, 1H), 6.92-6.78 (m, 2H), 5.96-5.88 (m, 1H), 5.41 (d, J=10.5 Hz, 1H), 5.25 (s, 0.4H), 5.21 (s, 0.6 H), 4.74 (s, 0.6 H), 4.51 (s, 0.4 H), 4.02-3.93 (m, 1H), 3.89 (s, 1.2 H), 3.87 (s, 1.8H), 3.78 (s, 1.2 H), 3.72 (s, 1.8 H), 3.68 (s, 3H), 3.67 (s, 1H), 3.42-3.32 (m, 2H), 3.30-3.20 (m, 2H), 3.18-3.02 (m, 2H), 2.92-2.84 (m, 2H), 2.79 (br s, 2H), 2.62-2.55 (m, 1H), 2.40-2.28 (m, 2H), 2.20-2.10 (m, 1H), 2.09 (s, 1.2 H), 2.06 (s, 1.8 H), 1.80-1.60 (m, 2H), 1.48-1.20 (m, 6H), 0.95-0.79 (m, 6H), 0.63-0.58 (m, 1H); IR (film) ν$_{max}$ 2926, 1738, 1679, 1458, 1366, 1226, 1032 cm$^{-1}$; HRESI-TOFMS m/z 843.3970 (C$_{46}$H$_{55}$FN$_4$O$_{10}$+H$^+$, required 843.3975); [α]$_D^{23}$ +10 (c 0.3, CHCl$_3$).

Each of the patents, patent applications and articles cited herein is incorporated by reference. The use of the article "a" or "an" is intended to include one or more.

The foregoing description and the examples are intended as illustrative and are not to be taken as limiting. Still other variations within the spirit and scope of this invention are possible and will readily present themselves to those skilled in the art.

What is claimed:

1. A 10'-fluoro-vinca alkaloid compound or its pharmaceutically acceptable salt that corresponds in structure to a compound shown in Tables A or B below:

TABLE A

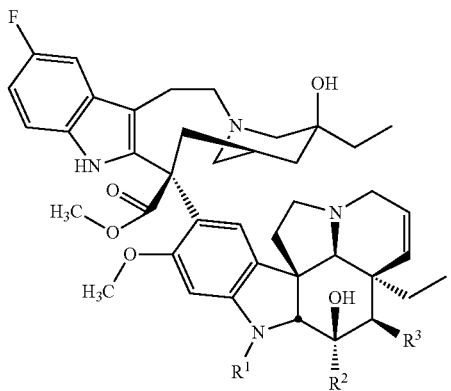

| | R$^1$ | R$^2$ | R$^3$ |
|---|---|---|---|
| 10'-Fluoro-vinblastine | —CH$_3$ | —C(O)—OCH$_3$ | —O—C(O)—CH$_3$ |
| 10'-Fluoro-vincristine | —CH(O) | —C(O)—OCH$_3$ | —O—C(O)—CH$_3$ |
| 10'-Fluoro-vindesine | —CH$_3$ | —C(O)—NH$_2$ | —OH |
| 1-Desmethyl-10'-fluoro-vinblastine | —H | —C(O)—OCH$_3$ | —O—C(O)—CH$_3$ |

TABLE B

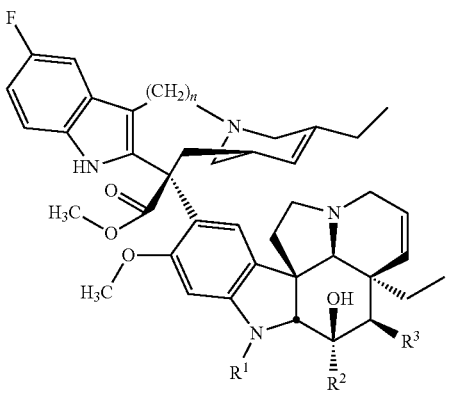

| | n | R$^1$ | R$^2$ | R$^3$ |
|---|---|---|---|---|
| 10'-Fluoro-vinorelbine | 1 | —CH$_3$ | —C(O)—OCH$_3$ | —O—C(O)—CH$_3$ |
| 10'-Fluoro-anhydro-vinblastine | 2 | —CH$_3$ | —C(O)—OCH$_3$ | —O—C(O)—CH$_3$ |
| 10'-Fluoro-anhydro-vincristine | 2 | —CH(O) | —C(O)—OCH$_3$ | —O—C(O)—CH$_3$ |
| 10'-Fluoro-anhydro-vindesine | 2 | —CH$_3$ | —C(O)—NH$_2$ | —OH. |

2. The 10'-fluoro-vinca alkaloid compound or its pharmaceutically acceptable salt according to claim 1, wherein said compound corresponds in structure to a compound shown in Table A.

3. The 10'-fluoro-vinca alkaloid compound or its pharmaceutically acceptable salt according to claim 1, wherein said compound corresponds in structure to a compound shown in Table B.

4. The 10'-fluoro-vinca alkaloid compound or its pharmaceutically acceptable salt according to claim 1, wherein said 10'-fluoro-vinca alkaloid compound is 10'-fluorovinblastine.

5. The 10'-fluoro-vinca alkaloid compound or its pharmaceutically acceptable salt according to claim 1, wherein said 10'-fluoro-vinca alkaloid compound is 10'-fluoroanhydrovinblastine.

6. The 10'-fluoro-vinca alkaloid compound or its pharmaceutically acceptable salt according to claim 1, wherein said 10'-fluoro-vinca alkaloid compound is 10'-fluorovincristine.

7. A pharmaceutical composition that comprises a microtubule formation-inhibiting or mitosis-inhibiting amount of a 10'-fluoro-vinca alkaloid compound of claim 1 or a pharmaceutically acceptable salt thereof dissolved or dispersed in a physiologically acceptable carrier.

8. The pharmaceutical composition according to claim 7, wherein said 10'-fluoro-vinca alkaloid compound corresponds in structure to a compound shown in Table A.

9. The pharmaceutical composition according to claim 7, wherein said 10'-fluoro-vinca alkaloid compound corresponds in structure to a compound shown in Table B.

10. The pharmaceutical composition according to claim 7, wherein said 10'-fluoro-vinca alkaloid compound is 10'-fluorovinblastine.

11. The pharmaceutical composition according to claim 7, wherein said 10'-fluoro-vinca alkaloid compound is 10'-fluoroanhydrovinblastine.

12. The pharmaceutical composition according to claim 7, wherein said 10'-fluoro-vinca alkaloid compound is 10'-fluorovincristine.

13. The pharmaceutical composition according to claim 7, wherein said composition is adapted for parenteral administration.

14. A method of treating a mammal with a colon cancer or leukemia that comprises administering a pharmaceutical composition according to claim 7 to the mammal.

15. The method of treatment according to claim 14, wherein said pharmaceutical composition is administered to said mammal a plurality of times.

16. The method of treatment according to claim 14, wherein said treatment is administered parenterally.

17. The method of treatment according to claim 16, wherein said 10'-fluoro-vinca alkaloid compound corresponds in structure to a compound shown in Tables A or B below:

TABLE A

| | $R^1$ | $R^2$ | $R^3$ |
|---|---|---|---|
| 10'-Fluoro-vinblastine | —$CH_3$ | —C(O)—$OCH_3$ | —O—C(O)—$CH_3$ |
| 10'-Fluoro-vincristine | —CHO | —C(O)—$OCH_3$ | —O—C(O)—$CH_3$ |
| 10'-Fluoro-vindesine | —$CH_3$ | —C(O)—$NH_2$ | —OH |
| 1-Desmethyl-10'-fluoro-vinblastine | —H | —C(O)—$OCH_3$ | —O—C(O)—$CH_3$ |

TABLE B

| | n | $R^1$ | $R^2$ | $R^3$ |
|---|---|---|---|---|
| 10'-Fluoro-vinorelbine | 1 | —$CH_3$ | —C(O)—$OCH_3$ | —O—C(O)—$CH_3$ |
| 10'-Fluoro-anhydro-vinblastine | 2 | —$CH_3$ | —C(O)—$OCH_3$ | —O—C(O)—$CH_3$ |
| 10'-Fluoro-anhydro-vincristine | 2 | —CHO | —C(O)—$OCH_3$ | —O—C(O)—$CH_3$ |
| 10'-Fluoro-anhydro-vindesine | 2 | —$CH_3$ | —C(O)—$NH_2$ | —OH |

18. The method of treatment according to claim 17, wherein said 10'-fluoro-vinca alkaloid compound corresponds in structure to a compound shown in Table A.

19. The method of treatment according to claim 17, wherein said 10'-fluoro-vinca alkaloid compound corresponds in structure to a compound shown in Table B.

20. The method of treatment according to claim 17, wherein said 10'-fluoro-vinca alkaloid compound is 10'-fluorovinblastine.

21. The method of treatment according to claim 17, wherein said 10'-fluoro-vinca alkaloid compound is 10'-fluoroanhydrovinblastine.

22. The method of treatment according to claim 17, wherein said 10'-fluoro-vinca alkaloid compound is 10'-fluorovincristine.

23. In a method of treating a mammal with cancer, lymphoma or leukemia that comprises administering a pharmaceutical composition containing an effective amount of a microtubule formation-inhibiting or mitosis-inhibiting amount of a vinca alkaloid, the improvement that comprises replacing said effective amount of a vinca alkaloid with an effective amount of a 10'-fluoro-vinca alkaloid compound that corresponds in structure to a compound shown in Tables A or B below:

TABLE A

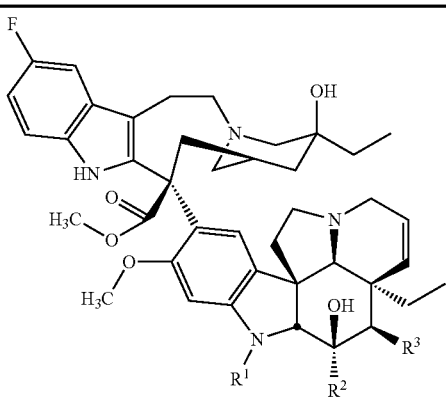

| | R¹ | R² | R³ |
|---|---|---|---|
| 10'-Fluoro-vinblastine | —CH₃ | —C(=O)—OCH₃ | —O—C(=O)—CH₃ |
| 10'-Fluoro-vincristine | —CH(=O) | —C(=O)—OCH₃ | —O—C(=O)—CH₃ |
| 10'-Fluoro-vindesine | —CH₃ | —C(=O)—NH₂ | —OH |
| 1-Desmethyl-10'-fluoro-vinblastine | —H | —C(=O)—OCH₃ | —O—C(=O)—CH₃ |

TABLE B

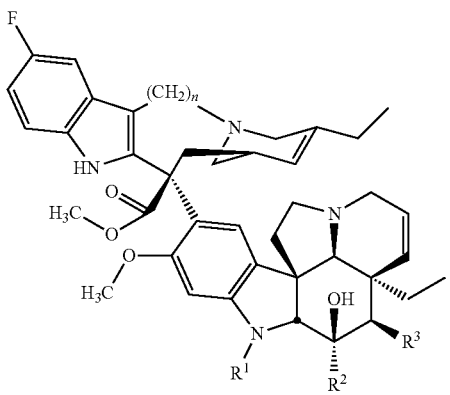

| | n | R¹ | R² | R³ |
|---|---|---|---|---|
| 10'-Fluoro-vinorelbine | 1 | —CH₃ | —C(=O)—OCH₃ | —O—C(=O)—CH₃ |

TABLE B-continued

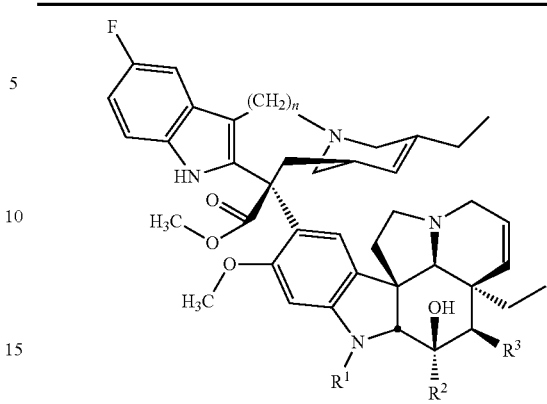

| | n | R¹ | R² | R³ |
|---|---|---|---|---|
| 10'-Fluoro-anhydro-vinblastine | 2 | —CH₃ | —C(=O)—OCH₃ | —O—C(=O)—CH₃ |
| 10'-Fluoro-anhydro-vincristine | 2 | —CH(=O) | —C(=O)—OCH₃ | —O—C(=O)—CH₃ |
| 10'-Fluoro-anhydro-vindesine | 2 | —CH₃ | —C(=O)—NH₂ | —OH. |

24. The method of treatment according to claim 23, wherein said pharmaceutical composition is administered to said mammal a plurality of times.

25. The method of treatment according to claim 23, wherein said treatment is administered parenterally.

26. The method of treatment according to claim 23, wherein said 10'-fluoro-vinca alkaloid compound corresponds in structure to a compound shown in Table A.

27. The method of treatment according to claim 23, wherein said 10'-fluoro-vinca alkaloid compound corresponds in structure to a compound shown in Table B.

28. The method of treatment according to claim 23, wherein said 10'-fluoro-vinca alkaloid compound is 10'-fluorovinblastine.

29. The method of treatment according to claim 23, wherein said 10'-fluoro-vinca alkaloid compound is 10'-fluoroanhydrovinblastine.

30. The method of treatment according to claim 23, wherein said 10'-fluoro-vinca alkaloid compound is 10'-fluorovincristine.

* * * * *

UNITED STATES PATENT AND TRADEMARK OFFICE
CERTIFICATE OF CORRECTION

PATENT NO. : 8,940,754 B2  
APPLICATION NO. : 13/580340  
DATED : January 27, 2015  
INVENTOR(S) : Dale L. Boger Page 1 of 1

It is certified that error appears in the above-identified patent and that said Letters Patent is hereby corrected as shown below:

In the Specification:

Column 1, Lines 14-17; Change:

"The present invention was made with governmental support pursuant to grants CA115526, CA042056 and GM087948 from the National Institutes of Health. The government has certain rights in the invention."

to

"This invention was made with government support under CA115526, CA042056, & GM087948 awarded by the National Institutes of Health. The government has certain rights in the invention."

Signed and Sealed this  
Twelfth Day of July, 2016

Michelle K. Lee  
*Director of the United States Patent and Trademark Office*